(12) United States Patent
Amantini et al.

(10) Patent No.: US 11,136,325 B2
(45) Date of Patent: Oct. 5, 2021

(54) PYRROLOPYRIMIDINE AND PYRROLOPYRIDINE DERIVATIVES

(71) Applicant: GALAPAGOS NV, Mechelen (BE)

(72) Inventors: David Amantini, Romainville (FR); Milan Mesic, Zagreb (HR); Gordon Saxty, Zagreb (HR); Tanja Poljak, Zagreb (HR); Ines Vujasinovic, Zagreb (HR); Dinko Ziher, Zagreb (HR); David Witty, Cambridge (GB); Karl Richard Gibson, Kent (GB)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 16/632,202

(22) PCT Filed: Jul. 12, 2018

(86) PCT No.: PCT/GB2018/051983
§ 371 (c)(1),
(2) Date: Jan. 17, 2020

(87) PCT Pub. No.: WO2019/012284
PCT Pub. Date: Jan. 17, 2019

(65) Prior Publication Data
US 2020/0165259 A1 May 28, 2020

(30) Foreign Application Priority Data
Jul. 12, 2017 (GB) ..................................... 1711234

(51) Int. Cl.
| | |
|---|---|
| *C07D 487/04* | (2006.01) |
| *A61P 1/16* | (2006.01) |
| *A61P 19/02* | (2006.01) |
| *A61P 25/04* | (2006.01) |
| *A61P 11/00* | (2006.01) |
| *C07D 471/04* | (2006.01) |

(52) U.S. Cl.
CPC .............. *C07D 487/04* (2013.01); *A61P 1/16* (2018.01); *A61P 11/00* (2018.01); *A61P 19/02* (2018.01); *A61P 25/04* (2018.01); *C07D 471/04* (2013.01)

(58) Field of Classification Search
CPC ........................... C07D 487/04; C07D 471/04
See application file for complete search history.

(56) References Cited

FOREIGN PATENT DOCUMENTS

| | | |
|---|---|---|
| EP | 2058309 A1 | 5/2009 |
| WO | 2001039777 A1 | 6/2001 |
| WO | 2004048565 A1 | 6/2004 |
| WO | 2008016131 A1 | 2/2008 |
| WO | 2008075172 A2 | 6/2008 |
| WO | 2009027283 A1 | 3/2009 |
| WO | 2009123986 A1 | 10/2009 |
| WO | 2012080735 A1 | 6/2012 |

OTHER PUBLICATIONS

Takeda et al., "Apoptosis Signal-Regulatin Kinase 1 in Stress and Immune Response", Annu Rev Pharacol Toxicol, (2008), vol. 48, pp. 199-225.
Nagai et al., "Pathophysiological Roles of ASK1-MAP Kinase Signaling Pathways", Journal of Biochemistry and Molecular Biology, (2007), vol. 40, No. 1, pp. 1-6.
Davis, "Signal Transduction by the JNK Group of MAP Kinases", Cell, (2000), vol. 103, pp. 239-252.
Ichijo et al., "Induction of Apoptosis by ASK1, a Mammalian MAPKKK That Activates SAPK/JNK and p38 Signaling Pathways", Science, (1997), vol. 275, pp. 90-94.
Hao et al., "Gene Transfer to Interfere with TNFα Signaling in Neuropathic Pain", Gene Therapy, (2007), vol. 14, pp. 1010-1016.
Tobiume et al., "ASK1 is Required for Sustained Activations of JNK/p38 MAP Kenases and Apoptosis", EMBO Reports, (2001), vol. 2, No. 3, pp. 222-228.
Ji and Suter, "p38 MAPK, Microglial Signaling, and Neuropathic Pain", Molecular Pain, (2007), vol. 3, No. 33, pp. 1-9.
Cheng et al., "Inflammatory Pain-Induced Signaling Events Following a Conditional Deletion of the N-Methyl-D-Aspartate Receptor in Spinal Cord Dorsal Horn", Neuroscience, (2008), vol. 155, No. 3, pp. 948-958.

(Continued)

*Primary Examiner* — Susanna Moore
(74) *Attorney, Agent, or Firm* — Arent Fox LLP

(57) ABSTRACT

The present invention relates to pyrrolopyrimidine compounds according to Formula I and their use in the prophylaxis and/or treatment of pain, inflammatory conditions, cardiovascular diseases, neurodegenerative diseases, neurological diseases, complications of type I diabetes, cancer and/or fibrotic diseases. In a particular aspect, the present compounds are ASK inhibitors, particularly ASK1 inhibitors. The present invention also provides methods for the production of a compound of the invention, pharmaceutical compositions comprising a compound of the invention, the use of the compounds in the prophylaxis and/or treatment of pain, inflammatory conditions, cardiovascular diseases, neurodegenerative diseases, neurological diseases, complications of type I diabetes, cancer and/or fibrotic diseases.

14 Claims, 10 Drawing Sheets
Specification includes a Sequence Listing.

(56) References Cited

OTHER PUBLICATIONS

Ji and Gao, "Activation of JNK Pathway in Persistent Pain", Neurosci Lett, (2008), vol. 437, No. 3, pp. 180-183.
Younossi et al., "Changes in the Prevalence of the Most Common Causes of Chronic Liver Diseases in the United States From 1988 to 2008", Clinical Gastroenterology and Hepatology, (2011), vol. 9, pp. 524-530.
Cohen et al., "Human Fatty Liver Disease: Old Questions and New Insights" Science, (2011), vol. 332, pp. 1519-1523.
Singh et al., "Fibrosis Progression in Nonalcoholic Fatty Liver versus Nonalcoholic Steatohepatitis: A Systematic Review and Meta-analysis of Paired-Biopsy Studies", Clinical Gastroenterology and Hepatology, (2015), vol. 13, pp. 643-654.
McPherson et al., "Evidence of NAFLD Progression from Steatosis to Fibrosing-Steatohepatitis Using Paired Biopsies: Implications for Prognosis and Clinical Management", Journal of Hepatology, (2015), vol. 62, pp. 1148-1155.
Bian and Ma, "Liver Fibrogenesis in Non-Alcoholic Steatohepatitis", Frontiers in Physiology, (2012), vol. 3, No. 248, pp. 1-7.
Koek et al., "The Role of Oxidative Stress in Non-Alcoholic Steatohepatitis", Clinica Chimica Acta, (2011), vol. 412, pp. 1297-1305.
Serviddio et al., "Free Radical Biology for Medicine: Learning from Nonalcoholic Fatty Liver Disease", Free Radical Biology and Medicine, (2013), vol. 65, pp. 952-968.
Al-Serri et al., "The SOD2 C47T Polymorphism Influences NAFLD Fibrosis Severity: Evidence from Case-Control and Intra-Familial Allele Association Studies", Journal of Hepatology, (2012), vol. 56, pp. 448-454.
Wehr et al., "Chemokine Receptor CXCR6-Dependent Hepatic NK T Cell Accumulation Promotes Inflammation and Liver Fibrosis", Journal of Immunology, (2013), vol. 190, No. 10, pp. 5226-5236.
Baeck et al., "Pharmacological Inhibition of the Chemokine C—C Motif Chemokine Ligand 2 (Monocyte Chemoattractant Protein 1) Accelerates Liver Fibrosis Regression by Suppressing Ly-6C1+ Macrophage Infiltration in Mice", Hepatology, (2014), vol. 59, No. 3, pp. 1060-1072.
Gautheron et al., "A Positive Feedback Loop Between RIP3 and JNK Controls Non-Alcoholic Steatohepatitis", EMBO Molecular Medicine, (2014), vol. 6, No. 8, pp. 1062-1074.
Ashcroft et al., "Simple Method of Estimating Severity of Pulmonary Fibrosis on a Numerical Scale", Journal of Clinical Phathology, (1988), vol. 41, pp. 467-470.
Matsuse et al., "ICAM-1 Mediates Lung Leukocyte Recruitment but not Pulmonary Fibrosis in a Murine Model of Bleomycin-Induced Lung Injury", European Respiratory Journal, (1999), vol. 13, pp. 71-77.
Jou et al., "Thrombospondin 1 as an Effective Gene Therapeutic Strategy in Collagen-Induced Arthritis", Arthritis and Rheumatism, (2005), vol. 52, No. 1, pp. 339-344.
Sims et al., "Targeting Osteoclasts With Zoledronic Acid Prevents Bone Destruction in Collagen-Induced Arthritis", Arthritis and Rheumatism, (2004), vol. 50, No. 7, pp. 2338-2346.
Khachigian, "Collagen Antibody-Induced Arthritis", Nature Protocols, (2006), vol. 1, No. 5, pp. 2512-2516.
Lin et al., "Anti-Rheumatic Activities of Histone Deacetylase (HDAC) Inhibitors in Vivo in Collagen-Induced Arthritis in Rodents", British Journal of Pharmacology, (2007), vol. 150, pp. 862-872.
Nishida et al., "Histone Deacetylase Inhibitor Suppression of Autoantibody-Mediated Arthritis in Mice via Regulation of p16INK4a and p21WAF1/Cip1 Expression" Arthritis and Rheumatism, (2004), vol. 50, No. 10, pp. 3365-3376.
Rall and Roubenoff, "Rheumatoid Cachexia: Metabolic Abnormalities, Mechanisms, and Interventions", Rheumatology, (2004), vol. 43, No. 10, pp. 1219-1223.
Shelton et al., "Nerve Growth Factor Mediates Hyperalgesia and Cachexia in Auto-Immune Arthritis", Pain, (2005), vol. 116, pp. 8-16.
Walsmith et al., "Tumor Necrosis Factor-α Production is Associated with Less Body Cell Mass in Women with Rheumatoid Arthritis", Jornal of Rheumatology, (2004), vol. 31, pp. 23-29.
Bush et al., "Reduction of Joint Inflammation and Bone Erosion in Rat Adjuvant Arthritis by Treatment With Interleukin-17 Receptor IgG1 Fc Fusion Protein", Arthritis and Rheumatism, (2002), vol. 46, No. 3, pp. 802-805.
Salvernini et al., "Amelioration of Joint Disease in a Rat Model of Collagen-Induced Arthritis by M40403, a Superoxide Dismutase Mimetic", Arthritis and Rheumatism, (2001), vol. 44, No. 12, pp. 2909-2921.
Oste et al., "A High Throughput Method of Measuring Bone Architectural Disturbance in a Murine CIA Model by Micro-Ct Morphometry", Calcified Tissue International, (2007), 80:S68-S69.
Bendele, "Animal Models of Rheumatoid Arthritis", J Musculoskel Neuron Interact, (2001), vol. 1, No. 4, pp. 377-385.
Janusz et al., "Induction of Osteoarthritis in the Rat by Surgical Tear of the Meniscus: Inhibition of Joint Damage by a Matrix Metalloproteinase Inhibitor", Osteoarthritis and Cartilage, (2002), vol. 10, pp. 785-791.
Pritzker et al., "Osteoarthritis Cartilage Histopathology: Grading and Staging", Osteoarthritis and Cartilage, (2006), vol. 14, pp. 13-29.
Grimm et al., "The Conduct of in Vitro Studies to Address Time-Dependent Inhibition of Drug-Metabolizing Enzymes: A Perspective of the Pharmaceutical Research and Manufacturers of America" Drug Metabolism and Disposition, 2009, vol. 37, No. 7, pp. 1355-1370.
International Search Report and Written Opinion for PCT/GB2018/051983, dated Sep. 10, 2018.

A

B

C
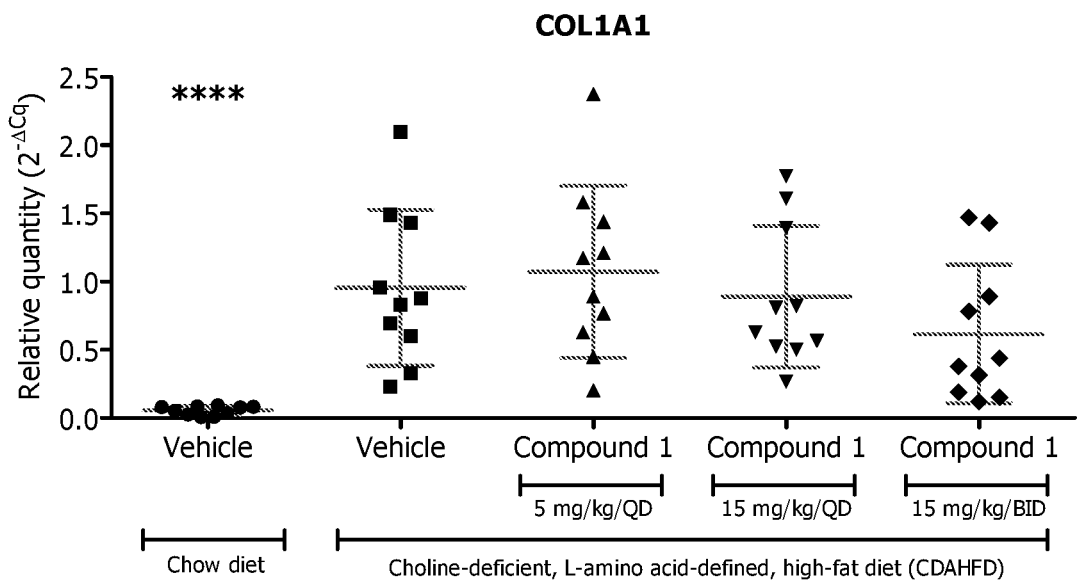
D
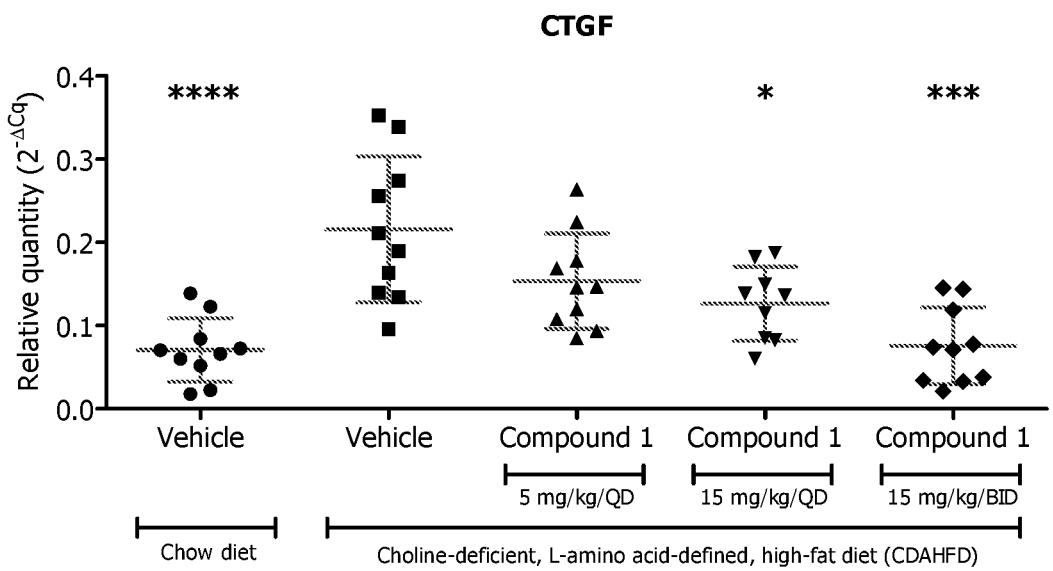
FIGURE 3 (ctd)

E
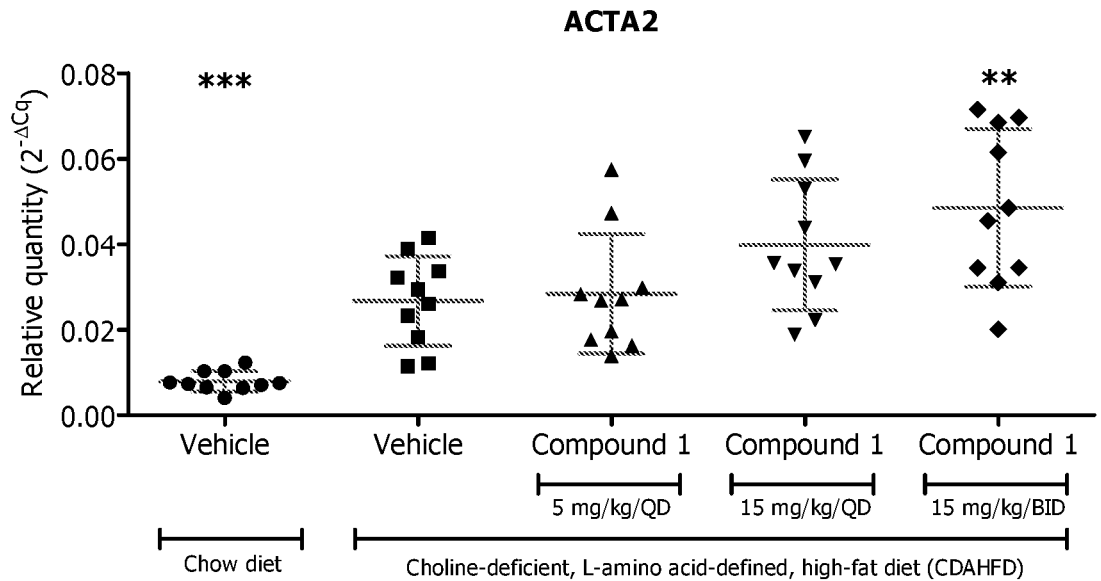
F
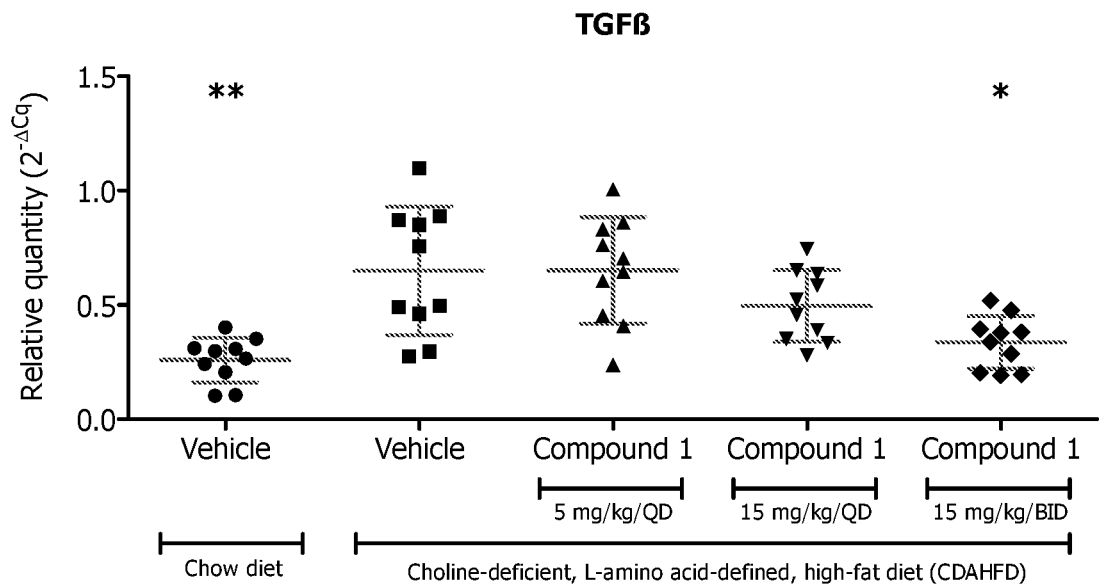
FIGURE 3 (ctd)

A

B

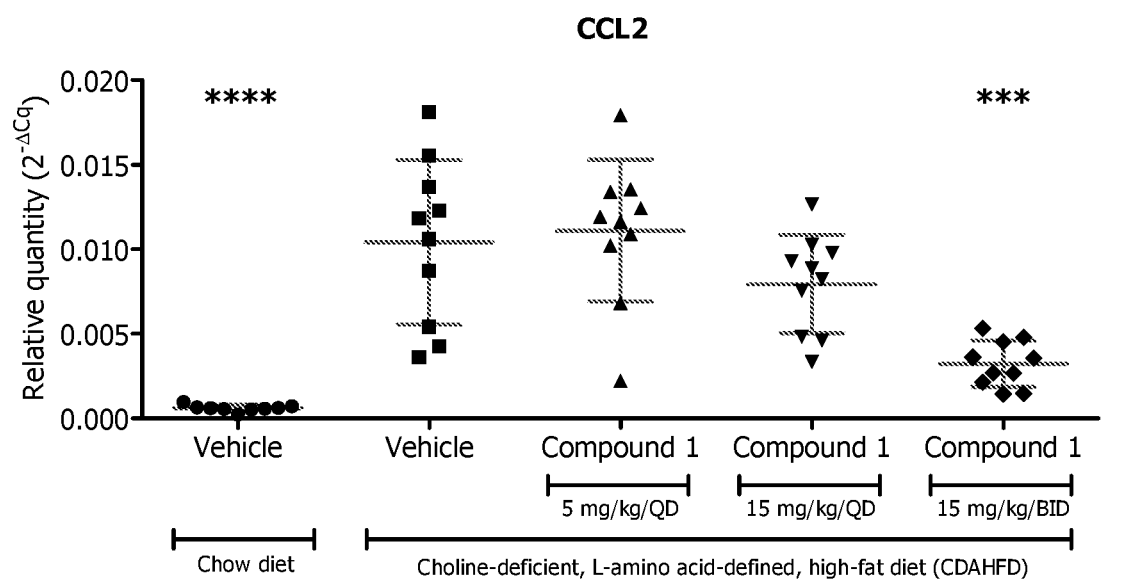
FIGURE 4 (ctd)

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial
<220> FEATURE:
<223> OTHER INFORMATION: Synthetic Peptide

<400> SEQUENCE: 1

Gly Thr Phe Arg Ala Ala Ile Arg Arg Leu Ala Ala Arg Arg Arg
1               5                   10                  15
```

PYRROLOPYRIMIDINE AND PYRROLOPYRIDINE DERIVATIVES

FIELD OF THE INVENTION

The present invention relates to pyrrolopyrimidine compounds and their use in the prophylaxis and/or treatment of pain, inflammatory conditions, cardiovascular diseases, neurodegenerative diseases, neurological diseases, complications of diabetes, cancer and/or fibrotic diseases. In a particular aspect, the present compounds are ASK inhibitors, particularly ASK1 inhibitors. The present invention also provides methods for the production of a compound of the invention, pharmaceutical compositions comprising a compound of the invention, the use of the compounds in the prophylaxis and/or treatment of pain, inflammatory conditions, cardiovascular diseases, neurodegenerative diseases, neurological diseases, complications of diabetes, cancer and/or fibrotic diseases.

BACKGROUND OF THE INVENTION

Apoptosis signal-regulating kinase (ASK1) is a ubiquitously expressed Ser/Thr kinase on the mitogen-activated protein kinase (MAPK) signalling pathway inducing response to stress stimuli including proinflammatory molecules such as tumor necrosis factor-α (TNF-α) and lipopolysaccharide (LPS), endoplasmic stress, oxidative stress, genotoxic stress, free radicals, Fas ligand and calcium overload (Takeda K et al (2008) Annu Rev Pharacol Toxicol 248 pp 199-225; Nagai H et al (2007) J Biochem Mol Biol 40 pp 1-6).

ASK1 is one of a number of MAP kinase kinase kinases (MAP3Ks) which signal through MAP kinase kinases (MKKs). In the case of ASK1 signalling, MKK3 and MKK6 activate the p38 pathway and MKK4 and MKK7 activate the JNK pathway (Davis R J (2000) Cell 103 pp 239-252; Ichijo H et al (1997) Science 275 pp 90-94). Therefore inhibitors of ASK1 have the potential to suppress signalling pathways through both p38 and JNK.

The use of soluble TNF receptor: Fc fusion protein Enbrel (etanercept) has been shown to be efficacious in the clinic for inflammatory pain and also in pre-clinical models for neuropathic pain (Hao S et al (2007) Gene Therapy 14 pp 1010-1016) implying that TNF-α is a key mediator in pain response. IL-6 is a key downstream mediator of TNF-α signalling and there is clinical evidence supporting anti-IL-6 therapy as a valid therapeutic approach for rheumatoid arthritis (Roche has published positive Phase III results for Actemra/Tocilizumab in May 2008).

A number of cells that do not have functional ASK1 (isolated from ASK1 knockout mice, or following gene silencing) are resistant to TNF-α induced apoptosis (Tobiume K, et al (2001) EMBO Rep 2 pp 222-228). ASK1 is therefore pivotal in the TNF-α pathway and supports the hypothesis that disrupting the TNF-α signalling pathway via ASK1 inhibition would lead to beneficial downstream effects such as relief from pain. There is strong evidence to link activation of p38 and/or JNK with the production of pro-inflammatory mediators and subsequent pain response (Ji R-R and Suter M R (2007) Molecular Pain 3 pp 33-41; Cheng H T et al (2008) Neuroscience 155 pp 948-958; Ji R-R and Gao Y-J (2008) Neurosci Lett 437 pp 180-183). As ASK1 activation can lead to the activation of both p38 and JNK, inhibition of ASK1 has the potential to be more powerful than p38 inhibitors alone and, as it is higher up in the signalling cascade, may limit the likelihood of unwanted liabilities.

Fibrosis is a wound-healing process in which there is excessive deposition of extracellular matrix (ECM). ECM is composed of collagens, noncollagen glycoproteins, matrix bound growth factors, glycosaminoglycans, proteoglycans and matricellular proteins, which provide the scaffolding of both the normal and the fibrotic tissue.

Non-alcoholic fatty liver disease (NAFLD) is the most common cause of chronic liver disease in developed countries (Younossi Z M, et al., Clin Gastroenterol Hepatol 2011; 9: 524-30 and Cohen J C, et al., Science, 2011; 332: 1519-23). It may be broadly classified into two categories: non-alcoholic fatty liver (or simple steatosis) and non-alcoholic steatohepatitis (NASH). Although previously it was thought that steatosis was largely nonprogressive while NASH was the progressive form of NAFLD, recent evidence from serial biopsy studies demonstrates that patients with steatosis or NASH have an increased risk of subsequent disease progression to advanced fibrosis and cirrhosis (Singh S, et al, Clin Gastroenterol Hepatol 2015; 13: 643-54 and McPherson S, et al., J Hepatol 2015; 62: 1148-55).

Oxidative stress is known to play a major role in the activation of hepatic stellate cells (HSCs) in NASH (Bian Z, & Ma X. Front Physiol 2012; 3: 248 and Koek G H, et al., Clin Chim Acta 2011; 412: 1297-305), and anti-oxidants not only exert a preventive effect on hepatocyte injury but may directly contribute to decreasing fibrogenesis, (Serviddio G et al., Free Radic Biol Med 2013; 65: 952-68) an effect supported by gene-association studies where variants affecting cellular anti-oxidant defences efficacy influence risk of NAFLD fibrosis (Al-Serri A, et al., J Hepatol 2012; 56: 448-54).

Apoptosis-signal-regulating kinase 1 (ASK1) is a kinase that is activated by various stimuli including hyperglycaemia, TGF-β and ROS (Karnik S, Charlton M R, Li L, et al., The Liver Meeting 2015, San Francisco, Calif., November 13-17, American Association for the Study of Liver Diseases, 2015). ASK1 induces apoptosis, fibrosis and metabolic dysfunction by activating the p38 and JNK1 pathways. The ASK1 pathway has been shown to be activated in human NASH liver biopsies (Karnik S, The Liver Meeting 2014, Boston, Mass., November 7-11, American Association for the Study of Liver Diseases, 2014). Furthermore, in a six month NASH human clinical study, the ASK1 inhibitor selonsertib has been shown to lead to a reduction in liver fibrosis stage, progression to cirrhosis, liver stiffness and liver fat content (Loomba et al. The liver meeting 2016, Boston, Mass., November 11-15, American Association for the Study of Liver Diseases, 2016).

WO 2008/016131 discloses fused heterocyclic ASK1 inhibitors for use in the treatment of diabetes and inflammatory disease. WO 2004/048565 describes a novel peptide which has ASK1 activity which may be useful in the treatment of cancer and degenerative diseases. WO 2009/123986 and WO 2009/027283 both describe ASK1 inhibitors. WO 2008/075172 discloses nicotinamide derivatives as inhibitors of b-PGDS and their use for treating prostaglandin D2 mediated diseases, WO 2001/39777 discloses compounds specific to adenosine $A_1$ $A_{2a}$, and $A_3$ receptors. EP 2058309 discloses fused heterocyclic compounds.

The present invention describes a series of pyrrolopyrimidine derivatives which are inhibitors of the ASK1 kinase and which may be useful in the prophylaxis and/or treatment of pain, inflammatory conditions, cardiovascular diseases, neurodegenerative diseases, neurological diseases, complications of diabetes, cancer and/or fibrotic diseases.

SUMMARY OF THE INVENTION

The present invention is based on the identification of novel pyrrolopyrimidine and pyrrolopyridine compounds that may be useful for the prophylaxis and/or treatment of pain and/or fibrotic diseases. In a particular aspect, the present compounds are ASK inhibitors, particularly ASK1 inhibitors. The present invention also provides methods for the production of these compounds, pharmaceutical compositions comprising these compounds and the use of the compounds in the prophylaxis and/or treatment of pain, inflammatory conditions, cardiovascular diseases, neurodegenerative diseases, neurological diseases, complications of diabetes, cancer and/or fibrotic diseases.

Accordingly, in a first aspect of the invention, the compounds of the invention are provided having a Formula I:

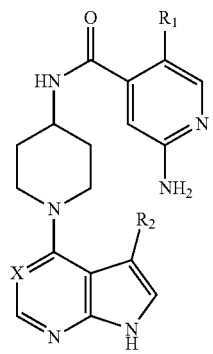

I wherein
$R^1$ is H, $CH_3$, F or Cl;
X is N, CH or C—CN; and
$R^2$ is $CH_3$ or halogen.

In a particular aspect, the compounds of the invention may exhibit selectivity towards the ASK kinase family, in particular towards ASK1. In a further particular aspect, the compounds of the invention may show low activity on other kinase enzymes, in particular JAK2. Such selectivity may result in improved drug safety and/or reduce off-target associated risks.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the prophylaxis and/or treatment of pain and/or fibrotic diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly pain and/or fibrotic diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of pain and/or fibrotic diseases.

In a particular aspect, the compounds of the invention are provided for use in the prophylaxis and/or treatment of pain.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Amino' refers to the radical —$NH_2$.

'Halo' or 'halogen' refers to fluoro (F), chloro (Cl), bromo (Br) and iodo (I). Particular halo groups are either fluoro or chloro.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset).

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'pain' refers to inflammatory pain, in particular chronic articular pain (e.g. rheumatoid arthritis, osteoarthritis, rheumatoid spondylitis, gouty arthritis (gout) and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea. More particularly, the term refers to chronic articular pain. More particularly the term refers to rheumatoid arthritis, osteoarthritis, and gouty arthritis (gout).

As used herein the term "cardiovascular disease(s)" refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; shock states associated with a marked drop in arterial pressure (e.g. endotoxic, surgical, traumatic shock or septic shock); pulmonary arterial hypertension (PAH), hypertension, valvular heart disease, heart failure, abnormal blood pressure; shock; vasoconstriction (including that associated with migraines); vascular abnormality, varicose therapy, insufficiency limited to a single organ or tissue, functional or organic venous insufficiency; cardiac hypertrophy, ventricular fibrosis, and myocardial remodelling. More particularly, the term refers to atherosclerosis, pulmonary arterial hypertension, heart failure, acute coronary syndrome, cardiac hypertrophy, ventricular fibrosis and myocardial remodeling.

As used herein the terms 'neuropathic pain' or 'syndromes involving neuropathic pain' include both central neuropathic pain and peripheral neuropathic pain unless the context dictates otherwise, the terms include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins, chemotherapy induced neuropathy or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold or mechanical hyperalgesia), continuing pain sensation after removal of the stimulation (hyperpathia) or an absence of or deficit in selective sensory pathways (hypoalgesia).

As used herein the term 'inflammatory condition(s)' refers to the group of conditions including, rheumatoid arthritis, osteoarthritis, juvenile idiopathic arthritis, psoriatic arthritis, ankylosing spondylitis, skin conditions (e.g. sunburn, burns, eczema, dermatitis, psoriasis), ophthalmic diseases (e.g. glaucoma, retinitis, retinopathies, uveitis and of acute injury to the eye tissue (e.g. conjunctivitis)), lung disorders (e.g. allergic airway disease (e.g. asthma, rhinitis), chronic obstructive pulmonary disease (COPD), bronchitis, emphysema, respiratory distress synfrom, pigeon fancier's disease and farmer's lung), gastrointestinal tract disorders (e.g inflammatory bowel diseases such as Crohn's disease or ulcerative colitis, aphthous ulcer, atopic gastritis, gastritis varialoforme, coeliac disease, regional ileitis, irritable bowel syndrome, gastrointestinal reflux disease, diarrhoea, and/or constipation), endotoxin-driven disease states (e.g. complications after bypass surgery or chronic endotoxin states contributing to e.g. chronic cardiac failure), organ transplantation and other conditions with an inflammatory component such as vascular disease, steatohepatitis, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, osteoarthritis, chronic obstructive pulmonary disease (COPD) and inflammatory bowel diseases.

As used herein the term 'asthma' refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'neurodegenerative diseases' refers to conditions resulting from or including neurodegeneration including dementia, particularly degenerative dementia (including senile dementia, Alzheimer's disease, Pick's disease, Huntingdon's chorea, Parkinson's disease and Creutzfeldt-Jakob disease, ALS and motor neuron disease); vascular dementia (including multi-infarct dementia); as well as dementia associated with intracranial space occupying lesions; trauma; infections and related conditions (including HIV infection); peripheral neuropathies, multiple sclerosis, retinopathies, glaucoma, macular degeneration, cerebral ischemia and traumatic brain injury and mild cognitive impairment associated with ageing, particularly Age Associated Memory Impairment.

As used herein the term 'complications of diabetes' refers to conditions which are associated with Type I or Type II diabetes, these conditions include those related to vascular or microvascular changes e.g. diabetic retinopathy, diabetic microangiopathy, diabetic nephropathy (also referred to as diabetic kidney disease (DKD)), macular degeneration, glaucoma, nephrotic syndrome, diabetic cardiomyopathy, aplastic anaemia, uveitis, Kawasaki disease and sarcoidosis; as well as disorders of fat metabolism which may be associated with diabetes or obesity for example hepatic steatosis. More particularly the term refers to diabetic retinopathy, diabetic microangiopathy, diabetic nephropathy and hepatic steatosis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor. In another particular embodiment, the term cancer refers to pancreatic cancer, liver cancer, hepatocellular carcinoma (HCC), breast cancer, or colon cancer. In particular, it refers to hepatocellular carcinoma, melanoma, gastric cancer, liposarcoma and cancers caused by oxidative stresses for example cervical spondylotic myelopathy.

As used herein the term 'fibrotic diseases' refers to diseases characterized by excessive scarring due to excessive production, deposition, and contraction of extracellular matrix, and those that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug induced fibrosis, occupational and/or environmental induced fibrosis, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky Pudlak syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitial fibrosis; glomerular nephritis; focal segmental glomerular sclerosis; IgA nephropathy; hypertension; Alport syndrome; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Dupuytren's disease, keloids, cutaneous fibrosis; cutaneous scleroderma; systemic sclerosis, spinal cord injury/fibrosis; myelofibrosis; vascular restenosis; atherosclerosis; arteriosclerosis; Wegener's granulomatosis; Peyronie's disease, or chronic lymphocytic. In a particular embodiment the fibrotic disease is of an individual organ or tissue such as liver fibrosis, lung fibrosis or kidney fibrosis. In a particular embodiment, the fibrotic disease is selected from idiopathic pulmonary fibrosis (IPF), diabetic kidney disease (DKD) and nonalcoholic steatohepatitis (NASH).

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

FIGURES

Figure 1:
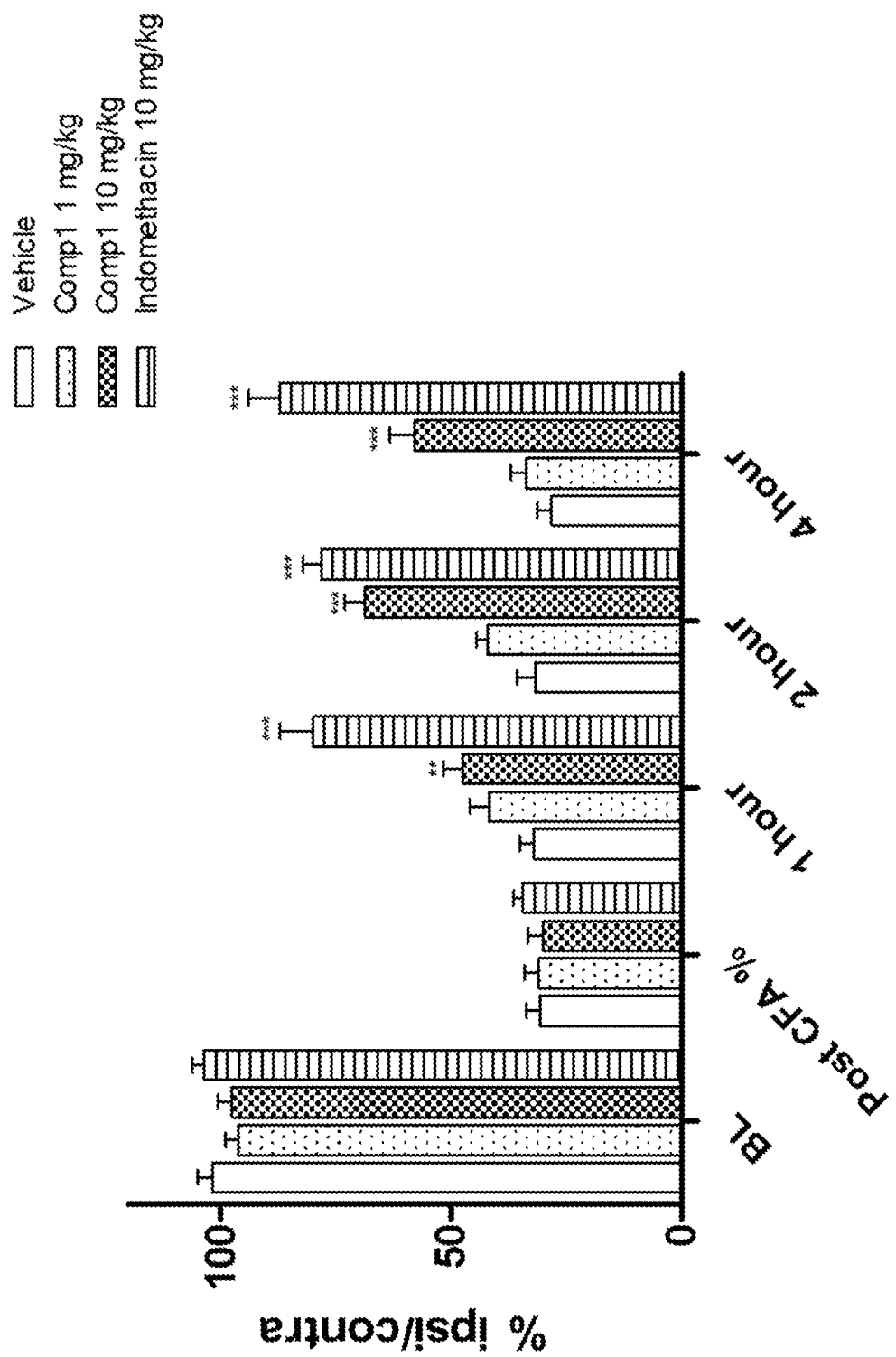
FIG. 1 shows the effect of Compound 1 at two different doses given p.o. on the CFA-induced hyperalgesia in the rat model of Example 3.1.
Figure 2:
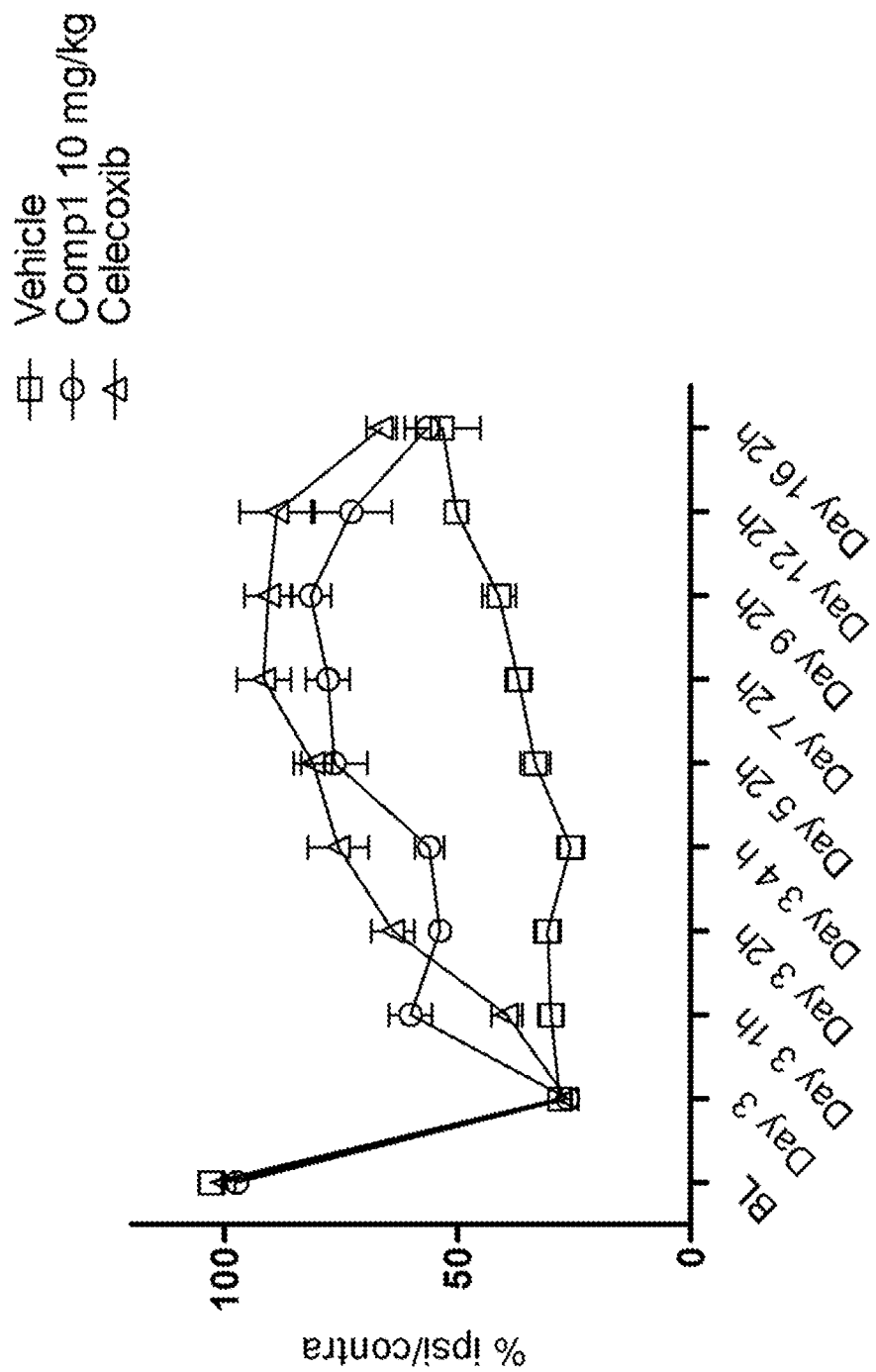
FIG. 2 shows the effect of Compound 1 at 10 mg/kg given p.o. on MIA-induced hyperalgesia in the rat model of Example 3.2.
Figure 3:
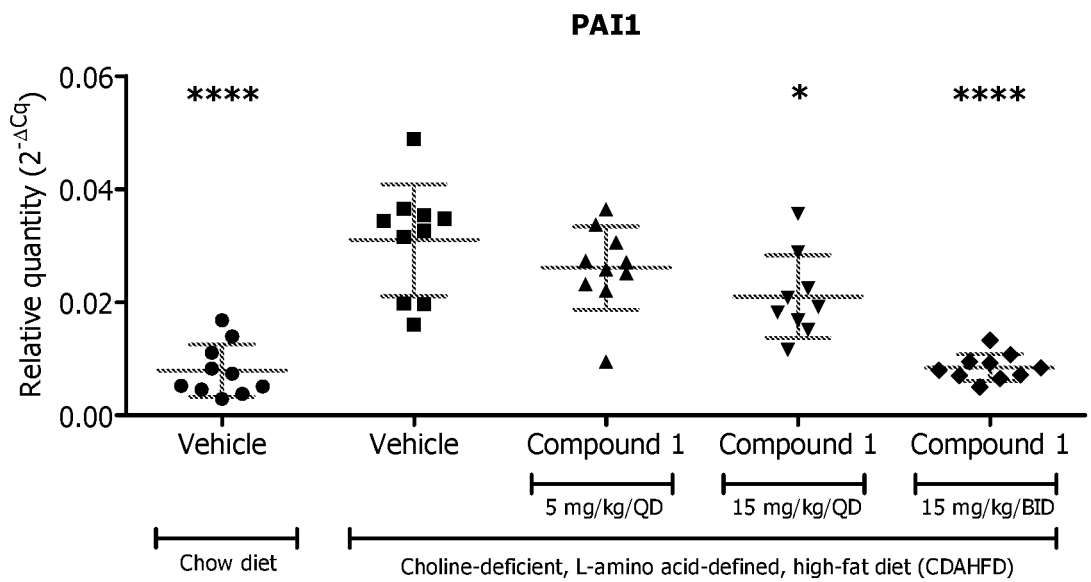
Figure 3:
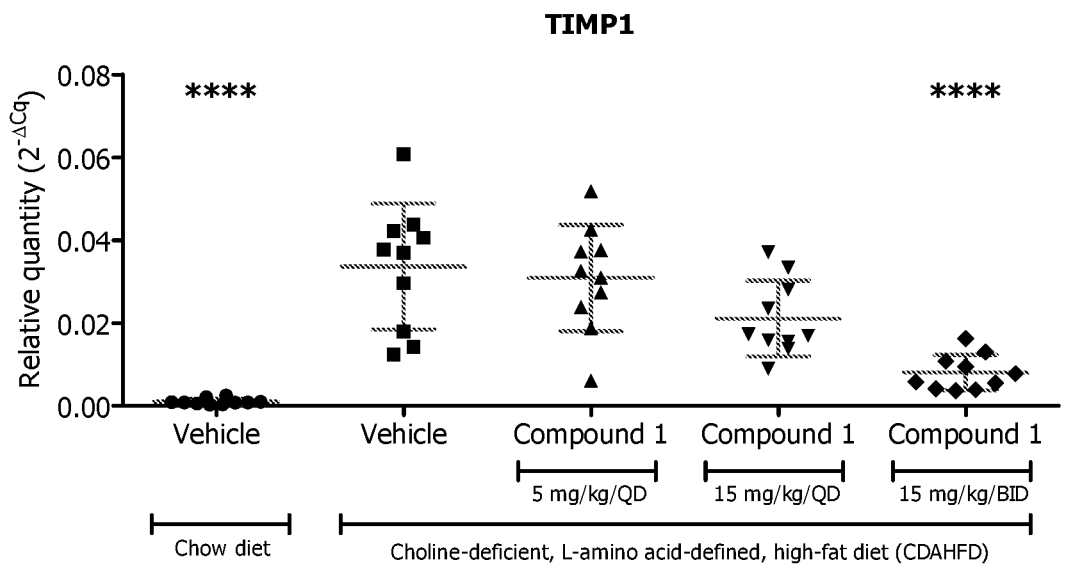

FIG. 3 shows the effect of Compound 1 at 5 mg/kg/QD, 15 mg/kg/QD and 15 mg/kg/BID on the expression levels of a panel of fibrosis related genes in mouse liver samples from the CFAHFD model of fibrosis (Example 3.10). FIG. 3A: PAI1, FIG. 3B: TIMP1, FIG. 3C: COL1A1, FIG. 3D: CTGF, FIG. 3E: ACTA2 and FIG. 3F: TGFβ Data are from day 73 and are presented as mean±SEM, *$p<0.05$, $p<0.01$, *$p<0.001$, ****$P<0.0001$ vs CDAHFD diet+vehicle, Mann-Whitney test.

Figure 4:
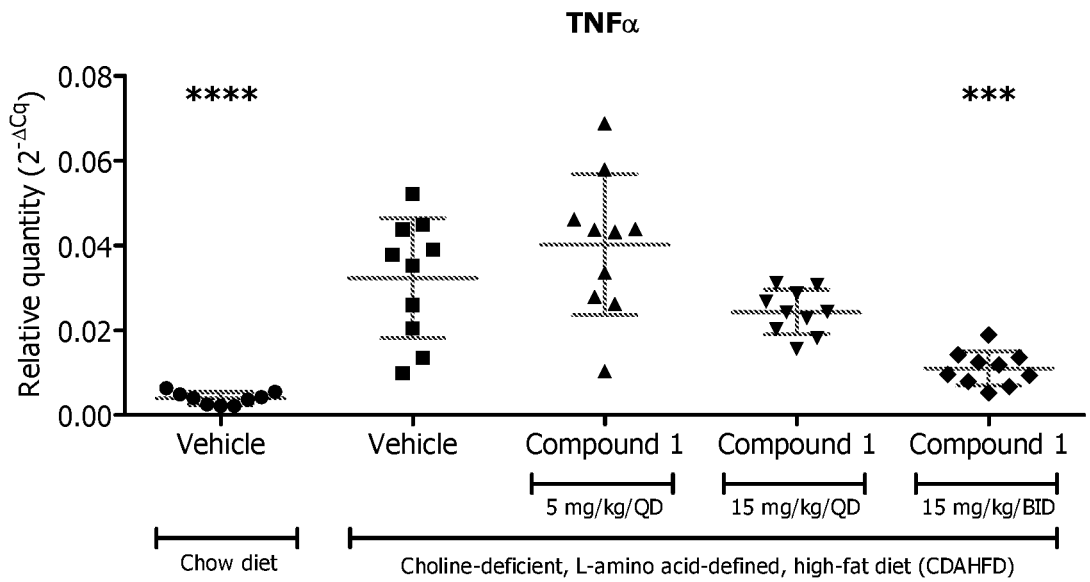
Figure 4:
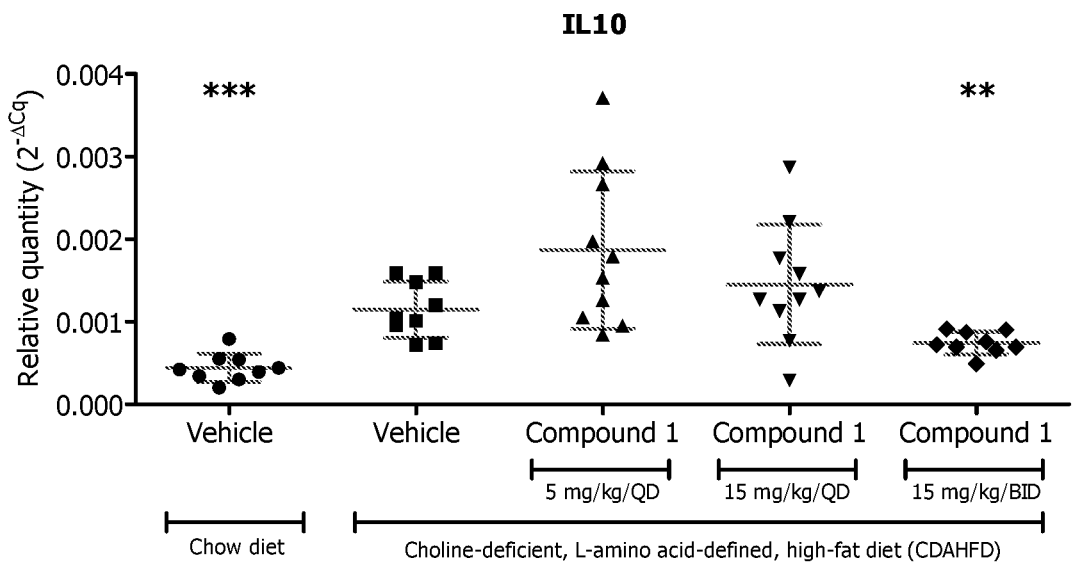

FIG. 4 shows the effect of Compound 1 at 5 mg/kg/QD, 15 mg/kg/QD and 15 mg/kg/BID on the expression levels of a panel of inflammation related genes in mouse liver samples from the CFAHFD model of fibrosis (Example 3.10). FIG. 4A: TNFα, FIG. 4B: IL10, and FIG. 4C: CCL2. Data are from day 73 and are presented as mean±SEM, *$p<0.05$, $p<0.01$, *$p<0.001$, ****$P<0.0001$ vs CDAHFD diet+vehicle, Mann-Whitney test.

Figure 5:
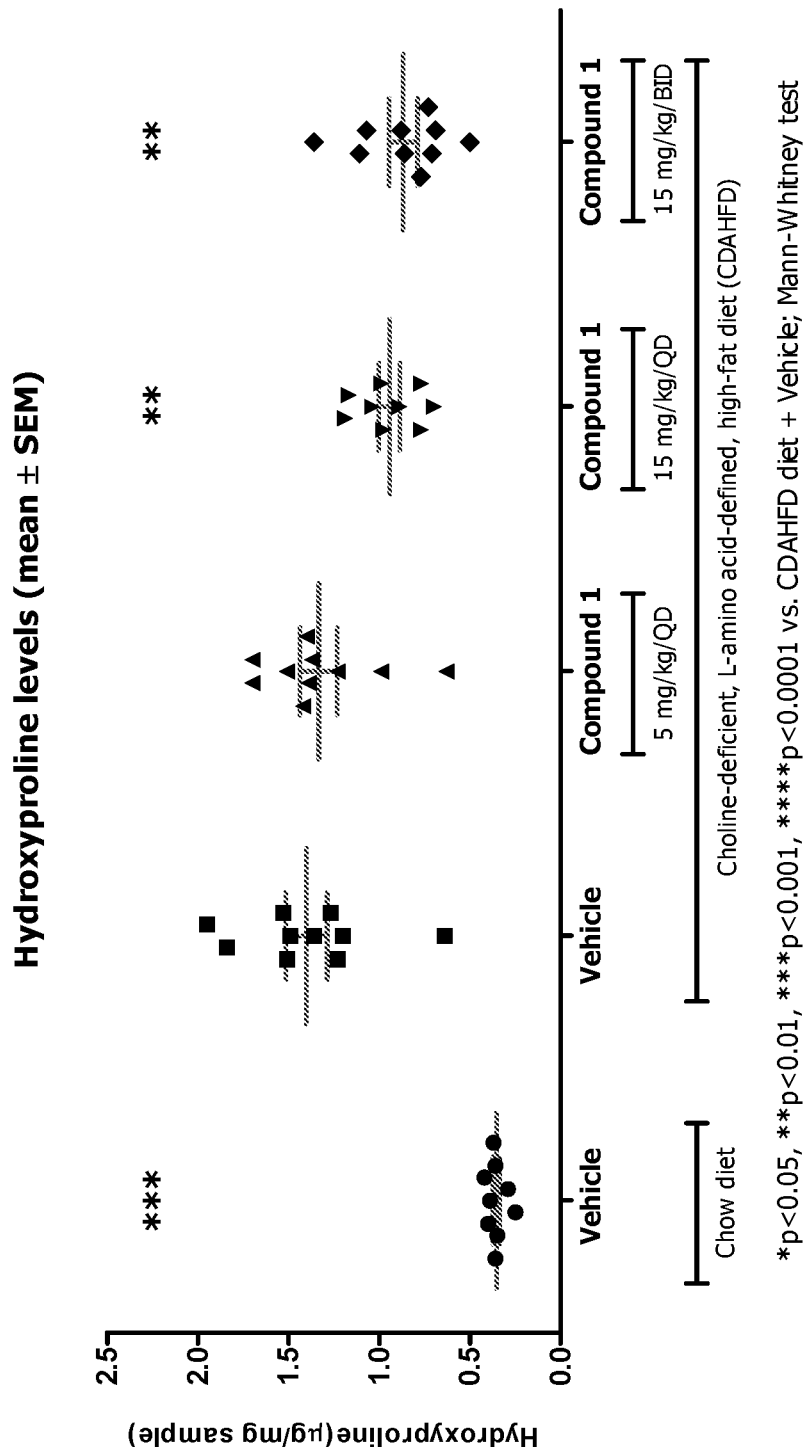

FIG. 5 shows the effect of Compound 1 at 5 mg/kg/QD, 15 mg/kg/QD and 15 mg/kg/BID on hydroxyproline levels mouse liver tissue from the CFAHFD model of fibrosis (Example 3.10). Data are from day 73 and are presented as mean±SEM, *$p<0.05$, $p<0.01$, *$p<0.001$, ****$P<0.0001$ vs CDAHFD diet+vehicle, Mann-Whitney test.

Figure 6:
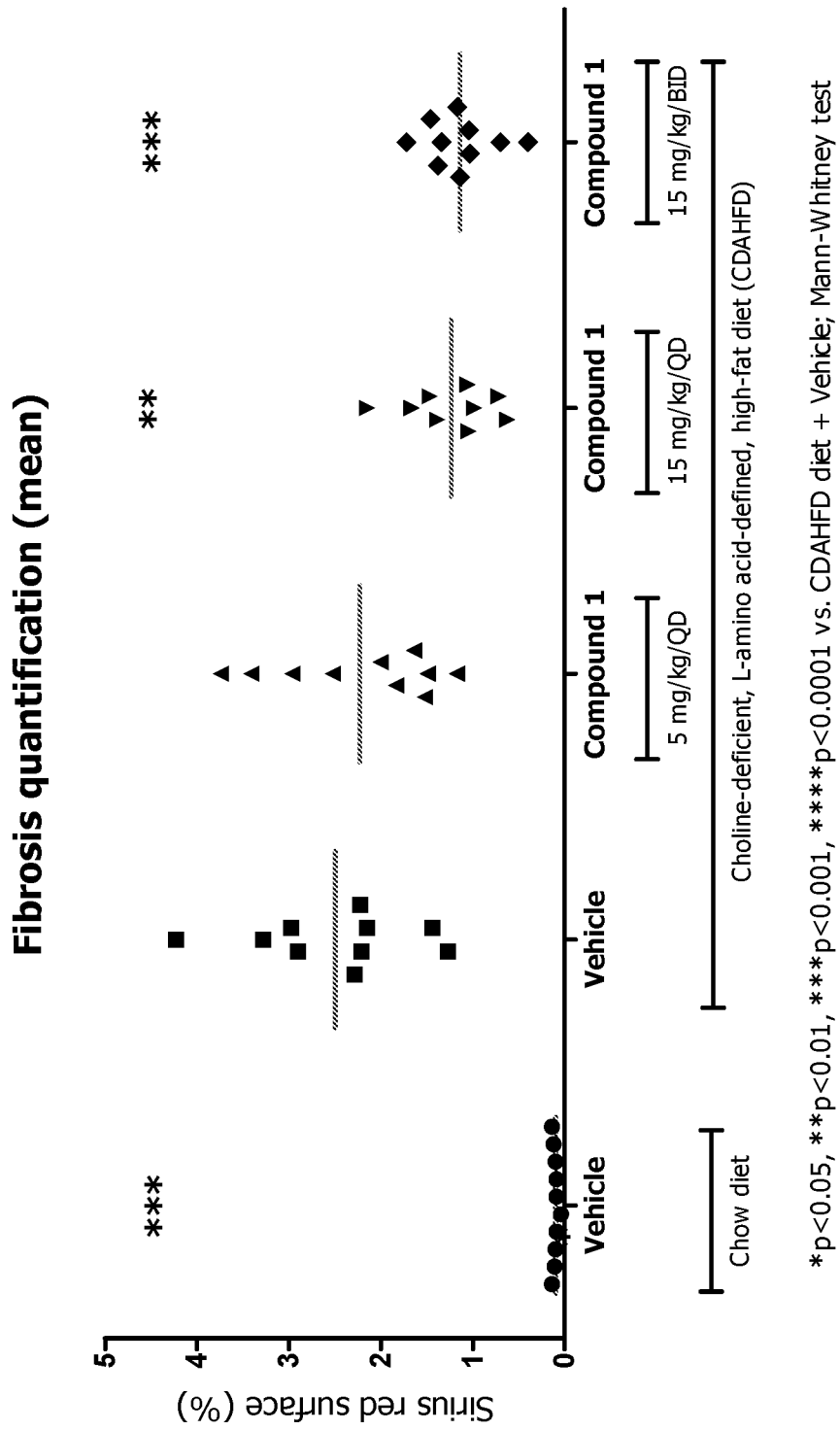

FIG. 6 shows the effect of Compound 1 at 5 mg/kg/QD, 15 mg/kg/QD and 15 mg/kg/BID using Sirius red fibrosis quantification from the CFAHFD model of fibrosis (Example 3.10). Data are from day 73 and are presented as mean±SEM, *p<0.05, p<0.01, *p<0.001, ****P<0.0001 vs CDAHFD diet+vehicle, Mann-Whitney test.

Figure 7:
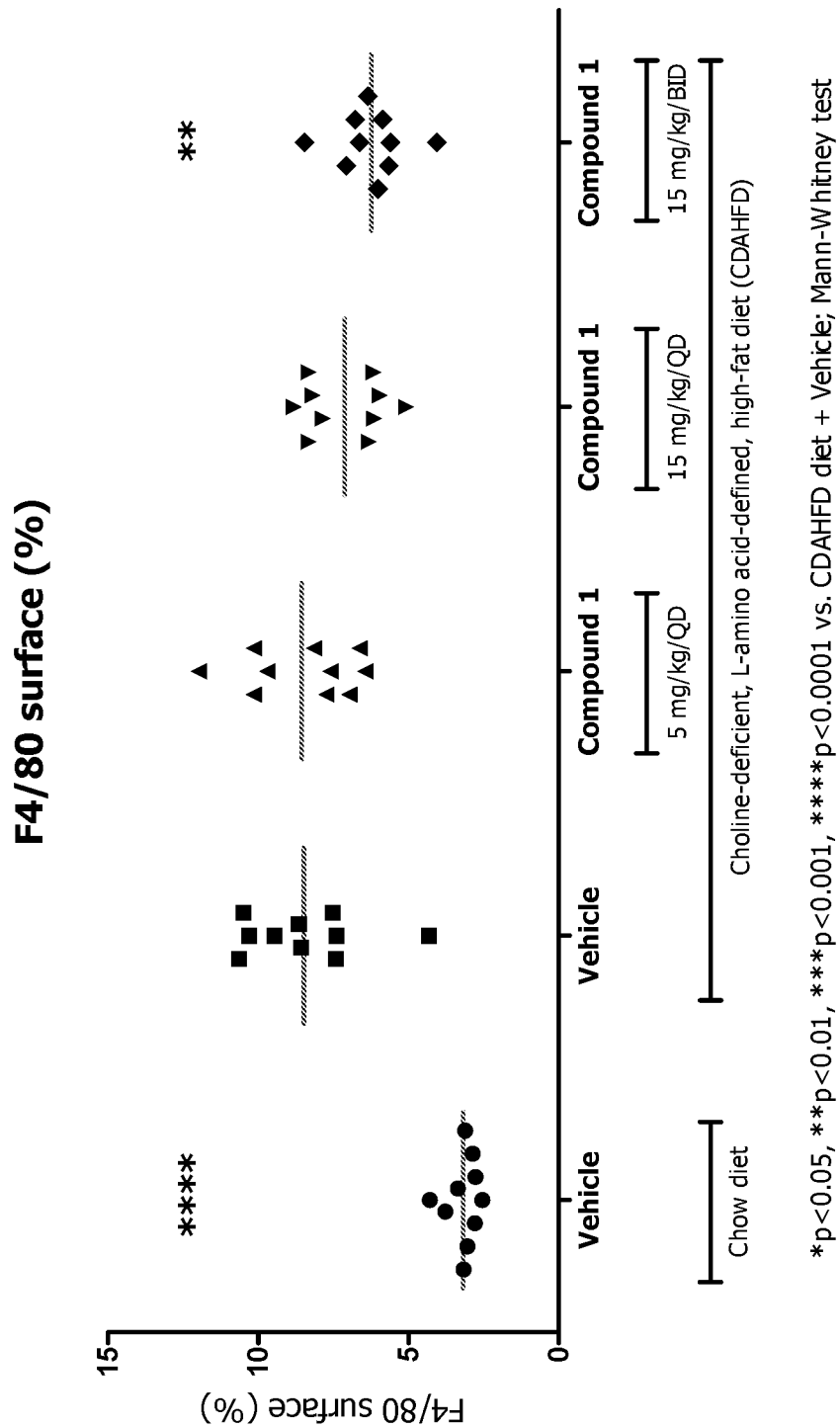

FIG. 7 shows the effect of Compound 1 at 5 mg/kg/QD, 15 mg/kg/QD and 15 mg/kg/BID on F4/80 quantification from the CFAHFD model of fibrosis (Example 3.10). Data are from day 73 and are presented as mean±SEM, *p<0.05, p<0.01, *p<0.001, ****P<0.0001 vs CDAHFD diet+vehicle, Mann-Whitney test.

THE INVENTION

The present invention is based on the identification of novel pyrrolopyrimidine and pyrrolopyridine compounds that may be useful for the prophylaxis and/or treatment of pain, inflammatory conditions, cardiovascular diseases, neurodegenerative diseases, neurological diseases, complications of diabetes, cancer and/or fibrotic diseases. In a particular aspect, the present compounds are ASK inhibitors, particularly ASK1 inhibitors.

The present invention also provides methods for the production of these compounds, pharmaceutical compositions comprising these compounds and methods for treating pain, inflammatory conditions, cardiovascular diseases, neurodegenerative diseases, neurological diseases, complications of diabetes, cancer and/or fibrotic diseases by administering the compounds of the invention.

Accordingly, in a first aspect of the invention, the compounds of the invention are provided having a Formula I:

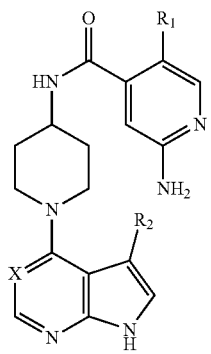

I wherein
$R^1$ is H, $CH_3$, F or Cl;
X is N, CH or C—CN; and
$R^2$ is $CH_3$ or halogen.

In one embodiment $R^1$ is F.

In one embodiment $R^1$ is F and $R^2$ is $CH_3$.

In one embodiment, X is CH. In an alternative embodiment X is C—CN. In an alternative embodiment X is N.

In one embodiment, X is N and $R^1$ is F. In a particular embodiment, X is N, $R^1$ is F and $R^2$ is $CH_3$. In a further embodiment, $R^2$ is $CH_3$ or Cl. In a yet further embodiment, $R^2$ is $CH_3$.

In one embodiment, a compound of the invention is selected from:
2-amino-5-fluoro-N-[1-(5-methyl-7H-pyrrolo[2,3-d]pyrimidin-4-yl)-4-piperidyl]pyridine-4-carboxamide (Compound 1),
2-amino-5-methyl-N-[1-(5-methyl-7H-pyrrolo[2,3-d]pyrimidin-4-yl)-4-piperidyl]pyridine-4-carboxamide (Compound 2),
2-amino-5-chloro-N-[1-(5-methyl-7H-pyrrolo[2,3-d]pyrimidin-4-yl)-4-piperidyl]-pyridine-4-carboxamide (Compound 3),
2-amino-N-[1-(5-chloro-7H-pyrrolo[2,3-d]pyrimidin-4-yl)-4-piperidyl]pyridine-4-carboxamide (Compound 4),
2-amino-N-[1-(5-chloro-7H-pyrrolo[2,3-d]pyrimidin-4-yl)-4-piperidyl]-5-fluoro-pyridine-4-carboxamide (Compound 5),
2-amino-N-[1-(5-cyano-3-methyl-1H-pyrrolo[2,3-b]pyridin-4-yl)-4-piperidyl]-5-fluoro-pyridine-4-carboxamide (Compound 6), and
2-amino-N-[1-(3-chloro-1H-pyrrolo[2,3-b]pyridin-4-yl)-4-piperidyl]-5-fluoro-pyridine-4-carboxamide (Compound 7).

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

In a specific embodiment, a compound of the invention according to any one of the embodiments herein displays an improved activity in an in vitro cellular assay for ASK1 activity as compared to structurally similar compounds. In a particular embodiment a compound of the invention displays an improved activity in the cellular assay for ASK1 activity in peripheral blood mononuclear cells (PBMCs) as described herein as Example 2.3.

In an alternative embodiment, a compound of the invention according to any one of the embodiments herein may show a decreased induction of Cyp activity. In particular, a compound of the invention may show a decreased induction of Cyp3A4 activity as compared to structurally similar compounds.

In an alternative embodiment, a compound of the invention according to any one of the embodiments herein may show a decreased inhibition of Cyp activity. In particular, a compound of the invention may show a decreased inhibition of Cyp3A4 activity as compared to structurally similar compounds. More particularly, a compound of the invention may show an $IC_{50}$ for Cyp inhibition of >10 μM.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above.

Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$-$C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of pain, inflammatory conditions, cardiovascular diseases, neurodegenerative diseases, neurological diseases, complications of diabetes, cancer and/or fibrotic diseases.

In another embodiment, the present invention provides compounds of the invention, or pharmaceutical compositions comprising a compound of the invention for use in the manufacture of a medicament for use in the prophylaxis and/or treatment of pain, inflammatory conditions, cardiovascular diseases, neurodegenerative diseases, neurological diseases, complications of diabetes, cancer and/or fibrotic diseases.

In one embodiment, the present invention provides pharmaceutical compositions comprising a compound of the invention, and another therapeutic agent. In a particular embodiment, the other therapeutic agent is an agent for the prophylaxis and/or treatment of pain, inflammatory conditions, cardiovascular diseases, neurodegenerative diseases, neurological diseases, complications of diabetes, cancer and/or fibrotic diseases.

In additional method of treatment aspects, this invention provides methods of prophylaxis and/or treatment of pain, inflammatory conditions, cardiovascular diseases, neurodegenerative diseases, neurological diseases, complications of diabetes, cancer and/or fibrotic diseases, which methods comprise the administration of an effective amount of a compound of the invention or one or more of the pharmaceutical compositions herein described for the treatment or prophylaxis of said condition.

In additional method of treatment aspects, this invention provides methods of prophylaxis and/or treatment of a mammal afflicted with pain, inflammatory conditions, cardiovascular diseases, neurodegenerative diseases, neurological diseases, complications of diabetes, cancer and/or fibrotic diseases, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of pain. In a particular embodiment, the pain is selected from chronic articular pain. In a specific embodiment the chronic articular pain is the pain of osteoarthritis, rheumatoid arthritis, rheumatoid spondylitis, gouty arthritis (gout) and/or juvenile arthritis.

In another embodiment, the present invention provides compounds of the invention, or pharmaceutical compositions comprising a compound of the invention for use in the manufacture of a medicament for use in the prophylaxis and/or treatment of pain. In a particular embodiment, the pain is selected from chronic articular pain. In a specific embodiment the chronic articular pain is the pain of osteoarthritis, rheumatoid arthritis, rheumatoid spondylitis, gouty arthritis (gout) and/or juvenile arthritis.

In additional method of treatment aspects, this invention provides methods of prophylaxis and/or treatment of a mammal afflicted with pain, which methods comprise the administration of an effective amount of a compound of the invention or one or more of the pharmaceutical compositions herein described for the treatment or prophylaxis of said condition. In a particular embodiment, the pain is selected from chronic articular pain. In a specific embodiment the chronic articular pain is the pain of osteoarthritis, rheumatoid arthritis, rheumatoid spondylitis, gouty arthritis (gout) and/or juvenile arthritis.

In one embodiment, the present invention provides compounds of the invention or pharmaceutical compositions comprising a compound of the invention, for use in the prophylaxis and/or treatment of inflammatory conditions. In a particular embodiment, the inflammatory condition is selected from rheumatoid arthritis, osteoarthritis, chronic obstructive pulmonary disease (COPD) and inflammatory bowel diseases. More particularly, the inflammatory condition is osteoarthritis.

In another embodiment, the present invention provides compounds of the invention, or pharmaceutical compositions comprising a compound of the invention for use in the manufacture of a medicament for use in the prophylaxis and/or treatment of inflammatory conditions. In a particular embodiment, the inflammatory condition is selected from rheumatoid arthritis, osteoarthritis, chronic obstructive pulmonary disease (COPD) and inflammatory bowel diseases. More particularly, the inflammatory condition is osteoarthritis.

In additional method of treatment aspects, this invention provides methods of prophylaxis and/or treatment of a mammal afflicted with inflammatory conditions, which methods comprise the administration of an effective amount of a compound of the invention or one or more of the pharmaceutical compositions herein described for the treatment or prophylaxis of said condition. In a particular embodiment, the inflammatory condition is selected from rheumatoid arthritis, osteoarthritis, chronic obstructive pulmonary disease (COPD) and inflammatory bowel diseases. More particularly, the inflammatory condition is osteoarthritis.

In one embodiment, the present invention provides compounds of the invention or pharmaceutical compositions comprising a compound of the invention, for use in the prophylaxis and/or treatment of cardiovascular diseases. In a particular embodiment, the cardiovascular disease is selected from atherosclerosis, pulmonary arterial hypertension, heart failure, acute coronary syndrome, cardiac hypertrophy, ventricular fibrosis and myocardial remodeling.

In another embodiment, the present invention provides compounds of the invention, or pharmaceutical compositions comprising a compound of the invention for use in the manufacture of a medicament for use in the prophylaxis and/or treatment of cardiovascular diseases. In a particular embodiment, the cardiovascular disease is selected from atherosclerosis, pulmonary arterial hypertension, heart failure, acute coronary syndrome, cardiac hypertrophy, ventricular fibrosis and myocardial remodeling.

In additional method of treatment aspects, this invention provides methods of prophylaxis and/or treatment of a mammal afflicted with a cardiovascular disease, which methods comprise the administration of an effective amount of a compound of the invention or one or more of the pharmaceutical compositions herein described for the treatment or prophylaxis of said disease. In a particular embodiment, the cardiovascular disease is selected from atherosclerosis, pulmonary arterial hypertension, heart failure, acute coronary syndrome, cardiac hypertrophy, ventricular fibrosis and myocardial remodeling.

In one embodiment, the present invention provides compounds of the invention or pharmaceutical compositions comprising a compound of the invention, for use in the prophylaxis and/or treatment of neurodegenerative diseases. In a particular embodiment, the neurodegenerative disease is selected from degenerative dementia, Alzheimer's disease, multiple sclerosis and retinopathies.

In another embodiment, the present invention provides compounds of the invention, or pharmaceutical compositions comprising a compound of the invention for use in the manufacture of a medicament for use in the prophylaxis and/or treatment of neurodegenerative diseases. In a particular embodiment, the neurodegenerative disease is selected from degenerative dementia, Alzheimer's disease, multiple sclerosis and retinopathies.

In additional method of treatment aspects, this invention provides methods of prophylaxis and/or treatment of a mammal afflicted with a neurodegenerative disease, which methods comprise the administration of an effective amount of a compound of the invention or one or more of the pharmaceutical compositions herein described for the treatment or prophylaxis of said disease. In a particular embodiment, the neurodegenerative disease is selected from degenerative dementia, Alzheimer's disease, multiple sclerosis and retinopathies.

In one embodiment, the present invention provides compounds of the invention or pharmaceutical compositions comprising a compound of the invention, for use in the prophylaxis and/or treatment of neurological diseases. In a particular embodiment, the neurological disease is selected from neuropathic pain, dementia, multiple sclerosis and retinopathies.

In another embodiment, the present invention provides compounds of the invention, or pharmaceutical compositions comprising a compound of the invention for use in the manufacture of a medicament for use in the prophylaxis and/or treatment of neurological diseases. In a particular embodiment, the neurological disease is selected from neuropathic pain, dementia, multiple sclerosis and retinopathies.

In additional method of treatment aspects, this invention provides methods of prophylaxis and/or treatment of a mammal afflicted with a neurological disease, which methods comprise the administration of an effective amount of a compound of the invention or one or more of the pharmaceutical compositions herein described for the treatment or prophylaxis of said disease. In a particular embodiment, the neurological disease is selected from neuropathic pain, dementia, multiple sclerosis and retinopathies.

In one embodiment, the present invention provides compounds of the invention or pharmaceutical compositions comprising a compound of the invention, for use in the prophylaxis and/or treatment of complications of diabetes. In a particular embodiment, the complication is selected from diabetic retinopathy, diabetic microangiopathy, diabetic nephropathy and hepatic steatosis.

In another embodiment, the present invention provides compounds of the invention, or pharmaceutical compositions comprising a compound of the invention for use in the manufacture of a medicament for use in the prophylaxis and/or treatment of complications of diabetes. In a particular embodiment, the complication is selected from diabetic retinopathy, diabetic microangiopathy, diabetic nephropathy and hepatic steatosis.

In additional method of treatment aspects, this invention provides methods of prophylaxis and/or treatment of a mammal afflicted with complications of diabetes, which methods comprise the administration of an effective amount of a compound of the invention or one or more of the pharmaceutical compositions herein described for the treatment or prophylaxis of said complication. In a particular embodiment, the complication is selected from diabetic retinopathy, diabetic microangiopathy, diabetic nephropathy and hepatic steatosis.

In one embodiment, the present invention provides compounds of the invention or pharmaceutical compositions comprising a compound of the invention, for use in the prophylaxis and/or treatment of cancer.

In another embodiment, the present invention provides compounds of the invention, or pharmaceutical compositions comprising a compound of the invention for use in the manufacture of a medicament for use in the prophylaxis and/or treatment of cancer.

In additional method of treatment aspects, this invention provides methods of prophylaxis and/or treatment of a mammal afflicted with cancer, which methods comprise the administration of an effective amount of a compound of the invention or one or more of the pharmaceutical compositions herein described for the treatment or prophylaxis of said cancer.

In one embodiment, the present invention provides compounds of the invention or pharmaceutical compositions comprising a compound of the invention, for use in the prophylaxis and/or treatment of fibrotic diseases. In a particular embodiment the fibrotic disease is of an individual organ or tissue such as liver fibrosis, lung fibrosis or kidney fibrosis. In a particular embodiment, the fibrotic disease is selected from idiopathic pulmonary fibrosis (IPF), diabetic kidney disease (DKD) and nonalcoholic steatohepatitis (NASH).

In another embodiment, the present invention provides compounds of the invention, or pharmaceutical compositions comprising a compound of the invention for use in the manufacture of a medicament for use in the prophylaxis and/or treatment of fibrotic diseases. In a particular embodiment the fibrotic disease is of an individual organ or tissue such as liver fibrosis, lung fibrosis or kidney fibrosis. In a particular embodiment, the fibrotic disease is selected from idiopathic pulmonary fibrosis (IPF), diabetic kidney disease (DKD) and nonalcoholic steatohepatitis (NASH).

In additional method of treatment aspects, this invention provides methods of prophylaxis and/or treatment of a mammal afflicted with a fibrotic disease, which methods comprise the administration of an effective amount of a compound of the invention or one or more of the pharmaceutical compositions herein described for the treatment or prophylaxis of said disease. In a particular embodiment the fibrotic disease is of an individual organ or tissue such as liver fibrosis, lung fibrosis or kidney fibrosis. In a particular embodiment, the fibrotic disease is selected from idiopathic pulmonary fibrosis (IPF), diabetic kidney disease (DKD) and nonalcoholic steatohepatitis (NASH).

Injection dose levels range from about 0.1 mg/kg/h to at least 10 mg/kg/h, or from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds of the invention that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of an inflammatory condition, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic disease-modifying antirheumatic drugs (DMARDS), (for example but without limitation methotrexate, leflunomide, sulfasalazine, Auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

According to a further aspect of the present invention there is provided a process for the preparation of compounds of formula I. The schemes herein are examples of synthetic schemes that may be used to synthesise the compounds of the invention. In the schemes herein, reactive groups can be protected with protecting groups and de-protected according to well established techniques.

According to a further aspect of the invention there is provided a process for preparing a compound of formula I as herein defined which comprises:
(a) reacting a compound of formula II:

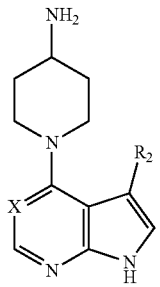

II wherein X and R$_2$ are as defined herein, with a compound of formula III:

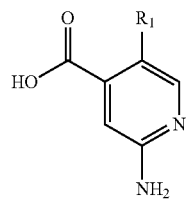

III or a protected derivative thereof, wherein R$^1$ is as defined herein;
(b) deprotection of a protected derivative of a compound of formula I;
(c) interconversion of a compound of formula I or protected derivative thereof to a further compound of formula I or protected derivative thereof; and
(d) optional formation of a pharmaceutically acceptable salt of a compound of formula I.

Compounds of formulae II and III may be prepared in accordance with procedures described herein in Schemes 1A, 1B, 1C and the procedures for preparing Compounds 1 to 7.

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art.

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 µm). Thin layer chromatography is carried out using pre-coated silica gel 60F-254 plates (thickness 0.25 mm). NMR spectra are recorded on Bruker DPX 300 MHz equipped with a 5 mm BBI probe, Bruker AV400 MHz equipped with a 5 mm PABBO probe, Bruker DRX 500 MHz equipped with a 5 mm PABBI probe and Bruker Avance III 600 spectrometer equipped with a 5 mm RT BBI probe. The samples are recorded at 25° C. using DMSO-d$_6$ or CDCl$_3$ as a solvent, unless otherwise stated. Chemical shifts (δ) for $^1$H NMR spectra are reported in parts per million (ppm) relative to tetramethylsilane (δ 0.00) as internal reference.

Electrospray MS spectra are obtained on Waters Acquity UPLC with Waters Acquity PDA detector and SQD mass spectrometer. Columns used: UPLC BEH C18 1.7 µm, 2.1×5 mm VanGuard Pre-column with Acquity UPLC BEH C18 1.7 µm, 2.1×50 mm Column or Acquity UPLC CSH C18 1.7 µm, 2.1×50 mm Column. All the methods are using MeCN/H$_2$O gradients. MeCN and H$_2$O contains either 0.1% Formic Acid or 10 mM NH$_4$HCO$_3$.

For preparative purification HPLC Waters Mass Directed Autopurification System is used. The system is composed of Waters Sample Manager 2767, Waters System Fluid Organizer, Waters Binary Gradient Module 2545, Waters 515 HPLC Pump, Waters Photodiode Array Detector 2998 and Waters Micromass ZQ MS detector. Software used: FractionLynx and MassLynx v4.1. General HPLC method parameters: gradient mobile phase of 0.1% formic acid in H$_2$O and MeCN or 10 mM NH$_4$HCO$_3$ pH=10 and MeCN. Column XBridge 30×150 mm, 5 µm. PDA detector settings: wavelength: 210-400 nm, resolution: 1.2 nm, sampling rate: 1.0 points/sec, filter response: 1. Microwave heating is performed with a Biotage Initiator.

List of Abbreviations Used in the Experimental Section

| Abbreviation | Definition |
| --- | --- |
| µL | microliter |
| AUC | Area Under the Curve |
| BAL | Broncho-alveolar lavage |
| BALF | Broncho-alveolar lavage fluid |
| BINAP | 2,2'-Bis(diphenylphosphino)-1,1'-binaphthalene |
| br. d | Broad doublet |
| Boc | tert-Butyloxy-carbonyl |
| br. s | Broad singlet |
| BSA | Bovine serum albumine |

-continued

| Abbreviation | Definition |
| --- | --- |
| br. t | Broad triplet |
| Cat. | Catalytic amount |
| cDNA | copy deoxyribonucleic acid |
| Cpd | Compound |
| d | doublet |
| DavePhos | 2-Dicyclohexylphosphino-2'-(N,N-dimethylamino)biphenyl |
| DCM | Dichloromethane |
| DEAD | diethyl azodicarboxylate |
| DIPE | Diisopropylether |
| DIPEA | N,N-diisopropylethylamine |
| DMA | Dimethylacetamide |
| DMAP | 4-Dimethylaminopyridine |
| DME | Dimethoxyethane |
| DMF | N,N-dimethylformamide |
| DMPU | 1,3-Dimethyl-3,4,5,6-tetrahydro-2(1H)-pyrimidinone |
| DMSO | Dimethylsulfoxide |
| dppf | 1,1'-Bis(diphenylphosphino) ferrocene |
| EDC | 1-ethyl-3-(3-dimethylaminopropyl)carbodiimide) |
| EDC•HCl | N-(3-Dimethylaminopropyl)-N'-ethylcarbodiimide hydrochloride |
| eq. | Equivalent |
| $Et_2O$ | Diethyl ether |
| EtOAc | Ethyl acetate |
| EtOH | Ethanol |
| FBS | Fetal bovine serum |
| FITC | Fluorescein Isothiocyanate |
| g | gram |
| h | hour |
| HATU | O-(7-azabenzotriazol-1-yl)-N,N,N',N'-tetramethyluronium hexafluorophosphate |
| HOBt | Hydroxybenzotriazole |
| HPLC | High pressure liquid chromatography |
| HRP | horseradish peroxydase |
| Int | Intermediate |
| JohnPhos | (2-Biphenyl)di-tert-butylphosphine |
| kg | kilogram |
| L | liter |
| LCMS | Liquid Chromatography- Mass Spectrometry |
| LDA | Lithium diisopropylamide |
| LiHMMDS | Lithium bis(trimethylsilyl)amide |
| m | multiplet |
| m-CPBA | 3-Chloroperbenzoic acid |
| MeCN | Acetonitrile |
| MEK | Methyl ethyl ketone |
| MeOH | Methanol |
| mg | milligram |
| min | minute |
| mL | millilitre |
| mmol | millimoles |
| MMP | Matrix Metallo Proteinase |
| Ms'd | Mass measured by LC-MS |
| Mtd | Method |
| MW | Molecular weight |
| N.A. | Not available |
| nBuOH | n-Butanol |
| Nva | Norvaline |
| NMR | Nuclear Magnetic Resonance |
| PBF | phosphate buffered formalin |
| PBS | Phosphate buffered saline |
| PCR | Polymerase chain reaction |
| $Pd(PPh_3)_4$ | Tetrakis(triphenylphosphine)palladium(0) |
| Pd/C | Palladium on Carbon 10% |
| $Pd_2(dba)_3$ | Tris(dibenzylideneacetone) dipalladium(0) |
| $PdCl_2dppf$ | [1,1'-Bis(diphenylphosphino)ferrocene] dichloropalladium(II) |
| $PdCl_2[P(o-Tol)_3]_2$ | Dichlorobis(tri-o-tolylphosphine)palladium(II) |
| $Pd(OAc)_2$ | Palladium(II) acetate |
| PEG | Polyethylene glycol |
| PEPPSI™-IPr | [1,3-Bis(2,6-Diisopropylphenyl)imidazol-2-ylidene](3-chloropyridvl)palladium(II) dichloride |
| ppm | part-per-million |
| q | quadruplet |
| QrtPCR | quantitative real-time PCR |
| QTL | quantitative trait loci |
| r.t. | room temperature |
| RNA | Ribonucleic acid |
| Rt | retention time |
| RuPhos | 2-Dicyclohexylphosphino-2',6'-diisopropoxybiphenyl |
| s | singlet |

| Abbreviation | Definition |
|---|---|
| sept | septuplet |
| SFC | Supercritical fluid chromatography |
| SM | Starting Material |
| Ster | Stereochemistry |
| t | triplet |
| TBAF | Tetra-n-butylammonium fluoride |
| t-BuOH | Tert-butanol |
| TBDPSCl | Tert-butyldiphenylsilyl chloride |

Mass-Directed Automated HPLC

Where applicable, purification by mass-directed automated HPLC was carried out using the following apparatus and conditions:

Hardware:
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector Software: Waters MassLynx version 4 SP2
Column: the columns used were Waters Atlantis, the dimensions of which are 19 mm×100 mm (small scale) and 30 mm×100 mm (large scale). The stationary phase particle size is 5 μm.

Acidic Method:
Solvents:
A: Aqueous solvent=Water+0.1% Formic Acid
B: Organic solvent=Acetonitrile+0.1% Formic Acid
Make up solvent=Methanol: Water 80:20
Needle rinse solvent=Methanol Methods:
There were five methods used depending on the analytical retention time of the compound of interest. Each had a 13.5-minute runtime, which comprised a 10-minute gradient followed by a 3.5 minute column flush and re-equilibration step.
Large/Small Scale 1.0-1.5 (HPLC), 0.4-0.6 (UPLC)=5-30% B
Large/Small Scale 1.5-2.2 (HPLC), 0.6-0.9 (UPLC)=15-55% B
Large/Small Scale 2.2-2.9 (HPLC), 0.9-1.2 (UPLC)=30-85% B
Large/Small Scale 2.9-3.6 (HPLC), 1.2-1.4 (UPLC)=50-99% B
Large/Small Scale 3.6-5.0 (HPLC), 1.4-2.0 (UPLC)=80-99% B (in 6 minutes followed by 7.5 minutes flush and re-equilibration)

Flow rate: all of the above methods have a flow rate of either 20 mL/min (Small Scale) or 40 mL/min (Large Scale).

High pH Method:
Column: the HPLC analysis was conducted on an XBridge C18 column (100 nm×19 nm i.d. 5 μm packing diameter) at ambient temperature
Solvents:
A: 10 mM Ammonium bicarbonate in water, adjusted to pH 10 with ammonia solution.
B: Acetonitrile.

Methods:
There were five methods used depending on the analytical retention time of the compound of interest. They had a 15-minute runtime, which comprised a 10 minute gradient followed by a 5 minute column flush and re-equilibration step.
Large/Small Scale 1.0-1.5 (HPLC), 0.4-0.6 (UPLC)=1-30% B
Large/Small Scale 1.5-2.2 (HPLC), 0.6-0.9 (UPLC)=15-55% B
Large/Small Scale 2.2-2.9 (HPLC), 0.9-1.2 (UPLC)=30-85% B
Large/Small Scale 2.9-3.6 (HPLC), 1.2-1.4 (UPLC)=50-99% B
Large/Small Scale 3.6-5.0 (HPLC), 1.4-2.0 (UPLC)=80-99% B (in 6 minutes followed by 7.5 minutes flush an re-equilibration)

Flow rate: all of the above methods have a flow rate of either 20 ml/min (small scale) or 40 ml/min (large scale)

Liquid Chromatography/Mass Spectrometry

Analysis of the above Examples by Liquid Chromatography/Mass Spectrometry (LC/MS) was carried out using the apparatus and conditions indicated in the methods shown below Liquid Chromatography:
Method Description: Formic Acid Generic Analytical UPLC Open Access LC/MS
2 Minute Method
LC/MS System: Acquity UPLC coupled with SQD mass spectrometer
LC Conditions
Column: Acquity UPLC BEH C18 (50 mm×2.1 mm i.d., 1.7 μm packing diameter
Column temperature: 40° C.
Solvents: A=0.1% v/v solution of Formic Acid in Water
B=0.1% v/v solution of Formic Acid in Acetonitrile
Injection Volume: 2 μl
The gradient table:

| Time (min) | Flow Rate (ml/min) | % A | % B |
|---|---|---|---|
| 0 | 0.9 | 97 | 3 |
| 1.5 | 0.9 | 0 | 100 |
| 1.9 | 0.9 | 0 | 100 |
| 2.0 | 0.05 | 97 | 3 |

Stop time: 2 min
UV Conditions
PDA Range: 210 nm-350 nm
The UV detection was a summed signal from wavelength of 210 nm to 350 nm
Acquisition Rate: 40 Hz
MS Conditions
Ionization Mode: Alternate—scan Positive and Negative Electrospray (ES$^+$/ES$^-$)
Scan Range: 100 to 1000 AMU
Scan Time: 0.15
Inter scan delays:
MS inter-scanan: 0.02 seconds
Polarity/Mode switch inter-scan: 0.02 seconds
Method Description: Ammonium Bicarbonate Generic Analytical UPLC Open Access LC/MS 2

Minute Method
LC/MS System: Acquity UPLC coupled with SQD mass spectrometer
LC Conditions
Column: Acquity UPLC BEH C18 (50 mm×2.1 mm i.d., 1.7 µm packing diameter)
Column temperature: 40° C.
Solvents: A=10 mM aqueous solution of $NH_4HCO_3$ (adjusted to pH 10 with ammonia)
B=Acetonitrile
Injection Volume: 1 µl
The gradient table:

| Time (min) | Flow Rate (mL/min) | % A | % B |
| --- | --- | --- | --- |
| 0 | 0.9 | 97 | 3 |
| 1.5 | 0.9 | 0 | 100 |
| 1.9 | 0.9 | 0 | 100 |
| 2.0 | 0.05 | 97 | 3 |

Stop time: 2 min
UV Conditions
PDA Range: 210 nm-350 nm
The UV detection was a summed signal from wavelength of 210 nm to 350 nm
Acquisition Rate: 40 Hz
MS Conditions
Ionization Mode: Alternate—scan Positive and Negative Electrospray ($ES^+/ES^-$)
Scan Range: 100 to 1000 AMU
Scan Time: 0.15
Inter scan delays:
MS inter-scanan: 0.02 seconds
Polarity/Mode switch inter-scan: 0.02 seconds
Synthetic Preparation of the Compounds of the Invention Scheme 1A Synthesis of Intermediate A Scheme 1B Synthesis of Intermediate B

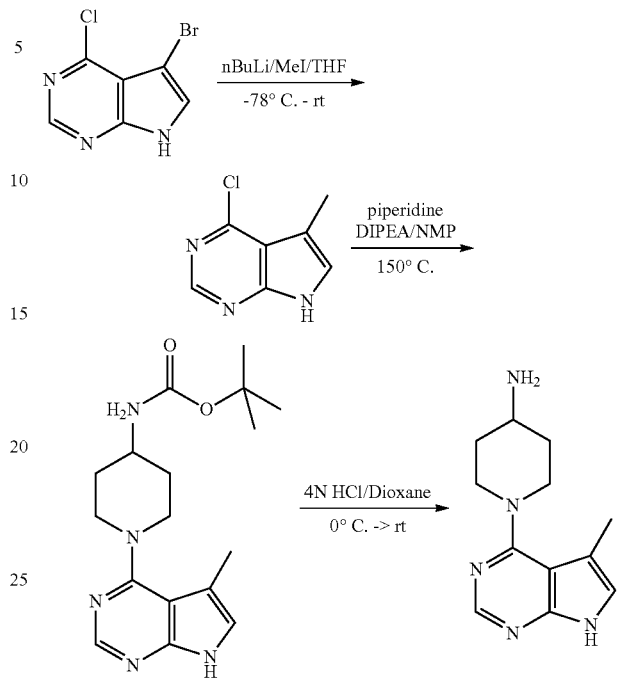

Scheme 1C Synthesis of Compound 1

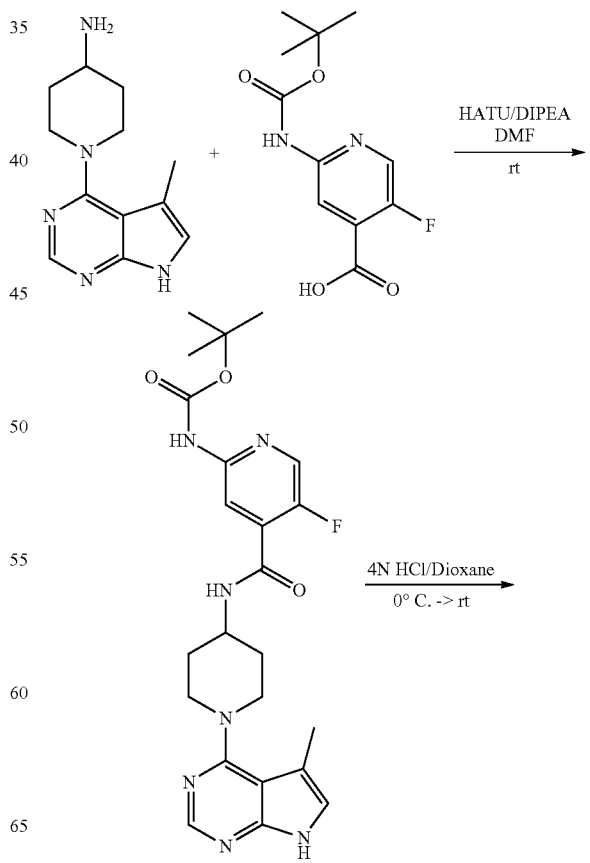

-continued

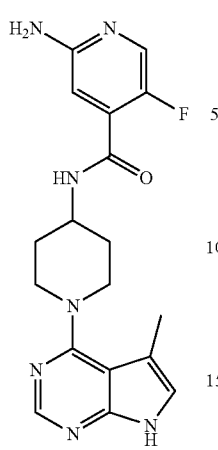

1.1 Compound 1: 2-amino-5-fluoro-N-[1-(5-methyl-7H-pyrrolo[2,3-d]pyrimidin-4-yl)-4-piperidyl]pyridine-4-carboxamide

1.1.1 Step 1: Synthesis of methyl 2-bromo-5-fluoro-pyridine-4-carboxylate

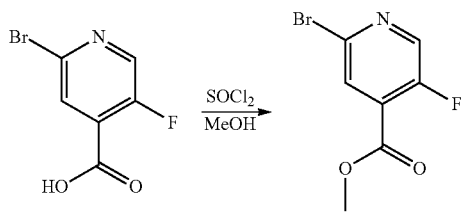

To a solution of 2-bromo-5-fluoro-pyridine-4-carboxylic acid (10.0 g, 45.5 mmol) in methanol (300 mL) cooled to 0° C. was added thionyl chloride (16.5 mL, 227.3 mmol) dropwise over 30 minutes. The reaction mixture was stirred at ambient temperature for 24 hours. Toluene (40 mL) was added to the reaction mixture. After evaporation of methanol, thionyl chloride was distilled out. The remaining toluene was evaporated on rotary evaporator affording the crude product, which was dissolved in dichloromethane (30 mL) evaporated under reduced pressure affording methyl 2-bromo-5-fluoro-pyridine-4-carboxylate (10.3 g). LCMS: MW (calcd): 232.9; MS (ES+, m/z): 234, 236 (M+H)+.

1.1.2 Alternative Synthetic Procedure

To a solution of 2-bromo-5-fluoro-pyridine-4-carboxylic acid (10.0 g, 45.5 mmol) in methanol (35 mL) and toluene (65 mL) cooled to 0° C. was added (trimethylsilyl)diazomethane (2.0 M solution in diethyl ether; 45.5 mL, 90.9 mmol) dropwise over 30 minutes. The reaction mixture was stirred at ambient temperature. After 2 h, the reaction mixture was evaporated under reduced pressure affording the crude product, which was dissolved in ethyl acetate (50 mL), washed with water (100 mL) and brine (50 mL) respectively, filtered through phase separator filter and evaporated under reduced pressure affording methyl 2-bromo-5-fluoro-pyridine-4-carboxylate (10.46 g). LCMS: MW (calcd): 232.9; MS (ES+, m/z): 234, 236 (M+H)+.

1.1.3 Step 2: Synthesis of methyl 2-(tert-butoxycarbonylamino)-5-fluoro-pyridine-4-carboxylate

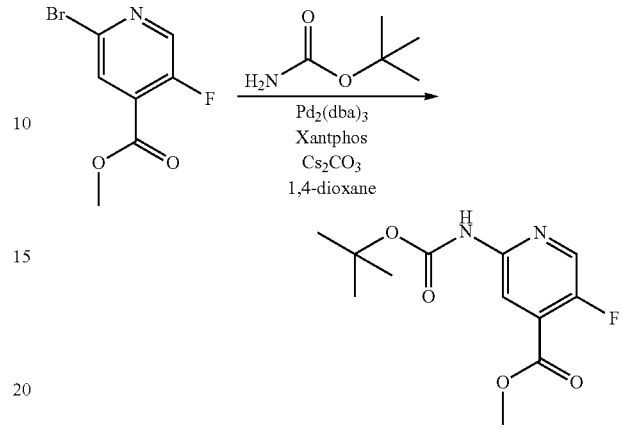

To a solution of methyl 2-bromo-5-fluoro-pyridine-4-carboxylate (10.3 g, 44.0 mmol) in 1,4-dioxane (150 mL) were added tert-butyl carbamate (6.18 g, 52.8 mmol), tris(dibenzylideneacetone)dipalladium(0) (0.86 g, 0.88 mmol), 4,5-bis(diphenylphosphino)-9,9-dimethylxanthene (1.02 g, 1.76 mmol) and cesium carbonate (20.08 g, 61.6 mmol). The reaction mixture was purged with argon, sonicated, caped and left to stir at 90° C. for 24 h. The reaction mixture was cooled, filtrated through pad of celite and washed with ethyl acetate. Mother liquor was washed with water (2×100 mL) and brine (100 mL) and evaporated under reduced pressure affording the crude product, which was triturated from ethyl acetate affording methyl 2-(tert-butoxycarbonylamino)-5-fluoro-pyridine-4-carboxylate (8.43 g). LCMS: MW (calcd): 270.1; MS (ES+, m/z): 215.41 (M+H-56)+.

1.1.4 Alternative Synthetic Procedure (methyl 2-((diphenylmethylene)amino)-5-fluoroisonicotinate Intermediate)

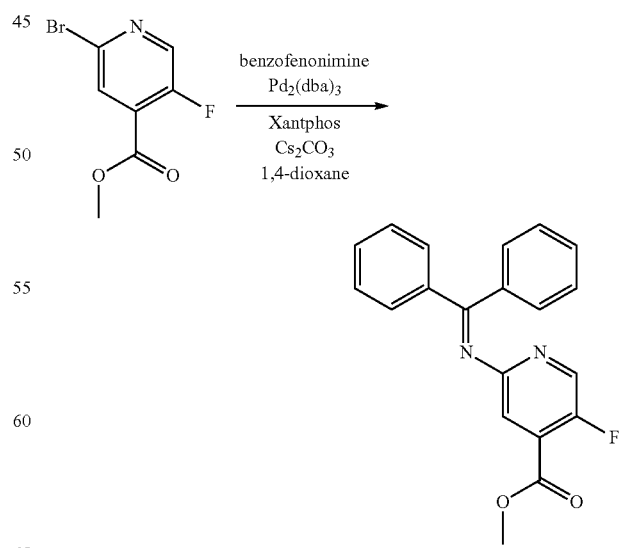

To a degassed and purged with argon suspension of methyl 2-bromo-5-fluoro-pyridine-4-carboxylate (308 mg, 1.32 mmol) in 1,4-dioxane (6 mL) was added benzophenoneimine (0.266 mL, 1.58 mmol), tris(dibenzylideneacetone)dipalladium(0) (24.1 mg, 0.026 mmol), 4,5-bis(diphenylphosphino)-9,9-dimethylxanthene (30.5 mg, 0.053 mmol) and cesium carbonate (602.0 mg, 0.053 mmol). The reaction mixture was flushed with argon, sonicated, caped and left to stir at 100° C. for 16 h. The reaction mixture was cooled, diluted with ethyl acetate (15 mL), washed with water (15 mL), brine (15 mL), and evaporated under reduced pressure affording methyl 2-((diphenylmethylene)amino)-5-fluoroisonicotinate (230 mg). LCMS: MW (calcd): 334.1; MS (ES+, m/z): 335.34 (M+H)+.

1.1.5 Step 3: Synthesis of 2-(tert-butoxycarbonylamino)-5-fluoro-pyridine-4-carboxylic acid

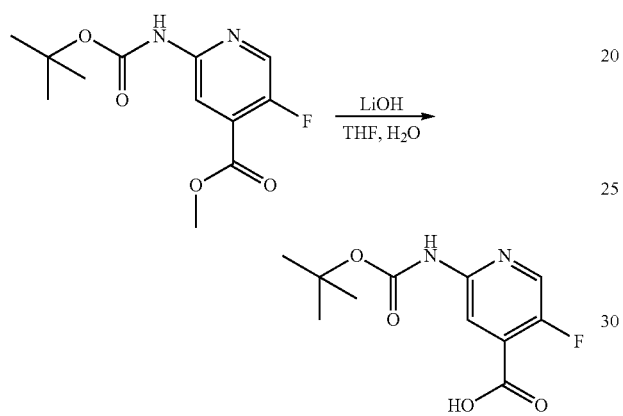

To a suspension of methyl 2-(tert-butoxycarbonylamino)-5-fluoro-pyridine-4-carboxylate (8.43 g, 31.19 mmol) in tetrahydrofuran (100 mL) was added lithium hydroxide (2.98 g, 124.76 mmol) and water (50 mL). The reaction mixture was left to stir overnight at ambient temperature. Next day tetrahydrofuran was evaporated under reduced pressure, the pH of water layer was adjusted to 4. The formed precipitate was filtered and coevaporated with toluene (4×20 mL) and dried in a vacuum oven at 40° C. for 5 h affording 2-(tert-butoxycarbonylamino)-5-fluoro-pyridine-4-carboxylic acid (7.79 g). LCMS: MW (calcd): 256.08; MS (ES+, m/z): 201.4 (M+H-56)+.

1.1.6 Step 4: Synthesis of 4-chloro-5-methyl-7H-pyrrolo[2,3-d]pyrimidine

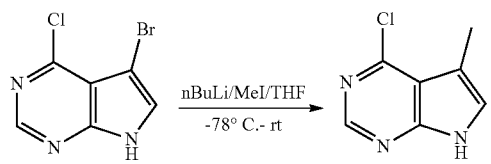

5-Bromo-4-chloro-7H-pyrrolo[2,3-d]pyrimidine (10.0 g, 43.0 mmol) was dissolved in dry THF (350 mL) and cooled to −78° C. under argon atmosphere. n-BuLi (2.5 M in hexane, 38 mL, 94.6 mmol) was added dropwise over one hour. After complete addition, the solution was stirred for 40 min and iodomethane (4.3 mL, 68.8 mmol) was added. The solution was allowed to slowly reach room temperature. Water (20 mL) was added and the solvent was removed in vacuum to yield brown slurry, which was dissolved in water (200 mL) and extracted with ethyl acetate (3×100 mL). Combined organics were washed with brine (150 mL), dried over anhydrous Na2SO4, filtered and concentrated to afford the crude compound that was triturated from ethyl acetate to yield 4-chloro-5-methyl-7H-pyrrolo[2,3-d] (5.32 g). LCMS: MW (calcd): 167.03; MS (ES+, m/z): 168.37 (M+H)+.

1.1.7 Step 5: Synthesis of tert-butyl N-[1-(5-methyl-7H-pyrrolo[2,3-d]pyrimidin-4-yl)-4-piperidyl]-carbamate

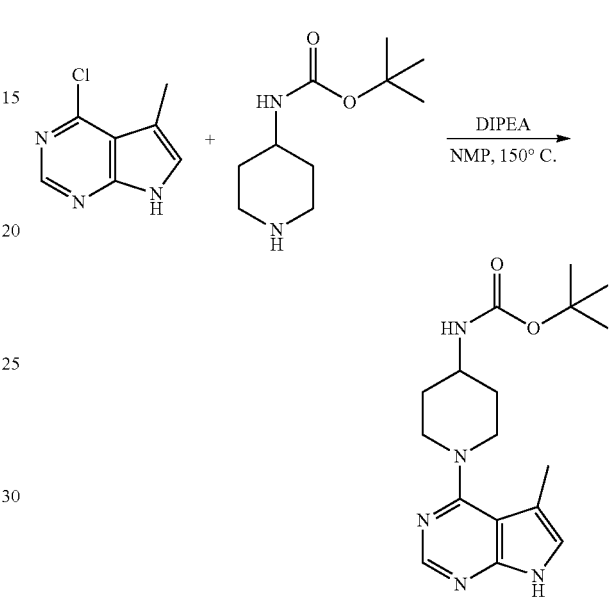

To a solution of 4-chloro-5-methyl-7H-pyrrolo[2,3-d] pyrimidine (10.0 g, 59.7 mmol) in 1-methyl-2-pyrrolidinone (40 mL) was added tert-butyl N-(4-piperidyl)carbamate (17.95 g, 89.6 mmol), and N,N-diisopropylethylamine (25.2 mL, 149.3 mmol). The reaction mixture was left to stir at 150° C. for 3 h. The reaction mixture was cooled and then poured into cold water (300 mL). To the mixture was added ethyl acetate (40 mL) and was left to stir for 30 min at ambient temperature. The formed precipitate was filtered, washed with water and diethyl ether and left to dry in vacuum oven at 40° C. overnight. Drying afforded tert-butyl N-[1-(5-methyl-7H-pyrrolo[2,3-d]pyrimidin-4-yl)-4-piperidyl]-carbamate (19.91 g). LCMS: MW (calcd): 331.2; MS (ES+, m/z): 332.7 (M+H)+.

1.1.8 Step 6: Synthesis of 1-(5-methyl-7H-pyrrolo[2,3-d]pyrimidin-4-yl)piperidin-4-amine

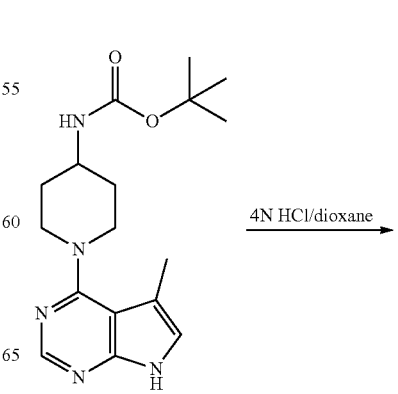

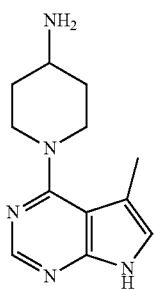

To a suspension of tert-butyl N-[1-(5-methyl-7H-pyrrolo[2,3-d]pyrimidin-4-yl)-4-piperidyl]carbamate (38.9 g, 117.3 mmol) in 1,4-dioxane (200 mL) cooled to 0° C. was added HCl (4M solution in dioxane) (290 mL). The reaction mixture was stirred at ambient temperature. After 23 h the reaction mixture was evaporated under reduced pressure, coevapoated with toluene (200 mL) and dried in vacuum oven at 40° C. overnight. Drying afforded 1-(5-methyl-7H-pyrrolo[2,3-d]pyrimidin-4-yl)piperidin-4-amine (47.68 g) as HCl salt. LCMS: MW (calcd): 231.15; MS (ES$^+$, m/z): 232.6 (M+H)$^+$.

1.1.9 Step 7: Synthesis of tert-butyl N-[5-fluoro-4-[[1-(5-methyl-7H-pyrrolo[2,3-d]pyrimidin-4-yl)-4-piperidyl]carbamoyl]-2-pyridyl]carbamate

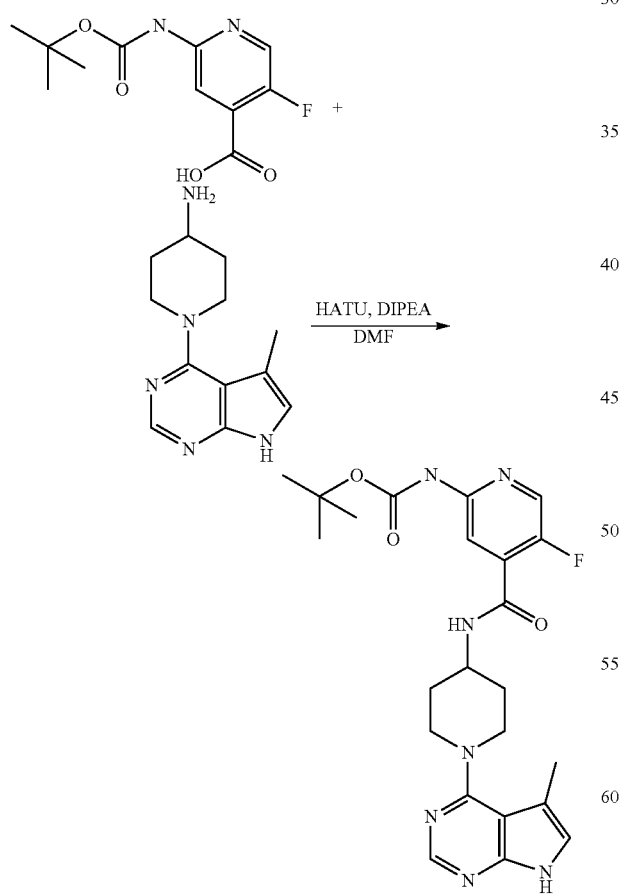

To a suspension of 2-(tert-butoxycarbonylamino)-5-fluoro-pyridine-4-carboxylic acid (14.25 g, 55.6 mmol) in N,N-dimethylformamide (130 mL) was added HATU (19.03 g, 50.1 mmol). The reaction mixture was stirred at ambient temperature for 20 min upon which 1-(5-methyl-7H-pyrrolo[2,3-d]pyrimidin-4-yl)piperidin-4-amine×2HCl (16.92 g, 55.6 mmol) and N,N-diisopropylethylamine (47.56 mL, 278.1 mmol) were added. The reaction mixture was stirred at ambient temperature. After 3 h reaction was completed. The reaction mixture was poured into ice cooled water (1.2 L). The formed precipitate was filtered, then washed with acetonitrile and dried in vacuum oven at 40° C. for 4 h affording tert-butyl N-[5-fluoro-4-[[1-(5-methyl-7H-pyrrolo[2,3-d]pyrimidin-4-yl)-4-piperidyl]carbamoyl]-2-pyridyl]carbamate (19.26 g). LCMS: MW (calcd): 469.22; MS (ES$^+$, m/z): 470.7 (M+H)$^+$.

1.1.10 Step 8: Synthesis of 2-amino-5-fluoro-N-[1-(5-methyl-7H-pyrrolo[2,3-d]pyrimidin-4-yl)-4-piperidyl] pyridine-4-carboxamide

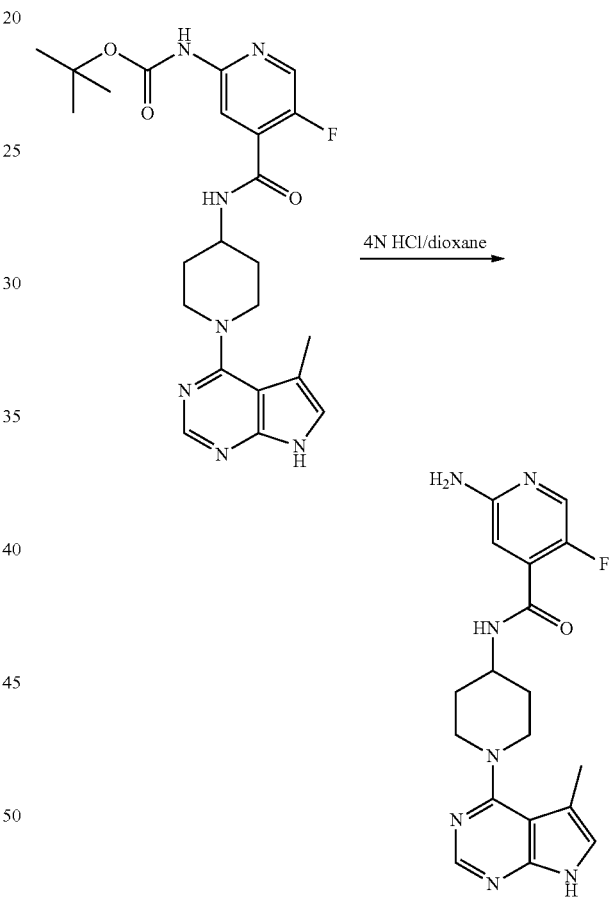

To a suspension of tert-butyl N-[5-fluoro-4-[[1-(5-methyl-7H-pyrrolo[2,3-d]pyrimidin-4-yl)-4-piperidyl]carbamoyl]-2-pyridyl]carbamate (25.76 g, 54.9 mmol) in dichloromethane (300 mL) cooled to 0° C. was added HCl (4M solution in dioxane) (130 mL) dropwise. After few minutes gummy residue was formed. Additional amount of dichloromethane (200 mL) was added to the reaction mixture. The gummy residue was crushed by sonification (after 45 min). The reaction mixture was stirred overnight at ambient temperature. The next day the precipitate was filtered and washed with water, acetonitrile and methanol and dried in vacuum oven at 40° C. for 5 h and then overnight at ambient temperature. Drying afforded 2-amino-5-fluoro-N-[1-(5-methyl-7H-pyrrolo[2,3-d]pyrimidin-4-yl)-

4-piperidyl]pyridine-4-carboxamide (13.65 g). LCMS: MW (calcd): 369.17; MS (ES+, m/z): 370.77 (M+H)+.

¹H NMR (600 MHz, DMSO-d6): δ=1.59-1.70 (m, J=12.3, 3.7 Hz, 2H), 1.93 (dd, J=12.6, 2.7 Hz, 2H), 2.34 (s, 3H), 3.06 (t, J=11.4 Hz, 2H), 3.94 (d, J=13.2 Hz, 2H), 3.95-4.03 (m, J=11.2, 11.2, 7.5, 4.2, 4.2 Hz, 1H), 6.02 (s, 2H), 6.51 (d, J=4.8 Hz, 1H), 7.05 (s, 1H), 7.91 (d, J=1.5 Hz, 1H), 8.19 (s, 1H), 8.46 (d, J=7.7 Hz, 1H), 11.51 (br. s., 1H) ppm.

1.2 Compound 2: (2-amino-5-methyl-N-[1-(5-methyl-7H-pyrrolo[2,3-d]pyrimidin-4-yl)-4-piperidyl]pyridine-4-carboxamide)

1.2.1 Step 1: Synthesis of methyl 2-amino-5-methyl-pyridine-4-carboxylate

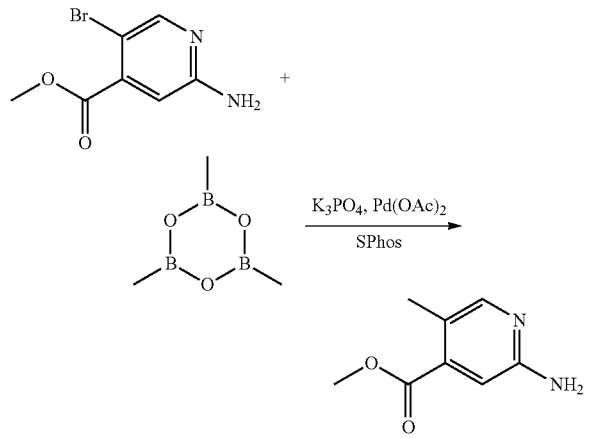

Methyl 2-amino-5-bromo-pyridine-4-carboxylate (200 mg, 0.87 mmol), S-Phos (4.6 mg, 3.2 mmol), tripotassium phosphate (369.3 mg, 1.74 mmol) and diacetoxypalladium (19.5 g, 0.011 mmol) were combined, degassed and backfilled with N₂ and then dissolved in DMSO (4 ml) and trimethylboroxine (467.5 μL, 3.2 mmol) at rt. The mixture was then heated to 80° C. and stirred overnight. After 16 hours the mixture was diluted with EtOAc and washed with H₂O. The organic phase was dried over Na₂SO₄, filtered, absorbed onto celite and concentrated in vacuo to afford crude product which was purified via Biotage purification device on 4 g KP-Sil Interchim column with flowrate 9 ml/min, DCM as solvent A and DCM:MeOH=20:1 as solvent B. The appropriate fractions have been collected to afford methyl 2-amino-5-methyl-pyridine-4-carboxylate (167.03 mg). LCMS: MW (calcd): 166.07; MS (ES+, m/z): 167.03 (M+H)+.

1.2.2 Step 2: Synthesis of 2-amino-5-methyl-pyridine-4-carboxylic acid

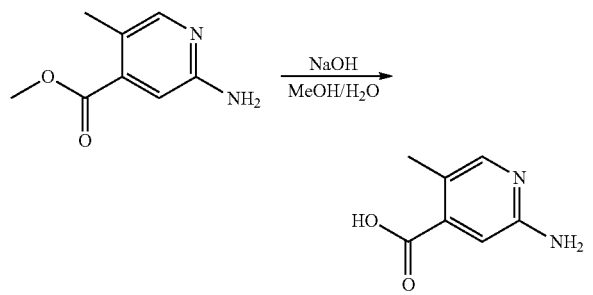

Methyl 2-amino-5-methyl-pyridine-4-carboxylate (125 mg, 0.75 mmol) was dissolved in MeOH/H₂O (2/2) and NaOH (1M solution, 0.75 μL) was added. The mixture was then heated to 60° C. and allowed to stir 1 h. After 1 h MeOH was evaporated and aqueous residue was extracted with EtOAc. Desired product left in aqueous layer which was lyophilized overnight.

After lyophilisation, mixture was dissolved in acetone, filtered and mother liquor was evaporated to obtain 2-amino-5-methyl-pyridine-4-carboxylic acid (55 mg). LCMS: MW (calcd): 152.06; MS (ES+, m/z): 153.02 (M+H)+.

1.2.3 Step 3: Synthesis 2-amino-5-methyl-N-[1-(5-methyl-7H-pyrrolo[2,3-d]pyrimidin-4-yl)-4-piperidyl]pyridine-4-carboxamide

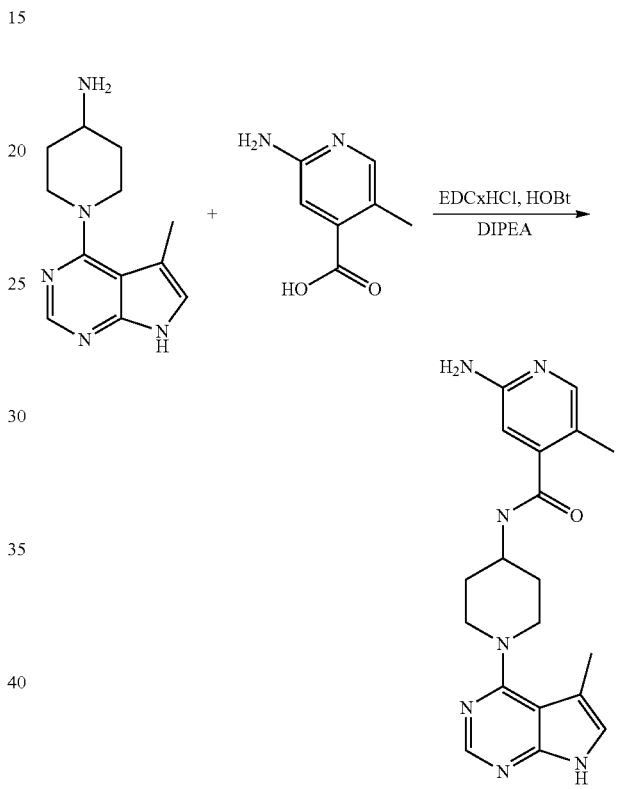

To a solution of 2-amino-5-methyl-pyridine-4-carboxylic acid (33 mg, 0.22 mmol) in DMF (1 mL) at 0° C. was added EDCxHCl (54.8 mg, 0.29 mmol) and DIPEA (111.1 μL, 0.64 mmol) and left stirring for 30 minutes. Then HOBtxH₂O (35.6 mg, 0.26 mmol) and 1-(5-methyl-7H-pyrrolo[2,3-d]pyrimidin-4-yl)piperidin-4-amine (50.2 mg, 0.22 mmol) were added. The reaction was left stirred overnight at room temperature. Next day reaction mixture was diluted with water (5 mL) and extracted with EtOAc (3×5 mL). The combined organic layers were washed with brine (10 mL), dried over Na₂SO₄, filtered and concentrated in vacuo to afford crude product which was purified via Biotage purification device on 4 g KP-Sil Interchim column with flow rate 9 ml/min, DCM as weak solvent and DCM:MeOH:NH₄OH=90:1.5:0.15 as strong solvent. The appropriate fractions have been collected to afford 2-amino-5-methyl-N-[1-(5-methyl-7H-pyrrolo[2,3-d]pyrimidin-4-yl)-4-piperidyl]pyridine-4-carboxamide (8 mg). LCMS: MW (calcd): 365.20; MS (ES+, m/z): 366.23 (M+H)+. ¹H NMR (300 MHz, DMSO-d6) δ 11.51 (br. s., 1H), 8.35 (d, J=8.01 Hz, 1H), 8.17 (s, 1H), 7.75 (s, 1H), 7.05 (s, 1H), 6.35 (s, 1H), 5.81 (s, 2H), 3.95 (m, 3H), 3.05 (t, J=11.41 Hz, 2H), 2.34 (s, 3H), 2.06 (s, 3H), 1.92 (d, J=9.58 Hz, 2H), 1.56-1.70 (m, 2H) ppm.

1.3: Compound 3: 2-amino-5-chloro-N-[1-(5-methyl-7H-pyrrolo[2,3-d]pyrimidin-4-yl)-4-piperidyl]-pyridine-4-carboxamide

1.3.1 Step 1: Synthesis of 3-chloro-1-oxo-pyridine-4-carboxylic acid

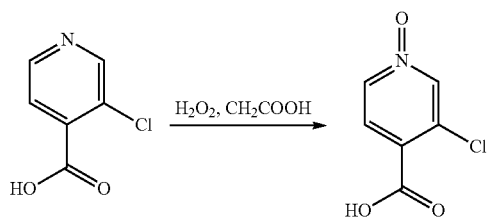 [SMILES: O=C(O)c1ccncc1Cl ; O=C(O)c1cc[n+]([O-])cc1Cl]

3-Chloropyridine-4-carboxylic (620 mg, 3.94 mmol) was dissolved in acetic acid (2 mL) and 30% aq $H_2O_2$ (6 mL) was added. The reaction mixture was heated for 38 h at 80° C. After completion it was concentrated to half of its volume. Formed crystals were filtered off and dried in vacuum drier to afford 3-chloro-1-oxo-pyridine-4-carboxylic acid (420 mg). LCMS: MW (calcd): 172.99; MS (ES+, m/z): 174.33 (M+H)+.

1.3.2 Step 2: Synthesis of 3-chloro-N-[1-(5-methyl-7H-pyrrolo[2,3-d]pyrimidin-4-yl)-4-piperidyl]-1-oxo-pyridine-4-carboxamide

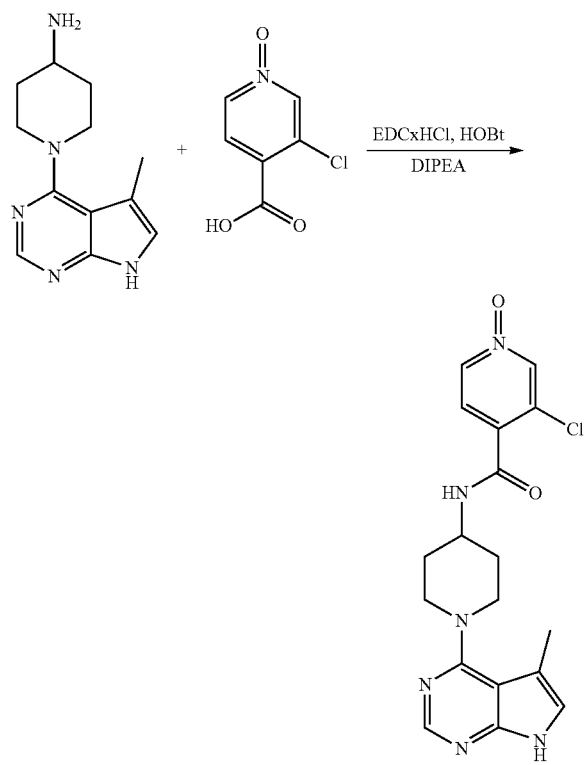

To a solution of 3-chloro-1-oxo-pyridine-4-carboxylic acid (52 mg, 0.30 mmol) in DMF (1 mL) at 0° C. was added EDCxHCl (74.8 mg, 0.39 mmol) and DIPEA (161 μL, 0.87 mmol) and left stirring for 30 minutes. Then HOBtxH$_2$O (55.1 mg, 0.36 mmol) and 1-(5-methyl-7H-pyrrolo[2,3-d]pyrimidin-4-yl)piperidin-4-amine (69.4 mg, 0.30 mmol) were added. The reaction was left stirred overnight at room temperature. Next day reaction mixture was evaporated to dryness. Oily residue was purified by silicagel column chromatography (weak eluent: DCM, strong eluent: DCM: MeOH:NH$_4$OH=90:5:0.1) to afford 3-chloro-N-[1-(5-methyl-7H-pyrrolo[2,3-d]pyrimidin-4-yl)-4-piperidyl]-1-oxo-pyridine-4-carboxamide (87 mg). LCMS: MW (calcd): 386.13; MS (ES+, m/z): 387.49 (M+H)+.

1.3.3 Step 3: Synthesis of 2-amino-5-chloro-N-[1-(5-methyl-7H-pyrrolo[2,3-d]pyrimidin-4-yl)-4-piperidyl]pyridine-4-carboxamide

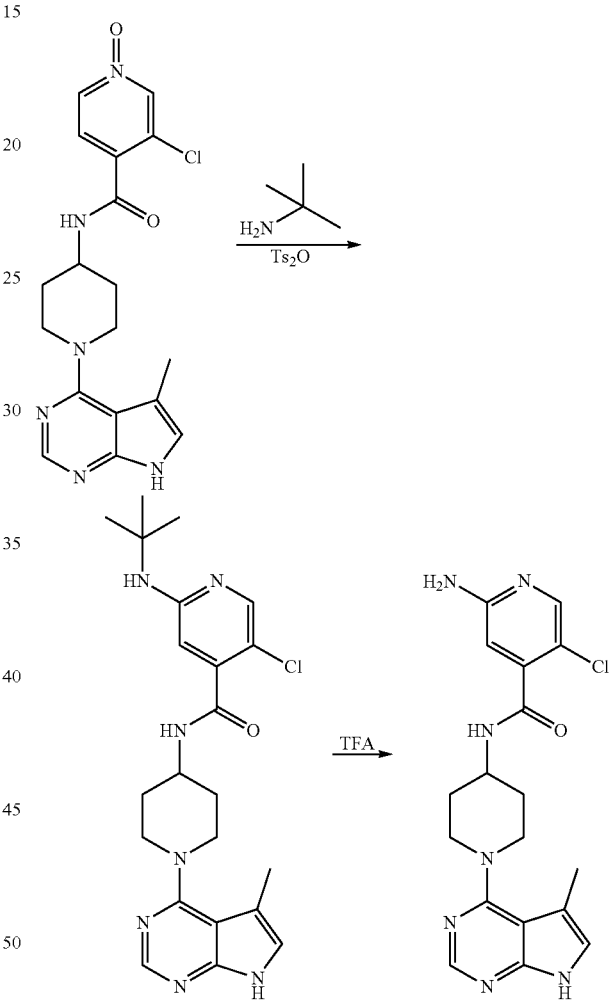

To a solution of 3-chloro-N-[1-(5-methyl-7H-pyrrolo[2,3-d]pyrimidin-4-yl)-4-piperidyl]-1-oxo-pyridine-4-carboxamide (87 mg, 0.23 mmol) and tert-butylamine (0.160 mL, 1.53 mmol) in a mixture of chloroform (10 mL) and benzotrifluoride (1 mL) at 0° C. was added p-toluenesulfonic anhydride (260 mg, 0.57 mmol) in portions while maintaining temperature at 5° C. Reaction was completed after 10 min. Solution of trifluoroacetic acid (5 mL) and reaction mixture was stirred for 3 h at 80° C. Solvents were reduced under vacuum and the residue was diluted with dichloromethane and quenched with 40% NaOH to pH 9-10. The aqueous layer was extracted with dichloromethane (4×15 mL). The combined organics were dried over Na$_2$SO$_4$, concentrated and purified by silicagel column chromatography (weak eluent: DCM, strong eluent: DCM:MeOH:

NH₄OH=90:9:0.5) to give 2-amino-5-chloro-N-[1-(5-methyl-7H-pyrrolo[2,3-d]pyrimidin-4-yl)-4-piperidyl]pyridine-4-carboxamide (9.05 mg). LCMS: MW (calcd): 385.14; MS (ES⁺, m/z): 386.54 (M+H)⁺. ¹H NMR (500 MHz, DMSO-d6) δ 11.52 (br. s., 1H), 8.52 (d, J=7.63 Hz, 1H), 8.20 (s, 1H), 7.91 (d, J=4.88 Hz, 1H), 7.06 (s, 1H), 6.52 (d, J=4.88 Hz, 1H), 6.42 (s, 2H), 3.94 (m, 3H), 3.08 (t, J=11.44 Hz, 2H), 2.34 (s, 3H), 1.95 (d, J=9.77 Hz, 2H), 1.57-1.71 (m, 2H) ppm.

1.4: Compound 4: 2-amino-N-[1-(5-chloro-7H-pyrrolo[2,3-d]pyrimidin-4-yl)-4-piperidyl]pyridine-4-carboxamide

1.4.1 Step 1: Synthesis of 4,5-dichloro-7H-pyrrolo[2,3-d]pyrimidine

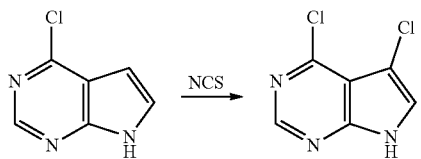

To a solution of 4-chloro-7H-pyrrolo[2,3-d]pyrimidine (2.0 g, 13.04 mmol) in DCM (80 mL) was added N-chlorosuccinimide (1.7 g, 13.04 mmol). The reaction mixture was refluxed 3 days. The reaction mixture was dissolved in water and extracted with EtOAc (3×50 mL). Combined organic layers were dried over MgSO4, filtered and evaporated to afford 4,5-dichloro-7H-pyrrolo[2,3-d]pyrimidine (1.08 g). LCMS: MW (calcd): 186.97; MS (ES⁺, m/z): 187.98 (M+H)⁺.

1.4.2 Step 2: Synthesis of tert-butyl N-(5-chloro-7H-pyrrolo[2,3-d]pyrimidin-4-yl)carbamate

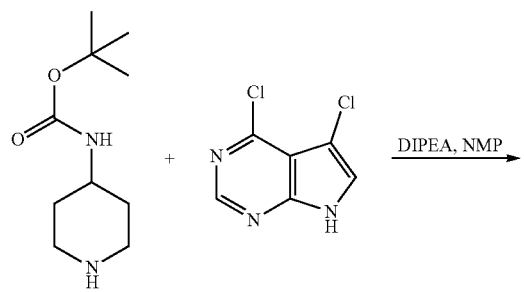

Tert-butyl N-(4-piperidyl)carbamate (895.3 mg, 4.47 mmol) and 4,5-dichloro-7H-pyrrolo[2,3-d]pyrimidine (1080 mg, 5.36 mmol) were dissolved in NMP (8 ml) and DIPEA (2.33 ml, 13.4 mmol) was added dropwise. The reaction mixture was stirred at room temperature 3 days. The mixture was dissolved in water and extracted with EtOAc (3×15 mL). Combined organic layers were dried and concentrated to afford the crude product which was recrystallized with acetonitrile to afford tert-butyl N-(5-chloro-7H-pyrrolo[2,3-d]pyrimidin-4-yl)carbamate (1.42 g). LCMS: MW (calcd): 351.15; MS (ES⁺, m/z): 352.22 (M+H)⁺.

1.4.3 Step 3. Synthesis of 1-(5-chloro-7H-pyrrolo[2,3-d]pyrimidin-4-yl)piperidin-4-amine

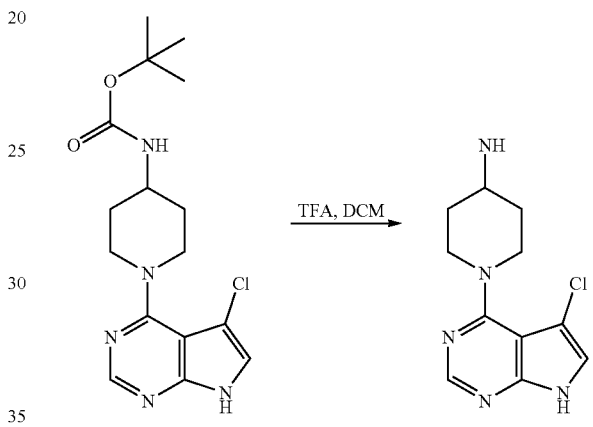

To a solution of tert-butyl N-[1-(5-chloro-7H-pyrrolo[2,3-d]pyrimidin-4-yl)-4-piperidyl]carbamate (2.0 g, 5.69 mmol) in DCM (10 mL) was added trifluoracetic acid (3.3 mL) and the resulting solution was stirred at rt for 2 h. Upon completion solvent was evaporated and crude product was put on a previous conditioned (40 mL MeOH) SCX column (20 g). The column was washed with MeOH (2×40 mL) and then with 7 N NH₃/MeOH (100 mL). Solvent was evaporated to afford 1-(5-chloro-7H-pyrrolo[2,3-d]pyrimidin-4-yl)piperidin-4-amine (1.3 g). LCMS: MW (calcd): 251.09; MS (ES⁺, m/z): 252.10 (M+H)⁺.

1.4.4 Step 4. Synthesis of 2-amino-N-[1-(5-chloro-7H-pyrrolo[2,3-d]pyrimidin-4-yl)-4-piperidyl]-pyridine-4-carboxamide

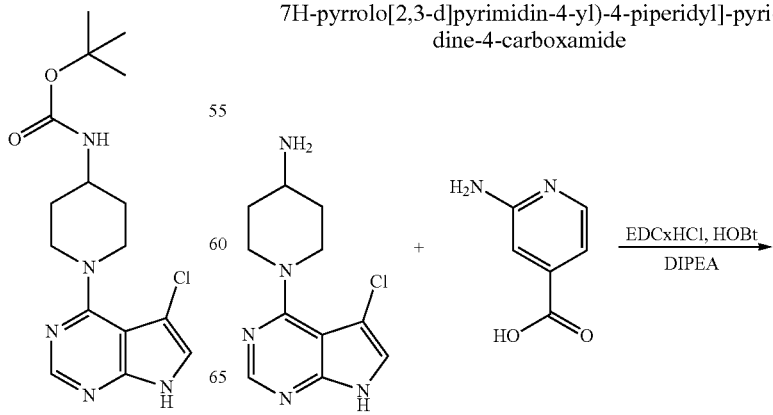

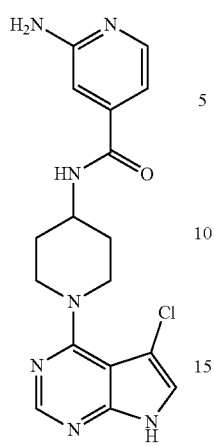

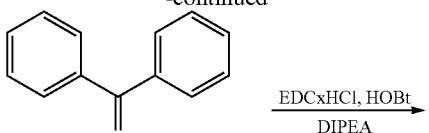

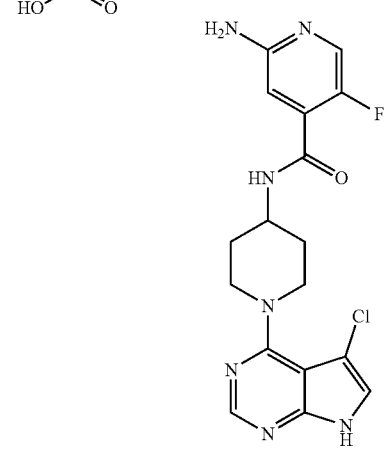

To a solution of 2-aminopyridine-4-carboxylic acid (200 mg, 1.45 mmol) in DMF (4 mL) at 0° C. was added EDCxHCl (362.3 mg, 1.89 mmol) and DIPEA (732 μL, 4.21 mmol) and left stirring for 30 minutes. Then HOBtxH$_2$O (266.4 mg, 1.74 mmol) and 1-(5-chloro-7H-pyrrolo[2,3-d]pyrimidin-4-yl)piperidin-4-amine (546.23 mg, 2.17 mmol) were added. The reaction was left stirred overnight at room temperature, diluted with water (10 mL) and extracted with EtOAc (3×10 mL). The combined organic layers were washed with brine (20 mL), dried over Na$_2$SO$_4$, filtered and concentrated in vacuo. Crude was purified via Biotage purification device on 12 g KP-Sil Interchim column: DCM as weak solvent and DCM:MeOH:NH$_4$OH=90:1.5:0.15 as strong solvent. The appropriate fractions have been collected to afford product which was triturated with acetonitrile to afford 2-amino-N-[1-(5-chloro-7H-pyrrolo[2,3-d]pyrimidin-4-yl)-4-piperidyl]-pyridine-4-carboxamide (162.1 mg). LCMS: MW (calcd): 371.13; MS (ES$^+$, m/z): 372.18 (M+H)$^+$. $^1$H NMR (500 MHz, DMSO-d6) δ 12.15 (br. s., 1H), 8.39 (d, J=7.32 Hz, 1H), 8.27 (s, 1H), 7.97 (d, J=4.88 Hz, 1H), 7.49 (s, 1H), 6.77-6.87 (m, 2H), 6.09 (br. s., 2H), 4.21 (d, J=12.21 Hz, 2H), 4.05 (d, J=7.32 Hz, 1H), 3.10 (t, J=12.36 Hz, 2H), 1.91 (d, J=10.68 Hz, 2H), 1.74 (m, 2H) ppm.

1.5 Compound 5: Synthesis of 2-amino-N-[1-(5-chloro-7H-pyrrolo[2,3-d]pyrimidin-4-yl)-4-piperidyl]-5-fluoro-pyridine-4-carboxamide

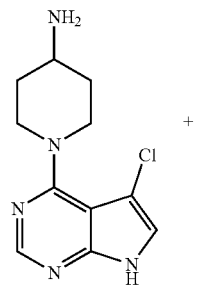

+

To a solution of 2-(benzhydrylideneamino)-5-fluoro-pyridine-4-carboxylic acid (43.0 mg, 0.13 mmol) in DMF (5 mL) at 0° C. was added EDCxHCl (32.6 mg, 0.17 mmol) and DIPEA (66.1 μL, 0.38 mmol) and left stirring for 30 minutes. Then HOBtxH$_2$O (24.5 mg, 0.16 mmol) and 1-(5-chloro-7H-pyrrolo[2,3-d]pyrimidin-4-yl)piperidin-4-amine (50.3 mg, 0.20 mmol) were added. The reaction was left stirred overnight at room temperature. Solvent was evaporated to dryness. Crude was purified via preparative LC-MS. Appropriate fractions have been collected and lyophilized overnight to afford 2-amino-N-[1-(5-chloro-7H-pyrrolo[2,3-d]pyrimidin-4-yl)-4-piperidyl]-5-fluoro-pyridine-4-carboxamide (17 mg). LCMS: MW (calcd): 389.12; MS (ES$^+$, m/z): 390.39 (M+H)$^+$. $^1$H NMR (600 MHz, DMSO-d6) δ 12.15 (br. s., 1H), 8.47 (d, J=7.70 Hz, 1H), 8.25 (s, 1H), 7.91 (s, 1H), 7.47 (s, 1H), 6.51 (d, J=4.40 Hz, 1H), 6.02 (s, 2H), 4.14 (d, J=12.65 Hz, 2H), 4.02 (m, 1H), 3.13 (t, J=11.83 Hz, 2H), 1.93 (d, J=10.82 Hz, 2H), 1.67 (m, 2H) ppm.

1.6 Compound 6: Synthesis of 2-amino-N-[1-(5-cyano-3-methyl-1H-pyrrolo[2,3-b]pyridin-4-yl)-4-piperidyl]-5-fluoro-pyridine-4-carboxamide

1.6.1. Synthesis of 3-bromo-4-chloro-1H-pyrrolo[2,3-b]pyridine-5-carbonitrile

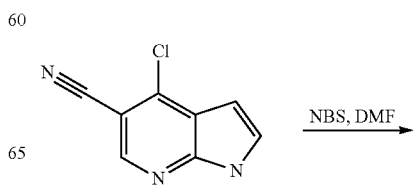

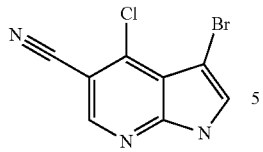

To a stirred solution of 4-chloro-1H-pyrrolo(3,2-b)pyridine-5-carbonitrile (3 g, 16.89 mmol) in DMF (20 mL) was added N-bromosuccinimide (3.3 g, 18.582 mmol). The resulting solution was stirred at room temperature for 20 min. The reaction mixture was diluted with water (50 mL) and extracted with ethyl acetate (2×25 mL). The combined organic layers were washed with brine, dried over magnesium sulfate and concentrated in vacuo. Resulting powder was triturated with EtOAc and dried to afford 3-bromo-4-chloro-1H-pyrrolo[2,3-b]pyridine-5-carbonitrile (1.5 g). LCMS: MW (calcd): 256.49; MS (ES+, m/z): 257.93 (M+H)+.

1.6.2. Synthesis of 4-chloro-3-methyl-1H-pyrrolo[2,3-b]pyridine-5-carbonitrile

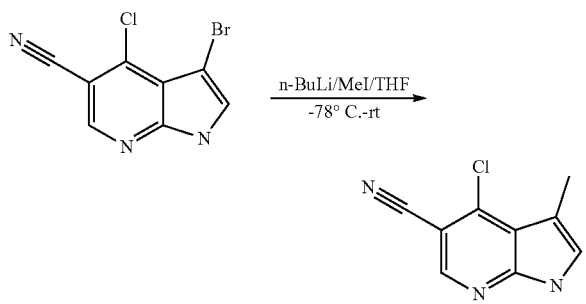

To a solution of 3-bromo-4-chloro-1H-pyrrolo[2,3-b]pyridine-5-carbonitrile (1.5 g, 5.85 mmol) in THF (48 mL) at −78° C. under argon was added butyllithium solution (5.2 mL, 12.87 mmol) and the reaction was stirred for 20 min. Iodomethane (590 µL, 9.36 mmol) was then added dropwise and the reaction allowed to warm to room temperature in the cold bath. The reaction was quenched with water (30 mL) and pH was adjusted to 7. THF was evaporated and water was added. The obtained solid was filtered, washed with water and triturated with EtOAc to afford 4-chloro-3-methyl-1H-pyrrolo[2,3-b]pyridine-5-carbonitrile (813 mg). LCMS: MW (calcd): 191.6; MS (ES+, m/z): 192.05 (M+H)+.

1.6.3. Synthesis of tert-butyl N-[1-(5-cyano-3-methyl-1H-pyrrolo[2,3-b]pyridin-4-yl)-4-piperidyl]carbamate

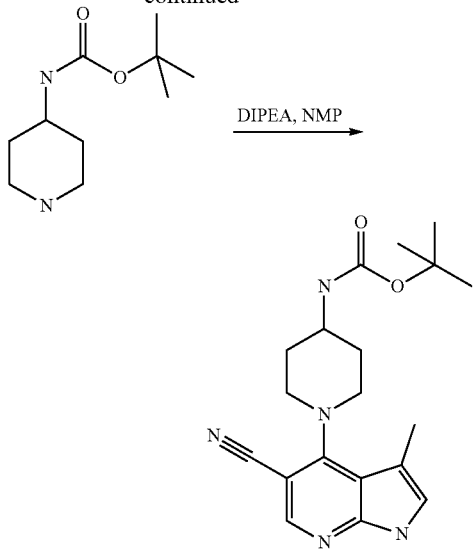

A mixture of 4-chloro-3-methyl-1H-pyrrolo[2,3-b]pyridine-5-carbonitrile (813 mg, 4.24 mmol), 4-boc-aminopiperidine (1.27 g, 6.36 mmol) and DIPEA (1.85 mL, 10.61 mmol) in NMP (5 mL) was stirred at 150° C. for 3 h and stirring was continued at RT over the weekend. The reaction mixture was diluted with water (110 mL) and diethyl ether. The obtained solid was filtered, washed with water and diethyl ether and dried to afford tert-butyl N-[1-(5-cyano-3-methyl-1H-pyrrolo[2,3-b]pyridin-4-yl)-4-piperidyl]carbamate (1.28 g). LCMS: MW (calcd): 355.43; MS (ES+, m/z): 356.30 (M+H)+.

1.6.4. Synthesis of 4-(4-amino-1-piperidyl)-3-methyl-1H-pyrrolo[2,3-b]pyridine-5-carbonitrile

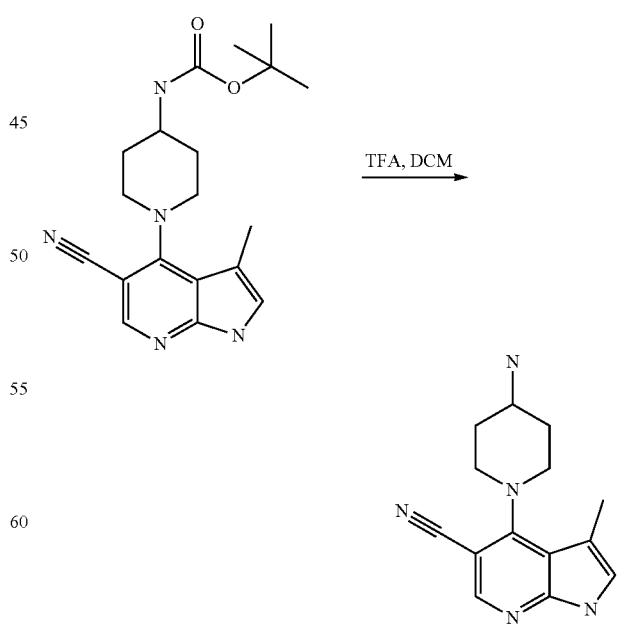

To a solution of tert-butyl N-[1-(5-cyano-3-methyl-1H-pyrrolo[2,3-b]pyridin-4-yl)-4-piperidyl]carbamate (1.28 g, 3.6 mmol) in DCM (40 mL) was added trifluoroacetic acid (5.5 mL, 72.03 mmol). The resulting solution was stirred at room temperature for 1 h. The reaction mixture was loaded onto an SCX column (20 g, preconditioned with 100 mL of MeOH). MeOH (200 mL) was passed through the column and the compound was eluted with 7N NH₃ in MeOH: MeOH=1:4 (300 mL). The filtrate was concentrated in vacuo to afford 4-(4-amino-1-piperidyl)-3-methyl-1H-pyrrolo[2,3-b]pyridine-5-carbonitrile (1.06 g). LCMS: MW (calcd): 255.32; MS (ES⁺, m/z): 256.21 (M+H)⁺.

1.6.5. Synthesis of 2-amino-N-[1-(5-cyano-3-methyl-1H-pyrrolo[2,3-b]pyridin-4-yl)-4-piperidyl]-5-fluoro-pyridine-4-carboxamide

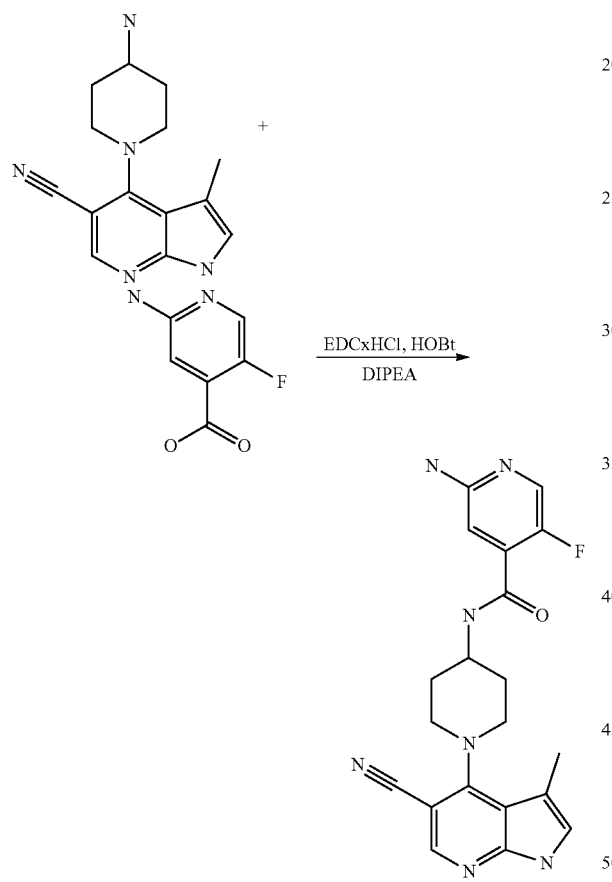

To a solution of 2-amino-5-fluoro-pyridine-4-carboxylic acid (66.0 mg, 0.30 mmol) in DMF (1 mL) at 0° C. was added EDCxHCl (50.0 mg, 0.26 mmol) and DIPEA (101 μL, 0.58 mmol) and left stirring for 30 minutes. Then HOBtx H₂O (37.0 mg, 0.24 mmol) and 4-(4-amino-1-piperidyl)-3-methyl-1H-pyrrolo[2,3-b]pyridine-5-carbonitrile (108.0 mg, 0.30 mmol) were added. The reaction was left stirred overnight at room temperature. Solvent was evaporated to dryness. Crude was purified via Biotage purification device on 4 g KP-Sil Interchim column: DCM as weak solvent and DCM:MeOH=10:1 as strong solvent. The appropriate fractions have been collected to afford 2-amino-N-[1-(5-cyano-3-methyl-1H-pyrrolo[2,3-b]pyridin-4-yl)-4-piperidyl]-5-fluoro-pyridine-4-carboxamide (1.27 mg). LCMS: MW (calcd): 393.42; MS (ES⁺, m/z): 394.53 (M+H)⁺. ¹H NMR (500 MHz, DMSO-d6) δ 11.82 (br. s., 1H), 8.55 (d, J=7.32 Hz, 1H), 8.23 (s, 1H), 7.93 (s, 1H), 7.24 (s, 1H), 6.54 (d, J=4.27 Hz, 1H), 6.04 (br. s., 2H), 3.97 (br. s., 1H), 3.62 (d, J=12.21 Hz, 2H), 3.40 (m, 2H), 2.41 (s, 3H), 1.97 (d, J=11.29 Hz, 2H), 1.72-1.83 (m, 2H) ppm.

Compound 7: Synthesis of 2-amino-N-[1-(3-chloro-1H-pyrrolo[2,3-b]pyridin-4-yl)-4-piperidyl]-5-fluoro-pyridine-4-carboxamide

1.7.1. Synthesis of tert-butyl N-[1-(1H-pyrrolo[2,3-b]pyridin-4-yl)-4-piperidyl]carbamate

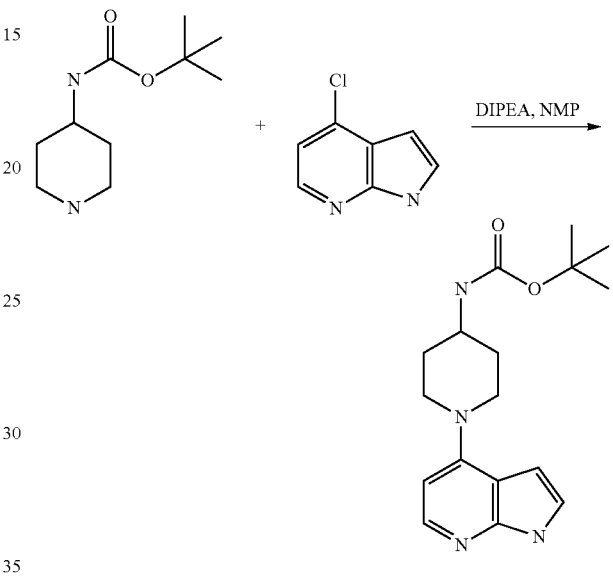

A mixture of 4-chloro-1H-pyrrolo[2,3-b]pyridine (4.0 g, 26.20 mmol), tert-butyl N-(4-piperidyl)carbamate (7.8 g, 39.30 mmol) and DIPEA (11.4 mL, 65.50 mmol) in NMP (28 mL) was stirred at 150° C. for 72 h. The reaction mixture was diluted with water and extracted with EtOAc (4×).

Combined organic layers were dried and concentrated to afford the crude product which was recrystallized with acetonitrile to afford tert-butyl N-[1-(1H-pyrrolo[2,3-b]pyridin-4-yl)-4-piperidyl]carbamate (1.88 g). LCMS: MW (calcd): 316.41; MS (ES⁺, m/z): 317.22 (M+H)⁺.

1.7.2. Synthesis of tert-butyl N-[1-(3-chloro-1H-pyrrolo[2,3-b]pyridin-4-yl)-4-piperidyl]carbamate

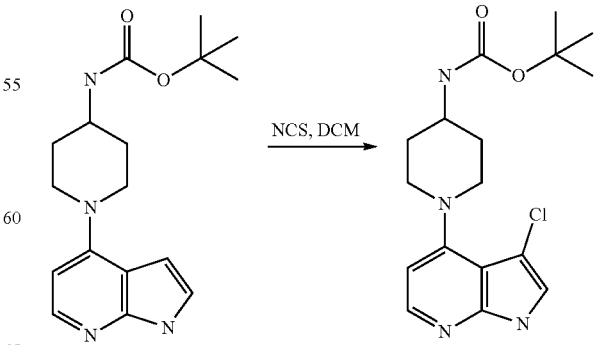

tert-butyl N-[1-(1H-pyrrolo[2,3-b]pyridin-4-yl)-4-piperidyl]carbamate (316 mg, 1 mmol) was dissolved in dry DCM (10 ml) and N-chlorosuccinimide (147 mg, 1.1 mmol) was added. The reaction mixture was left stirring at 40° C. After 16 h to the reaction mixture was added water and extracted with DCM (3×). Combined organic layer was dried over anhydrous Na$_2$SO$_4$, filtered thorough phase separator and evaporated to obtain the crude compound which was purified via Biotage purification device on 4 g KP-Sil Interchim column with flowrate 10 ml/min, DCM as solvent A and DCM: MeOH=7:3 as solvent B. Method: 0-5% B 4 CV; 20% 4 CV; 20-40% B 5 CV; 40% B 5 CV; 40-60% B 4 CV; 60% B 4 CV. Appropriate fractions were gathered to afford tert-butyl N-[1-(3-chloro-1H-pyrrolo[2,3-b]pyridin-4-yl)-4-piperidyl]carbamate (150 mg). LCMS: MW (calcd): 350.85; MS (ES$^+$, m/z): 351.43 (M+H)$^+$.

1.7.3. Synthesis of 1-(3-chloro-1H-pyrrolo[2,3-b]pyridin-4-yl)piperidin-4-amine

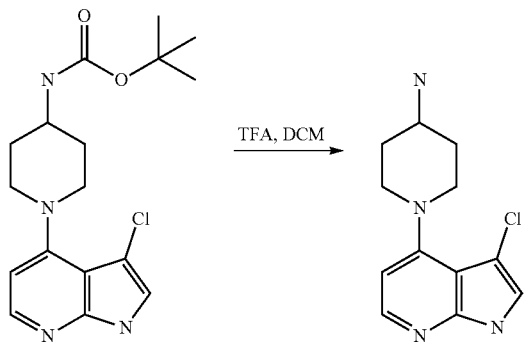 [SMILES: CC(C)(C)OC(=O)NC1CCN(c2ccnc3[nH]cc(Cl)c23)CC1 ; NC1CCN(c2ccnc3[nH]cc(Cl)c23)CC1]

To a mixture of tert-butyl N-[1-(3-chloro-1H-pyrrolo[2,3-b]pyridin-4-yl)-4-piperidyl]carbamate (320 mg, 1.8 mmol) in DCM (10 mL) at 0° C. TFA (1.5 mL) was added. Reaction mixture was stirred at r.t. for 1 h. After completion solvent was evaporated and crude product was put on a previous conditioned (with MeOH) SCX column (5 g). The column was washed with MeOH (2×5 ml) and then with 7 N NH3/MeOH (10 ml) to afford 1-(3-chloro-1H-pyrrolo[2,3-b]pyridin-4-yl)piperidin-4-amine (108 mg). LCMS: MW (calcd): 250.73; MS (ES$^+$, m/z): 251.38 (M+H)$^+$.

1.7.4. Synthesis of 2-amino-N-[1-(3-chloro-1H-pyrrolo[2,3-b]pyridin-4-yl)-4-piperidyl]-5-fluoro-pyridine-4-carboxamide

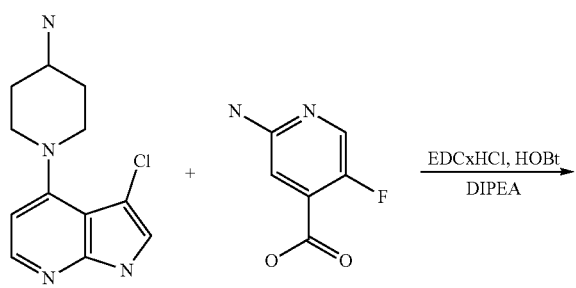

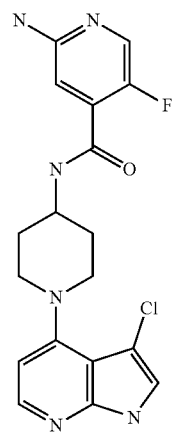

To a solution of 2-amino-5-fluoro-pyridine-4-carboxylic acid (66.0 mg, 0.43 mmol) in DMF (1 mL) at 0° C. was added EDC×HCl (70.0 mg, 0.36 mmol) and DIPEA (141 µL, 0.81 mmol) and left stirring for 30 minutes. Then HOBt× H$_2$O (52.0 mg, 0.34 mmol) and 1-(3-chloro-1H-pyrrolo[2,3-b]pyridin-4-yl)piperidin-4-amine (108.0 mg, 0.43 mmol) were added. The reaction was left stirred overnight at room temperature. Reaction mixture was diluted with water (10 mL) and product was precipitated. Crystals were filtered off and dried in vacuum drier at 65° C. for 3 h. Filtrate was extracted with EtOAc (4×5 mL). The combined organic layers were dried over Na$_2$SO$_4$, filtered and concentrated in vacuo to afford the crude. Crude was purified via Biotage purification device on 4 g KP-Sil Interchim column: DCM as weak solvent and E1 as strong solvent. The appropriate fractions have been collected to afford 2-amino-N-[1-(3-chloro-1H-pyrrolo[2,3-b]pyridin-4-yl)-4-piperidyl]-5-fluoro-pyridine-4-carboxamide (7.77 mg). LCMS: MW (calcd): 388.8; MS (ES$^+$, m/z): 389.47 (M+H)$^+$. $^1$H NMR (500 MHz, DMSO-d6) δ 11.81 (br. s., 1H), 8.51 (d, J=7.63 Hz, 1H), 8.06 (d, J=5.19 Hz, 1H), 7.92 (s, 1H), 7.45 (s, 1H), 6.47-6.64 (m, 2H), 6.03 (s, 2H), 3.94 (m, 1H), 3.50-3.64 (m, 2H), 2.87 (t, J=11.44 Hz, 2H), 1.96 (d, J=10.38 Hz, 2H), 1.72-1.87 (m, 2H) ppm.

Biological Examples

2. In Vitro Assays 2.1 ASK1/2 Biochemical Assays (IMAP Technology)

IMAP® technology provides a homogeneous assay applicable to a wide variety of kinases, phosphatases, and phosphodiesterases without regard for substrate peptide sequence. The assay is a simple mix-and-read procedure allowing accurate determination of enzyme activity. Based on the specific, high-affinity interaction of phospho groups with trivalent metal-containing nanoparticles (beads), IMAP is a generic, non-antibody-based platform to assess kinase, phosphatase, and phosphodiesterase activity. An enzyme reaction is performed using fluorescently labeled substrate. Addition of the IMAP Binding System stops the enzyme reaction and initiates binding of the beads to phosphorylated substrates. Binding of the substrate to the beads, which correlates to enzyme activity, can be detected using either FP or TR-FRET as a readout.

Apoptosis Signal-regulating Kinase (ASK1), also known as MAP3K5, is a member of the mitogen-activated protein kinase kinase kinase (MAP3K) family of kinases. It activates the Jnk and p38 pathways through the MAP2Ks MKK4/7 and MKK3/6 (respectively). This ASK1 IMAP assay uses the following IMAP peptide: RP7140-T2 (5TAMRA-GTFRAAIRRLAARRR-OH, SEQ ID NO: 1). The assay has been configured to run at Km for ATP (150 mM) so that it will be sensitive to ATP-competitive inhibitors. The final assay conditions are 150 mM ATP, 1 mM DTT, 200 nM peptide and 6 nM ASK1 (total protein). The binding reagent is made up in 100% A at a final dilution of 1:200.

Solutions:

KIT IMAP FP, Cat. No. R8127; Reaction Buffer-Tween (5× conc.), Molecular Devices, Cat. No. R7436; Diluted 1:5 with $H_2O$ and containing DTT (1 mM from 1M stock); Progressive Binding Buffer (PBB) A (5× conc.), Molecular Devices, Cat. No. R7282; Progressive Binding Reagent (PB Reagent), Molecular Devices, Cat. No. R7284; Enzyme Solution (containing 2× Ask1 in Reaction buffer); Substrate Solution (containing 2× peptide substrate in Reaction buffer, and 2×150 µM ATP in Reaction buffer); Bead Buffer (Progressive Binding Buffer A diluted 1:5 with $H_2O$); Bead Solution (Bead Buffer containing 1:200 Progressive Binding Reagent (2×))

Experimental 100 nL of test compound in 100% DMSO was added to 384-well plates. For a dose response experiment a 1 in 4 dilution of compound (25 µM top final concentration) was used. 3 µL of hASK1 (6 nM), hASK2 (25 nM) or rASK1 (15 nM) was added to each well except in the control well to which 3 µL buffer was added. 3 µL of substrate solution was added to each well and the plates were incubated for 4 h at room temperature. After which time 6 µL of IMAP™ Bead Solution (Progressive Binding Buffer A+PB Reagent; final dilution 1:100) was added to each well and spun for 1 minute at 1000 rpm. The plates were then incubated for 2 h at room temperature after which time the plates were read on a Perkin Elmer EnVision plate reader.

Data Analysis

Calculation of $IC_{50}$ data, curves and QC analysis was made by using Excel tools and GraphPadPrism software, v. 5.03. Briefly, individual concentration-effect curves are generated by plotting the logarithm of the tested concentration of tested compounds (X) vs. corresponding percent inhibition values (Y) using least squares (ordinary) fit. Up to ¼ points from high/low controls are allowed to be excluded, but only if values are >Avg.±1*SD. Fitting equation used for $IC_{50}$ calculation=log(inhibitor) vs. response–Variable slope (four parameters). Calculated results: Calc 1: mP value for FP measurement=1000*(S–G*P)/(S+G*P) where S=<detector 2 or FP-BodipyTAMRA_Ex531-Em579-optimized(1) channel 2>P=<detector 1 or FP-BodipyTAMRA_Ex531-Em579-optimized(1) channel 1>G=G-factor. Gain=100. Top constrain is used only if top values are not correctly calculated.

Minimum constrained if less than −30% I or greater than 30% I. Maximum constrained if less than 70% I or greater than 130% I. Z'-Factor Target>0.4. Hill Slope range 0.5 to 5.

Illustrative compounds of the invention were tested according to the method of Example 2.1. The results are shown below:

| Compound number | Inhibition ($pIC_{50}$) ASK1/ASK2 |
|---|---|
| 1 | 8.24/7.96 |
| 2 | 8.17/8.08 |
| 3 | 8.05/— |
| 4 | 8.46/8.19 |
| 5 | 8.43/— |
| 6 | 8.98/— |
| 7 | 8.24/— |

2.2 ASK1/2 Biochemical Assays (AlphaScreen Technology)

AlphaScreen Technology Description

ASK1 and ASK2 biochemical activities were also quantified using AlphaScreen technology which measures the degree of phosphorylation of a protein substrate (MKK7). AlphaScreen technology is based on the binding of a substrate to two types of beads, acceptor and donor. Binding to one bead is through the tag of the substrate protein. Binding of the second bead is through phosphospecific binding of antibody to the phosphosite of the substrate. This forms a sandwich, with the acceptor and donor beads in close proximity. When the donor beads are excited by light in the 680 nm range, a singlet oxygen is released and causes emission of light from the acceptor in the 620 nm range which can be detected using a suitable plate reader.

ASK1/2 AlphaScreen Assay Description

The ASK1/2 AlphaScreen assays were enabled by binding of full length inactive MKK7 protein to glutathione donor beads through the use of GST-tag. The phosphorylation site on MKK7 (Ser271/Thr275) is then recognised by a phosphospecific antibody. The phosphospecific antibody is bound to the AlphaScreen acceptor beads through a Protein-A interaction. Phosphorylation of MKK7 by ASK1 or ASK2 subsequently facilitates the bringing together of the donor and acceptor beads into close proximity whereupon the transfer of the singlet oxygen leads to the generation of the AlphaScreen signal.

ASK1/2 AlphaScreen Reagents, Conditions and Protocol

Full length human ASK1 protein with an N-terminal 6His-Avi tag.

Heterodimer of full length ASK1 protein with an N-terminal 6His-Avi tag (inactive enzyme where lysine 709 is replaced with methionine) and full length ASK2 protein with 6His-FLAG tag.

Human MKK7 inactive (Carna Bioscience, Cat. No. 07-147-10).

Phospho-MKK7 (Ser171/Thr275) antibody (Cell Signalling Technologies Cat. No. 4171).

Protein A acceptor beads (Perkin Elmer, Cat No. 6760137).

Glutathione donor beads (Perkin Elmer, Cat. No. 6765301).

Adenosine triphosphate, ATP (Promega, Cat No. V915B).

Reaction buffer: 50 mM Hepes, 150 mM NaCl, 10 mM MgCl2, 1 mM CHAPS, pH 7.2.

Stop buffer: 50 mM Hepes, 150 mM NaCl, 60 mM EDTA, 1 mM CHAPS, pH 7.2.

The assay was configured to run using the following conditions (final concentrations): 150 µM ATP; 400 nM MKK7; 0.8 nM ASK1 and 2 nM ASK2.

Experimental 100 nL of test compound (starting concentration 6 µM, 11 concentrations with 3 fold serial dilutions) in 100% DMSO was added to low volume 384 well plates. 2.5 µl of ASK1 or ASK2 was added to each well except in the control wells to which 2.5 μl buffer was added. 2.5 μl of MKK7 solution was added to all wells. The plate was incubated for 60 minutes at room temperature. Protein-A acceptor beads and phospho-specific antibody were incubated for 30 minutes and then 2.5 μl of Protein-A acceptor beads/phospho-specific antibody mix (2.5 μg/ml acceptor beads final concentration and 1/800 antibody final dilution) was added to each well. The plate was incubated for 30 minutes at room temperature and then 2.5 μl of GSH donor beads (10 μg/ml acceptor beads final concentration) was added to each well. The plate was incubated for a further 60 minutes at room temperature, following which the plate was read on a Perkin Elmer Enspire plate reader.

Data Analysis

Calculation of $IC_{50}$ data, curves and QC analysis were made by using Excel tools and GraphPadPrism software, v. 5.03. Briefly, individual concentration-effect curves were generated by plotting the logarithm of the tested concentration of tested compounds (X) vs. corresponding percent inhibition values (Y) using least squares (ordinary) fit. Fitting equation used for $IC_{50}$ calculation=log(inhibitor) vs. response–Variable slope (four parameters).

Illustrative compounds of the invention were tested according to the method of Example 2.2. The results are shown below:

| Compound number | Inhibition ($pIC_{50}$) ASK1/ASK2 |
|---|---|
| 1 | 8.72/7.71 |
| 2 | 8.9/— |
| 3 | 8.7/7.8 |
| 4 | 9.4/8.2 |
| 5 | 8.8/— |
| 6 | 8.98/— |
| 7 | 8.24/— |

2.3 ASK1/2 Cellular Assay

ASK1/2 activity in vitro was assayed by determining the quantity of phospho-MKK3 protein in $H_2O_2$-stimulated PBMCs, using western blot method. MKK3 was shown to be a direct substrate of ASK1/2 catalyzed phosphorylation in the p38 activation pathway.

2.3.1 Materials and Assay Conditions

Lymphoprep (Axis-Shield, Cat. No. 1114545)
Ammonium chloride lysate buffer pH 7.4 (10× concentrated):
  $NH_4Cl$—final conc. 1.5 M (Kemika, Cat. No. 0137407)
  $NaHCO_3$— final conc. 100 mM (Kemika, Cat. No. 1411007)
  $Na_2EDTA$—final conc. 10 mM (Sigma Aldrich; Cat. No. E-4884)
RPMI 1640 (Lonza Cat. No. BE12-115F/U1)
FBS (Sigma Cat. No. F7524, heat inactivated 30'/56° C.)
Dimethyl sulfoxide (DMSO) (Sigma, Cat. No. D2650)
Cell lysis buffer (pH 7.4): PBS+1% Triton X-100 (Sigma Aldrich; Cat. No. X100)—10 ml
  Phospho-Stop—1 tablet (Sigma, Cat. No. 4693124001)
  Protease Inhibitor—1 tablet (Sigma, Cat. No. 4906837001)
Hydrogen peroxide solution 3% w/w (Sigma Aldrich, Cat. No. H-6520)
PBS (Sigma Aldrich, Cat. No. P4417-100TAB)
Microplate, 96 well, pp, v-bottom, clear (Greiner bio-one; Cat. No. 651201)
Tissue culture plate, 6 well, flat bottom with low evaporation lid (Falcon, Cat. No. 353224)
50 mL falcon tube (TPP, Cat. No. 91050)
Pierce BCA Protein Assay Kit (Thermo Scientific, Cat. No. 23225)
Immulon® Microtiter™ 96-Well Plate 1B (Thermo Scientific, Cat. No. 3355)
Wes 12-230 kDa Master Kit (Protein Simple, Cat. No. PS-MK14)
MKK3 (D4C3) Rabbit mAb (Cell Signaling, Cat. No. 8535)
Phospho-MKK3 (Ser189)/MKK6 (Ser207) (D8E9) Rabbit mAb (Cell Signaling, Cat. No. 12280)

The assay was configured to run using the following conditions: Tested compounds concentration range: 1-0.0014 μM (7 three-fold serial dilutions); $H_2O_2$ concentration: 3 mM 2.3.2 Experimental To isolate the PBMCs from buffy coat, the buffy coat was diluted 1:1 in PBS, then the dilute buffy-coat (25 mL) was carefully pipetted on top of 20 mL of Lymphoprep in a falcon tube. The tubes were then spun for 35 min at 400×g. The upper plasma layer is then carefully removed leaving the layer containing the MNCs. The layer containing the MNCs is then transferred to a new tube, PBS is added up to a total volume of 50 mL and the tube is then spun for 10 minutes (200×g, 25° C.). The resulting pellet is then resuspended in 2 mL PBS, the washing step was repeated. The final pellets were resuspended in ammonium chloride lysate buffer up to 50 mL, mixed gently and centrifuged for 10 minutes (200×g, 25° C.), resuspended in 2-3 mL of cell medium and diluted up to 50 mL in cell medium. The cell density of a 1/20 dilution in cell medium was determined using an automated cell counter.

$10\times10^6$ PBMCs were seeded per well in 1 mL of RPMI 1640 cell medium supplemented with 10% FBS in 6-well plates. Seven sets of three-fold serial dilutions of compounds in DMSO starting from 1 mM in 96-well v-bottom plate were prepared. The DMSO compound solutions were diluted 100× in the cell medium. 200 μL of 100× diluted compound solution were added per well, control wells contained 200 μL of 1% DMSO prepared in cell medium. 7.5 mM $H_2O_2$ in cell medium was prepared and 800 μL was added to each well, except the negative control well to which 800 μL of cell medium was added. The cells were incubated for 30 min at 37° C., 5% $CO_2$, 95% humidity. The cells were transferred to 2 mL Eppendorf tubes and centrifuged for 10 minutes at 300×g at 4° C., they were then washed with 1 mL PBS, the cell pellet was resuspended in 100 μL of lysis buffer and incubated on ice for 30 minutes. After which time the cell lysates were centrifuged for 5 minutes at 10000×g at 4° C. and the supernatants were then stored at −20° C.

Samples were diluted 5× in cell lysis buffer and total protein concentration was determined in 96-well Immulon 1B plate using BCA Protein Assay Kit following manufacturer's instructions.

Western blot assay was performed using Protein Simple Wes Master Kit and device, following manufacturer's instructions. 0.5 mg/mL of total proteins was loaded per sample; phospho-MKK3 and MKK3 antibodies were diluted 300×.

Western blot results were analysed using Compass 2.7.1 software and phospho-MKK3 quantity was divided by MKK3 quantity for each sample. Percentages of inhibition were calculated by normalizing the data to controls using the following equation:

$$[(Sample-Low\ control)/(High\ control-low\ control)]*100$$

IC$_{50}$ values of compounds were determined by plotting percentages of inhibition and logarithm of compound concentrations using GraphPad Prism software, non-linear regression (curve fit), log (inhibitor) vs. response—Variable slope (four parameters).

Illustrative compounds of the invention were tested according to the method of Example 2.3. The results are shown below:

| Compound number | Inhibition (pIC$_{50}$) |
|---|---|
| 1 | 8.05 |
| 2 | 8.5 |
| 3 | 7.4 |
| 4 | 8.1 |
| 5 | 8.2 |
| 6 | 7.9 |
| 7 | 7.9 |

2.4. ASK1/2 Human Whole Blood Assay

ASK1/2 activity in vitro was assayed by determining the quantity of CCL2 cytokine produced in human whole blood stimulated with LPS using ELISA. It was described in the literature that CCL2 production was decreased in serum from ASK1 knock-out mice under nonstimulated and LPS-stimulated conditions.

2.4.1 Materials and Assay Conditions

RPMI 1640 (Lonza Cat. No. BE12-115F/U1)
Dimethyl sulfoxide (DMSO) (Sigma, Cat. No. D2650)
Lipopolysaccharide from *E. coli* (LPS) (Sigma, Cat. No. L4391)
Microplate, 96 well, pp, v-bottom, clear (Greiner; Cat. No. 651201)
Master block 96 well, 2 ml (Greiner, Cat. No. 780271)
Microplate, 96 well, ps, u-bottom, clear, with lid (Greiner, Cat. No. 650180)
50 mL falcon tube (TPP, Cat. No. 91050)
Immulon 2HB 96-well plate (Thermo Fisher Scientific, Cat. No. 3455)
Sucrose (Kemika, Cat. No. 1800408)
Streptavidin-HRP (Calbiochem, Cat. No. OR03L)
Sulphuric acid (Kemika, Cat. No. 1816501)
anti-hCCL2 antibody (R&D Systems, Cat. No. MAB679), dissolved in 1 ml of PBS
anti-hCCL2 detection antibody (R&D Systems, Cat. No. BAF279), dissolved in 1 ml of PBS
Recombinant hCCL2 (standard, R&D Systems, Cat. No. 366-6C)
Wash buffer (PBS+0.05% Tween-20)
   PBS (Sigma, Cat. No. P4417)
   Tween-20 (Sigma, Cat. No. P2287)
Substrate for 20 ml: 18 ml H$_2$O+2 ml 1M sodium acetate+200 µl TMB mix+2.5 µl 30% H$_2$O$_2$
   Sodium acetate (Kemika, Cat. No. 1441908)
   TMB mix (Sigma, Cat. No. T2885)
   Hydrogen peroxide (Merck, Cat. No. 1.08597)
Coating buffer (15 mM Na$_2$CO$_3$ (×H$_2$O)+35 mM NaHCO$_3$)
   Sodium carbonate (Sigma, Cat. No. S-2127)
   Sodium bicarbonate (Kemika, Cat. No. 1411007)
Assay buffer (PBS+0.05% Tween-20+1% BSA)
   Bovine Serum Albumin (BSA) (Sigma, Cat. No. A2153)

2.4.2 Experimental

Whole blood was collected on citrate anticoagulant. 100 µL was used for determination of cell count using automated cell counter.

300 µL of whole blood was added to a 2 mL master block 96-well plate. Six three-fold serial dilutions of compounds in DMSO were prepared starting from 10 mM in 96-well v-bottom plate. 0.6 µL of prepared compounds or 0.6 µL of DMSO (positive and negative control wells) from v-bottom plate were added to the master block plate with blood. 2 ng/mL LPS in culture medium without serum were prepared and 300 µL was added per well to the master block plate with blood for the test wells. 300 µL of culture medium was added to the negative control wells. The plate was incubated with whole blood overnight in CO$_2$ incubator (37° C., 5% CO$_2$, 95% humidity). The plate was then centrifuged for 7 minutes at 1500×g and the supernatants were transferred to a 96-well u-bottom plate for determination of CCL2 cytokine or the supernatants were stored at −20° C. for future testing.

The day before performing ELISA, the Immulon 2HB plate was coated with 100 µL per well of 250× diluted anti-hCCL2 antibody in coating buffer. The plate was then incubated at 4° C. overnight. The plate was washed three times with 300 µL per well of wash buffer and this was repeated after each step. 200 µL of blocking (assay buffer+5% sucrose) was added to each well and incubated for 60 minutes at 37° C. Seven sets of two-fold serial dilutions of hCCL2 standard in assay buffer were prepared starting from 2000 µg/mL, in duplicates. Blank wells were prepared containing only assay buffer. The test samples (supernatants) were added diluted 10 times in assay buffer to plate. All final volumes in plate were 100 µL. The plate was incubated for 60 minutes at 37° C. 100 µL per well of 500× diluted anti-hCCL2 detection antibody in assay buffer was added and the plate was incubated for 45 minutes at 37° C. 100 µL per well of 50 ng/mL streptavidin-HRP in assay buffer was added and the plate was incubated for 30 minutes at 37° C. 100 µL per well of the prepared substrate solution was added and the plate was incubated at room temperature, protected from light until blue colour developed in the wells. To stop the colour development 100 µL per well of 1M sulphuric acid was added. The plate absorbance was read at 450 nm on a plate reader.

2.4.3 Data Analysis

ELISA results (absorbance at 450 nm) were analysed using Microsoft Excel software. Average of blank was subtracted from all values. Standard curve was plotted with serial dilutions of standards (pg/mL) on the x-axis versus the corresponding absorbance values on the y-axis. Amount of cytokine in samples (pg/mL) was calculated from standard curve. Percentages of inhibition were calculated by normalizing the data to controls using following equation:

$$[(\text{Sample}-\text{Low control})/(\text{High control}-\text{low control})]*100$$

IC$_{50}$ values of compounds were determined by plotting percentages of inhibition and logarithm of compound concentrations using GraphPad Prism software, non-linear regression (curve fit), log (inhibitor) vs. response—Variable slope (four parameters).

3. In Vivo Assays

3.1 CFA (Complete Freunds Adjuvant) Induced Hypersensitivity in Rat Assessed Using Weight Bearing Method Intraplantar injection of Complete Freunds adjuvant (CFA) causes an inflammatory reaction which induces hypersensitivity and oedema, and mimics some aspects of clinical inflammatory pain. These effects can be investigated using equipment to measure weight bearing and plethysmometer.

3.1.1 Weight Bearing

Naive rats distribute their body weight equally between the two hind paws. However, when the injected (left) hind paw is inflamed and/or painful, the weight is re-distributed so that less weight is put on the affected paw (decrease in weight bearing on injured paw). Weight bearing through each hind limb was measured using a rat incapacitance tester (Linton Instruments, UK).

Rats were placed in the incapacitance tester with the hind paws on separate sensors and the average force exerted by both hind limbs was recorded over 4 seconds.

Base line weight bearing and paw volume readings were taken and hypersensitivity was induced via injection of CFA (Baseline weight bearing and paw volume recordings were taken prior to induction of insult. Inflammatory hypersensitivity was induced by intraplantar injection of CFA (100 μL of 1 mg/mL solution) intraplantar to the rats left hind paw.

Animals (Male, Sprague Dawley Rats (Charles River, UK), 212-260 g) were ranked and randomised to treatment groups according to the weight bearing CFA window in a Latin square design. Animals were treated with either Vehicle, Compound 1 10 mg/kg or Indomethacin 10 mg/kg (10 L/kg dose volume) 24 hours post CFA. Weight bearing was measured at 1, 2 and 4 hours post treatment. Weight-bearing (g) readings were taken for both right and left hind paws and the difference calculated. Data are expressed as % reversal of the hypersensitivity to pain (mean±s.e.m.). Paw Volume (mL1) readings were taken for the left hind paws. Data were expressed as % reversal of the oedema (mean±s.e.m.). The statistical analysis: was performed with repeated measures ANOVA followed by Planned comparison test using InVivoStat (invivostat.co.uk, Clark et al., 2012), $p<0.05$ considered significant.

Compound 1 and Indomethacin (10 mg/kg) significantly inhibited the hypersensitivity response at all time points tested post administration.

3.2 MIA Induced Hyperalgesia in the Rat—In Vivo Chronic Pain Model

Intra-articular administration of Monosodium Iodoacetate (MIA) in the ipsilateral knee of Sprague Dawley rats leads to development of a robust and long-lasting hyperalgesia and allodynia associated initially with an inflammatory response. The development of these signs in this animal model are believed to be clinically relevant; reflecting the symptoms displayed by patients presenting with chronic inflammatory pain associated with underlying conditions such as osteoarthritis (OA) or rheumatoid arthritis (Bove S E et al., Osteoarthritis Cartilage 2003; 11 (11): 821-30; Fernihough J, et al., Pain 2004; 112 (1-2): 83-93; Kalbhen D A. J Rheumatol 1987; 14 Spec No: 130-1).
Weight Bearing Naive rats distribute their body weight equally between the two hind paws. However, when the injected (left) hind knee is inflamed and/or painful, the weight is re-distributed so that less weight is put on the affected limb (decrease in weight bearing on injured limb). Weight bearing through each hind limb is measured using a rat incapacitance tester (Linton Instruments, UK).

Osteoarthritis (OA) in rats ((Sprague Dawley, male, groups of 10) was induced via injection of MIA solution (Sigma, 12512), 25 μL of 80 mg/mL, (2 mg) into the knee joint of the left hind leg. Weight bearing was assessed on Days 3, 5, 7, 9, 12 & 16, following injection of MIA, for development of chronic pain. At Day 3 weight bearing measurements were taken and animals were ranked and randomised to treatment groups according to their MIA window in a Latin square design.

Animals were treated with Compound 1 10 mg/kg in 0.5% Methylcellulose or Vehicle (0.5% Methylcellulose) 10 mL/kg p.o. on day 3 and then daily up to day 16. Weight bearing measurements were taken 1, 2 and 4 hours post dosing on day 3 and 2 hours post dosing on days 5, 7, 9, 12 & 16.

Weight bearing (g) readings were taken for both right and left hind paws and the difference calculated. Data are expressed as % ratio ipsilateral/contralateral ((WB left/WB right)*100) (mean±s.e.m.)

Calculation: Ipsilateral reading/contralateral reading x 100. Naïve WB difference−pre dose WB difference was defined as the MIA window.

Statistical analysis: Repeated measures ANOVA followed by Planned comparison test using InVivoStat (invivostat.co.uk), ($p<0.05$ considered significant). Data were analysed by comparing treatment groups to vehicle control group at each time point.

A significant and marked reversal of hypersensitivity was seen with Compound 1 when dosed at 10 mg/kg from 1 hours post dose, until day 12 (9 days post dose). Compound 1 given at 10 mg/kg showed significant reversal when compared to vehicle at each time point, comparable to the positive control celecoxib.

3.3 $CCl_4$ Model of Liver Fibrosis—Protocol 1

The aim of this study was to assess a model of liver fibrosis by $CCl_4$ intoxication. The onset of the disease and the effect of potential positive references are evaluated by assessing liver fibrosis by exploring histology, biochemistry, imaging and gene expression at different time-points. Starkel P., Animal models for the study of hepatic fibrosis, Best practice & Research Clinical Gastroenterology 25: 319-333, 2011

3.3.1 Study Groups

The study is performed using 5 week old male BalbC J mice (Janvier Lab).

| Groups | Protocol | n* | Treatment | Sacrifice |
|---|---|---|---|---|
| Sham | Olive oil IP twice/week | 10 | | 3 weeks |
| $CCl_4$ | 0.6 mL/kg IP Twice/week | 10 | | 3 weeks |
| Sham | Olive oil IP twice/week | 10 | | 6 weeks |
| $CCl_4$ | 0.6 mL/kg IP Twice/week | 10 | | 6 weeks |
| $CCl_4$ | 0.6 mL/kg IP Twice/week | 10 | Test compound 30 mg/kg, b.i.d., p.o. | 6 weeks |
| $CCL_4$ + valproic acid | 0.6 mL/kg IP Twice/week | 10 | Positive control (Valproic acid) ad libitum in drinking water 0.4% | 6 weeks |

3.3.2 Materials $CCl_4$: Carbon tetrachloride ACROS 99.8% CAS=56-23-5 Lot A0293900
Olive oil, SIGMA 01514-500 mL Lot #BCBQ4885V
colF (ImmunoChemistry Technologies), ref 6346 Lot 13Y39 Exp 05/2017
    stock solution to be diluted in 100 μL of DMSO (6.8 mM) and stored at 4° C.
    injection of 1:170 dilution in ppi water to animal 15 min before imaging (100 μL, sinus i.v.)

$CCl_4$ was diluted at ½ in olive oil and administered IP twice per week at 0.6 mL/kg.

3.3.2 Samples and Results

Blood is collected in serum tubes and samples were centrifuged at 3000 t/min for 5 min and frozen at −20° C. for AST, ALT, ALP and total bilirubin evaluations. A sample of the liver right median lobe is also taken and quickly placed in Eppendorf tubes (2 mL round bottom) with 1 mL of RNAlater (safe lock tubes) stored at 4° C.

The liver is harvested and weighed. Ex vivo imaging of colF binding in liver is performed immediately (Bruker Xtreme). Livers are placed into formaldehyde (vial 25 mL-60 cc) for histological evaluation for aSMA and col I IHC quantification.

The spleens are weighed for future analysis.

A panel of 9 fibrosis genes are used for gene expression analysis.

3.4 $CCl_4$ Model of Liver Fibrosis—Protocol 2

The aim of this study was to assess a model of liver fibrosis by $CCl_4$ intoxication. The onset of the disease and the effect of potential positive references are evaluated by assessing liver fibrosis by exploring histology, biochemistry, imaging and gene expression at different time-points. Starkel P., Animal models for the study of hepatic fibrosis, Best practice & Research Clinical Gastroenterology 25: 319-333, 2011

3.4.1 Study Groups

The study is performed using 8 week old male BALB/c mice (Charles River, Italy).

| Group | N | Challenge/IP route | Vehicle | Treatment | Route and frequency of treatment | Treatment Schedule |
|---|---|---|---|---|---|---|
| 1 | 10 | Negative | — | — | — | — |
| 2 | 10 | $CCl_4$ IP (0.6 mL/kg) 2 × week | MC 0.5% + 1 eq HCl. 98.9% dist. water | Vehicle | PO BID | D 21-D 41 |
| 3 | 10 | D 0-D 38 | MC 0.5% | Compound 1 5 mg/kg | PO QD | |
| 4 | 10 | | MC 0.5% | Compound 1 15 mg/kg | PO QD | |
| 5 | 10 | | MC 0.5% | Compound 1 15 mg/kg | PO BID | |

3.4.2 Materials $CCl_4$ (liquid) will be added to olive oil at a concentration of 0.06 mL/mL. The solution will be administered IP at the dose of 0.6 mL/kg. Application volume will be 10 mL/kg.

The test compound will be dissolved/suspended in Methylcellulose (MC 0.5%).

3.4.3 Samples and Results

For steady state PK sampling blood will be collected in He-Lithium tubes to generate plasma. All blood samples will be processed for plasma by centrifugation (5,000 rpm for 10 minutes at 4° C.) within 30 minutes of collection. Samples are then stored at −80° C. until analysis.

Final blood samples will be collected into $K_2$EDTA micro tubes by cutting the v. jugularis. All blood samples will be processed for plasma by centrifugation (3500 rpm for 10 minutes at 4° C.) within 30 minutes of collection. Plasma from each blood sample stored at −80° C. until analysis.

The liver is harvested and portions of the left lateral lobe are stored for RNA gene expression analysis, section of OH proline measurement, and the rest placed in 10% formalin for histopathological evaluation.

A panel of 5 fibrosis genes (Col1, Timp1, Pai1, Snail1, Acta2) are used for gene expression analysis.

3.5 Methionine and Choline Deficient Model of Steatohepatitis and Fibrosis

MCD is a new mouse model of steatohepatitis and fibrosis induced by a diet: Methionine and Choline-Deficient (MCD). (Wehr et al 2013 J immunol, 190(10):5226-36; Baeck et al., 2014 Hepatology, 59(3):1060-72; Gautheron et al, 2014 EMBO, 6(8):1062-74).

3.5.1 Study Groups and Dose Regimen

C57BL/6 mice from (Janvier Labs (France)) are divided into groups as set out below, the mice are 8 weeks (>20 grs) at the initiation of the induction phase

| Diet/Groups | Project | n | Frequency & route | Vehicle | Aspect |
|---|---|---|---|---|---|
| Control diet | Ref group | 10 | BID p.o. | PEG200/MC (25/75) + 1eqHCl | |
| MCD diet | Ref group | 10 | BID p.o. | PEG200/MC (25/75) + 1eqHCl | |
| MCD diet | Test compound | 10 | BID p.o. | PEG200/MC (25/75) | Homogenous suspension |

3.5.2 Materials and Compounds

MCD diet w/o choline & Methionine Ref EFTD.90262 MCD mod. batch 8206423, Ssniff, Soest, Germany—
Methyl cellulosis 0.5%, VWR,
PEG 400: P3265, Sigma
Cryomold® Standard 25×20×5 mm (Sakura Finetec, 4557)
O.C.T.™ Compound cryomold (Sakura Finetec, 4583)
Formalin for sample preservation—4% buffered with MetOH

3.5.3 Compound Preparation

Compounds are dissolved/suspended in appropriate vehicle (see table above), under agitation. After preparation, solutions/suspensions are kept at room temperature in dark under constant magnetic stirring. When dosed 10 mL/kg volume is used and the concentration of the solution is adjusted according to the weight of the animal.

3.5.4 Protocol

The induction phase is 3 weeks. No fasting glucose is given. Mice are given either the MCD control diet or the MCD diet.

During the treatment phase the mice are maintained on the MCD control diet or MCD diet as in induction phase. The mice are randomly assigned to a treatment group according to their body weight in order to ensure a homogenous repartition. The mice are dosed once or twice daily with the test compound during the evaluation phase

3.6 Prophylactic Bleomycin Induced Pulmonary Fibrosis 14-Day Mice Model

The aim of the study is to test the efficacy of a test compound at three different doses in a 14-day model of bleomycin induced pulmonary fibrosis in mice.

3.6.1 Animals

This study is carried out on $C5^27BL/6N$ male mice, supplied by Charles River, Italy, which are acclimatized for at least 5 days in an environment maintained at 22° C., at 55% relative humidity, with 15-20 air changes per hour under light cycles of 12 h. Mice pelleted food and water are provided ad libitum.

At least one day prior to start of experiment, all animals are allocated randomly into groups as indicated in the table below.

All animal related research is conducted in accordance with 2010/63/EU and National legislation regulating the use of laboratory animals in scientific research and for other purposes (Official Gazette 55/13).

3.6.2 Study Groups

| Groups | Purpose | n | Dose | Treatment schedule Days (Frequency) | Route | Vehicle |
|---|---|---|---|---|---|---|
| 1 PBS + Vehicle | control | 15 | — | D 0-D 14 (BID) | NA | NA |
| 2 BLM + Vehicle | control | 15 | — | D 0-D 14 (BID) | PO | PEG/MC |
| 3 BLM + Pirfenidone | control | 15 | 50 mg/kg | D 0-D 14 (BID) | PO | 0.1% Natrosol |
| 4 BLM + test compound | Active | 15 | 1 mg/kg | D 0-D 14 (BID) | PO | PEG400/MC 0.5% 20/80 (v/v) |
| 5 BLM + test compound | Active | 15 | 3 mg/kg | D 0-D 14 (BID) | PO | PEG400/MC 0.5% 20/80 (v/v) |
| 6 BLM + test compound | Active | 15 | 10 mg/kg | D 0-D 14 (BID) | PO | PEG400/MC 0.5% 20/80 (v/v) |
| 7 BLM + test compound satellite for PK | Active | 10 | 10 mg/kg | D 0-D 7 (BID) | PO | PEG400/MC 0.5% 20/80 (v/v) |

3.6.3 Materials

The solvent for the test solutions is prepared by adding 0.5 g of hydroxyethylcellulose (Natrosol) into 500 mL Aqua distillate (0.1%) under continuous stirring without heating for 5 h on a magnetic stirrer.

Anesthetic solution is prepared by adding 1 mL of Narketan (Narketan 10, Vetoquinol, Bern, Switzerland, 03605877535982) and 0.5 mL of Rompun (Rompun, 2%: Bayer, Leverkusen, Germany) into 9 mL saline. The resulting solution is administered at 10 mL/kg.

To prepare a solution for intranasal challenge (i.n.) challenge, 0.8 mg/mL stock solutions of bleomycin (Bleomycin sulphate, Enzo Life Sciences, Inc., USA; CAS No. 9041-93-4; Cat. No. BML-AP302-0010) are thawn and diluted in 330 µL of saline.

Prior to i.n administration, mice are anesthetized i.p. with the anesthetic solution described above.

Fresh pirfenidone formulation is prepared daily in 0.1% Natrosol formulations to a final concentration of 5 mg/mL. Before dosing, animals are weighed and the Pirfenidone amount administered is adjusted accordingly to individual weights corresponding to 10 mL/kg body weight, twice daily p.o., with 7.5 h interval between two administrations.

Finally, test compound solutions are prepared by dissolving the suitable amount of said test compound in PEG 400 (20% of the final volume) then MC 0.5% (80% of the final volume) to reach final concentrations of 1 mg/mL, 0.3 mg/mL and 0.1 mg/mL, thus yielding compound for doses of 10 mg/kg, 3 mg/kg and 1 mg/kg. Prior to dosing, animals are weighed and the amount administered adjusted accordingly to individual weights.

The application volume of the test doses corresponds to 10 mL/kg body weight, and the test compounds are administered p.o. twice daily, with 7.5 h interval between two administrations.

3.6.4 Study

Animals are examined clinically twice daily. List of clinical signs and parameters are indicated in human endpoints table. Animals are weighed daily starting from DO.

On day 14, two hours post dosing with pirfenidone or test compound, mice are sacrificed by anesthetic overdose.

The lungs are excised and weighed individually. For all groups: the whole superior right lung lobe is placed into a Precellys tube containing silica beads and immediately snap frozen in liquid nitrogen and subjected to gene expression analysis.

All remaining lungs are placed into marked bottles containing 10% buffered formalin for further histopathological evaluation.

3.6.5 Sample Analysis, Data Processing and Statistical Evaluation

Body weight data and lung weight data are processed using MS Excel. Statistical analysis and graphical presentation are performed using GraphPad Prism software (version 5.04).

One-way ANOVA or Mann-Whitney test are employed for lung weights.

Two-way ANOVA are employed for body weight changes.

Differences between groups will be considered statistically significant when p<0.05.

For histopathological evaluation, whole lungs (except sampled superior right lung) are embedded in paraffin and stained with Mallory's trichrome.

Pulmonary histological changes are assessed using Matsuse modification of Ashcroft score (Ashcroft et al., 1988; Matsuse et al., 1999). Statistical analysis and graphical presentation is performed using GraphPad Prism software (version 5.04). Mann-Whitney test is employed.

Differences between groups will be considered statistically significant when p<0.05.

| | Ashcroft Score |
|---|---|
| 1 | Normal lungs (no fibrosis) |
| 2 | Minimal fibrotic thickening of alveolar or bronchial walls (network of fine collagen fibrils) |
| 3 | Moderate fibrotic thickening of walls without obvious damage to lung architecture |
| 4 | Fibrosis with damage of pulmonary structure (coarse fibrous bands or small fibrous masses, intra-alveolar collagen fibrils) |
| 5 | Large fibrous area with svere distortion of lung structure |

3.6.6 PK Analysis—Group 7

3.6.6.1 Protocol

Animals in group 7 (n=10) are included for PK study only and are not be subjected to clinical sign scoring.

These animals are induced with the disease at the start of treatment at day 0 and are sequentially sacrificed on day 7 at 1 h, 3 h, 6 h, 8 h, 24 h after the first administration of test compound.

A blood sample (50 μL) is collected from the tail vein into Li-heparin anticoagulant tubes for each time point and kept on ice until separation. Within maximum 30 min after collection, blood samples are centrifuged at 2000 g for 10 min at 4° C. and the resulting plasma samples are aliquoted into polypropylene tubes (1×25 μL). The samples are stored frozen at −20° C. until analysis.

The lung tissue is collected at sacrifice after blood sampling for each animal, then weighed and placed into polypropylene tubes prior to freezing. The samples are stored frozen at −80° C. until analysis.

3.6.6.2 Plasma Concentration and Pharmacokinetic Analysis

Plasma and lung concentrations are measured via LC-MS/MS. Samples are prepared for LC-MS/MS analysis via protein precipitation. The plasma concentrations measured below the lower limit of quantification (LLOQ) are reported as below the limit of quantification (BLQ).

The test compound concentrations in plasma are expressed in ng/mL.

Mean plasma concentrations are calculated. For mean calculation, the concentrations below the LLOQ are set to zero. Therefore, mean values may be BLQ. Standard deviation (SD), standard error of the mean (SE) and coefficient of variation (CV, %) are tabulated when at least three plasma concentration values are above the LLOQ.

Non-compartmental analysis on individual plasma concentrations is performed using Phoenix™ WinNonlin® 6.3 (Pharsight Corporation) to determine at least, the following pharmacokinetic parameters:

Maximum plasma concentration, Cmax (μg/mL) with the corresponding time, tmax (h), Area under the plasma concentration versus time curve up to the last quantifiable concentration $AUC_{0-t}$ or up to 24 h $AUC_{0-24h}$ (μg·h/mL) (if compound is quantifiable up to 24 h postdose), and/or up to infinity $AUC_{0-\infty}$, (μg·h/mL) is calculated according to the linear up/log down trapezoidal rule. Partial AUC may be calculated if deemed necessary. Concentrations below the limit of quantification (BLQ) are set to zero. No AUC is calculated if there are less than three quantifiable time points. AUC0-∞ is considered if % AUCextra<20%.

Apparent terminal elimination half-life, t1/2 (h) is only reported if three or more time points, excluding tmax is used for linear regression, and if the adjusted $R^2$>0.80.

Normalized AUC and Cmax dose.

Mean pharmacokinetic parameters are calculated. Standard deviation (SD) and coefficient of variation (CV, %) are tabulated if at least three values are available.

3.7 CIA Model

3.7.1 Materials

Complete Freund's adjuvant (CFA) and incomplete Freund's adjuvant (IFA) are purchased from Difco. Bovine collagen type II (CII), lipopolysaccharide (LPS), and Enbrel are obtained from Chondrex (L'Isle-d'Abeau, France), Sigma (P4252, L'Isle-d'Abeau, France), Wyeth (25 mg injectable syringe, France) Acros Organics (Palo Alto, Calif.), respectively. All other reagents used are of reagent grade and all solvents are of analytical grade.

3.7.2 Animals

Dark Agouti rats (male, 7-8 weeks old) are obtained from Harlan Laboratories (Maison-Alfort, France). Rats are kept on a 12 h light/dark cycle (0700-1900). Temperature is maintained at 22° C., and food and water are provided ad libitum.

3.7.3 Collagen Induced Arthritis (CIA)

One day before the experiment, CII solution (2 mg/mL) is prepared with 0.05 M acetic acid and stored at 4° C. Just before the immunization, equal volumes of adjuvant (IFA) and CII are mixed by a homogenizer in a pre-cooled glass bottle in an ice water bath. Extra adjuvant and prolonged homogenization may be required if an emulsion is not formed. 0.2 mL of the emulsion is injected intradermally at the base of the tail of each rat on day 1, a second booster intradermal injection (CII solution at 2 mg/mL in CFA 0.1 mL saline) is performed on day 9. This immunization method is modified from published methods (Jou et al. 2005; Sims et al. 2004).

3.7.4 Study Design

The therapeutic effects of the compounds are tested in the rat CIA model. Rats are randomly divided into equal groups and each group contains 10 rats. All rats are immunized on day 1 and boosted on day 9. Therapeutic dosing lasted from day 16 to day 30. The negative control group is treated with vehicle and the positive control group with Enbrel (10 mg/kg, 3×/week, s.c.). A compound of interest is typically tested at 4 doses, e.g., 0.3, 1, 3, and 10 mg/kg, p.o.

3.7.5 Clinical Assessment of Arthritis

Arthritis is scored according to literature-described methods (Khachigian 2006 Nat Protoc. 2006; 1(5):2512-6; Lin et al. 2007, Br J Pharmacol, 150, pp 862-872; Nishida et al. 2004, Arthritis and Rheumatism, 50(10), pp 3365-3376). The swelling of each of the four paws is ranked with the arthritic score as follows: 0-no symptoms; 1-mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al. 2004).

To permit the meta-analysis of multiple studies the clinical score values may be normalised as follows:

AUC of clinical score (AUC score): The area under the curve (AUC) from day 1 to day 14 is calculated for each individual rat. The AUC of each animal is divided by the average AUC obtained for the vehicle in the study from which the data on that animal is obtained and multiplied by 100 (i.e., the AUC is expressed as a percentage of the average vehicle AUC per study).

Clinical score increase from day 1 to day 14 (End point score): The clinical score difference for each animal is divided by the average clinical score difference obtained for the vehicle in the study from which the data on that animal is obtained and multiplied by 100 (i.e., the difference is expressed as a percentage of the average clinical score difference for the vehicle per study).

3.7.6 Change in Body Weight (%) after Onset of Arthritis

Clinically, body weight loss is associated with arthritis (Rall & Roubenoff 2004 Rheumatology (Oxford); 43(10): 1219-23; Shelton et al. 2005 Pain; 116(1-2):8-16; Walsmith et al. 2004 J Rheumatol.; 31(1):23-9). Hence, changes in body weight after onset of arthritis can be used as a non-specific endpoint to evaluate the effect of therapeutics in the rat model. The change in body weight (%) after onset of arthritis is calculated as follows:

$$\text{Mice: } \frac{\text{Body Weight (week 6)} - \text{Body Weight (Week 5)}}{\text{Body Weight (Week 5)}} * 100\%$$

$$\text{Rats: } \frac{\text{Body Weight (week 4)} - \text{Body Weight (Week 3)}}{\text{Body Weight (Week 3)}} * 100\%$$

3.7.7 Radiology

X-ray photos are taken of the hind paws of each individual animal. A random blind identity number is assigned to each of the photos, and the severity of bone erosion is ranked by two independent scorers with the radiological Larsen's score system as follows: 0—normal with intact bony outlines and normal joint space; 1—slight abnormality with any one or two of the exterior metatarsal bones showing slight bone erosion; 2-definite early abnormality with any three to five of the exterior metatarsal bones showing bone erosion; 3-medium destructive abnormality with all the exterior metatarsal bones as well as any one or two of the interior metatarsal bones showing definite bone erosions; 4-severe destructive abnormality with all the metatarsal bones showing definite bone erosion and at least one of the inner metatarsal joints completely eroded leaving some bony joint outlines partly preserved; 5-mutilating abnormality without bony outlines. This scoring system is a modification from literature protocols (Bush et al. 2002, Arthritis and Rheumatism, 46(3), 802-805; Jou et al. 2005, Arthritis Rheum, 52(1), 339-44; Salvemini et al. 2001, Arthritis Rheum, 44(12), 2909-21; Sims et al. 2004, Arthritis Rheum, 50(7), 2338-46).

3.7.8 Histology

After radiological analysis, the hind paws of mice are fixed in 10% phosphate-buffered formalin (pH 7.4), decalcified with rapid bone decalcifier for fine histology (EUROBIO, Les Ulis, France) and embedded in paraffin. To ensure extensive evaluation of the arthritic joints, at least four serial sections (5 µm thick) are cut and each series of sections are 100 µm in between. The sections are stained with hematoxylin and eosin (H & E). Histologic examinations for synovial inflammation and bone and cartilage damage are performed double blind. In each paw, four parameters are assessed using a four-point scale. The parameters are cell infiltration, pannus severity, cartilage erosion and bone erosion. Scoring is performed as follows: 1-normal, 2-mild, 3-moderate, 4-marked. The four scores are summed together and represented as an additional score, namely the 'RA total score'.

3.7.9 Micro-Computed Tomography (µ/CT) Analysis of Calcaneus (Heel Bone)

Bone degradation observed in RA occurs especially at the cortical bone and can be revealed by µCT analysis (Oste et al. 2007; Sims et al. 2004). After scanning and 3D volume reconstruction of the calcaneus bone, bone degradation is measured as the number of discrete objects present per slide, isolated in silico perpendicular to the longitudinal axis of the bone. The more the bone is degraded, the more discrete objects are measured. One thousand slices, evenly distributed along the calcaneus (spaced by about 10.8 µm), are analyzed.

3.7.10 Steady State PK

At day 7 or later, blood samples are collected at the retro-orbital sinus with lithium heparin as anti-coagulant at the following time points: predose, 1, 3 and 6 h. Whole blood samples are centrifuged and the resulting plasma samples are stored at −20° C. pending analysis. Plasma concentrations of each test compound are determined by an LC-MS/MS method in which the mass spectrometer is operated in positive electrospray mode. Pharmacokinetic parameters are calculated using WinNonlin® (Pharsight®,

3.8 MAB Model

The MAB model allows a rapid assessment of the modulation of an RA-like inflammatory response by therapeutics Khachigian, 2006. DBA/J mice are injected i.v. with a cocktail of mAbs directed against collagen II. One day later, compound treatment is initiated. Three days later, mice receive an i.p. LPS injection (50 μg/mouse), resulting in a fast onset of inflammation. Compound treatment is continued until 10 days after the mAb injection. Inflammation is read by measuring paw swelling and recording the clinical score of each paw. The cumulative clinical arthritis score of four limbs is presented to show the severity of inflammation. A scoring system is applied to each limb using a scale of 0-4, with 4 being the most severe inflammation.

0 Symptom free
1 Mild, but definite redness and swelling of one type of joint such as the ankle or wrist, or apparent redness and swelling limited to individual digits, regardless of the number of affected digits
2 Moderate redness and swelling of two or more types of joints
3 Severe redness and swelling of the entire paw including digits
4 Maximally inflamed limb with involvement of multiple joints

3.9 In Vivo Menisectomized (MNX) Rat Model

3.9.1 In Vivo Efficacy in the Rat MNX Model

In vivo efficacy was studied in a female Lewis meniscectomised rat (MNX) model. The MNX rat model is a well-validated disease model of osteoarthritis (Bendele, 2001, J Musculoskel Neuron Interact, 1(4), 377-85; Janusz et al., 2002, Osteoarthr Cartilage, 10, 785-91; Pritzker et al., 2006, Osteoarthr Cartilage, 14, 13-29).

3.9.2 Surgery and Dosing

Osteoarthritis is induced by meniscectomy at day 0 (DO) in the right leg of each rat by a transection of the medial collateral ligament and 4 mm of ligament are removed. Internal part of the meniscus is transected vertically into two flaps which are pushed to the front and the back of the synovial cavity. Sham animals undergo only anaesthesia, skin and muscle incision then suture. On day 1, rats are randomly assigned to a treatment group (n=20 per group) according to their body weight, in order to have a homogenous distribution. From C2 to D21, rats are dosed per os (po) once daily (qd) or twice a day (bid) with compounds formulated in methylcellulose (MC) 0.5% or in HPβCD 10% pH3.0.

3.9.3 Steady-State PK Determination (ssPK)

After at least 7 days of treatment, blood is sampled at 4 time points post administration: 0, 1, 3 and 6 h (and assuming 24 h is equal to the pre-dose sample), in order to determine steady-state plasma exposure.

3.9.4 Histology

At sacrifice, the right tibia of each rat is collected and processed for histological analysis. After 48 h of fixation in 4% formaldehyde, tibias are decalcified in Osteosoft for 7 days, and cut into 2 half parts prior to embedding face to face in paraffin. Five series of sections are cut at 200 μm intervals, covering about 1.5 mm of the middle part of the bone. One series of slides is stained with Safranin O and light green for morphological evaluation and OARSI scoring. The other series of slides are mounted with DAPI for chondrocyte density measurement.

The extent of cartilage injury reflecting osteoarthritis in the tibial plateau is evaluated and scored using the OARSI method based on the grading and the staging of cartilage lesion (Pritzker et al, 2006). The OARSI scoring is assessed in a blinded manner by two different readers. For each tibia, one score is attributed as the median of the OARSI score of the 5 sections.

For statistical analysis, medians of groups are compared with a stratified Kruskal-Wallis test followed by Dunnett multiple comparison post hoc test.

Significance levels: ns: not statistically significant; *p<0.05; p<0.01; *p<0.001 versus MNX-vehicle. Statistical analyses are done on all groups of the studies.

3.10—Diet-Induced Mouse Model of Non-Alcoholic Steatohepatitis (NASH)

This model uses a choline-deficient, L-amino acid-defined, high-fat diet (CDAHFD) consisting of 60 kcal % fat and 0.1% methionine to induce NASH.

3.10.1 Study Groups and Dose Regimen

C57/BL6 mice (Charles River) are divided into groups as set out below, the mice are 8 weeks (>20 grs) at the initiation of the induction phase.

| Diet/Groups | Project | N | Dose | Frequency & route | Vehicle |
| --- | --- | --- | --- | --- | --- |
| Control diet | Vehicle | 10 | n/a | BID p.o. | MC 0.5% + 1 eq HCl, 98.9% dist. water |
| CDAHFD diet | Vehicle | 10 | n/a | BID p.o. | MC 0.5% + 1 eq HCl, 98.9% dist. water |
| CDAHFD diet | Compound 1 | 10 | 5 mg/kg | QD p.o. | MC 0.5% |
| CDAHFD diet | Compound 1 | 10 | 15 mg/kg | QD p.o. | MC 0.5% |
| CDAHFD diet | Compound 1 | 10 | 15 mg/kg | BID p.o. | MC 0.5% |

3.10.2 Materials and Compounds

CDAHFD; Research Diets Inc., Ref. No. A06071302
Control diet: normal diet (VRF 1, P), Special Diets Services

3.10.3 Treatment Protocol

Induction Phase: For 4 Weeks
In order to induce a non-alcoholic steatohepatitis (NASH), animals will be fed with choline-deficient, L-amino acid-defined, high-fat diet (CDAHFD).
Treatment Phase: For 6 Weeks
Mice were randomly assigned to a treatment group and treated according to schedule presented in the Table above until the evaluation phase.

3.10.4—Sampling

Steady state PK sampling—Blood will be collected in K2-EDTA tubes to generate plasma. All blood samples will be processed for plasma by centrifugation (5,000 rpm for 10 minutes at 4° C.) within 30 minutes of collection. Plasma from each blood sample will be quickly frozen in liquid nitrogen and stored in a freezer maintained at −80° C. until analysis.

Final blood sample—Blood will be collected in tubes for serum preparation containing protease inhibitors. All blood samples will be processed by centrifugation (3,500 rpm for 15 minutes at 4° C.). Aliquots of obtained serum samples will be stored frozen at −80° C. until further analysis.

Tissue samples: The liver is harvested and portions of the left lateral lobe are stored for RNA gene expression analysis, TG assay, sectioned for OH proline measurement, and the rest placed in 10% formalin for histopathological evaluation. Histopathological evaluation includes sections stained with Sirius red to evaluate extent of fibrosis, and sections stained with F4/80 to assess macrophage accumulation.

A panel of 6 fibrosis genes (Col1A1, Timp1, Pai1, CTGF, TGFβ and Acta2), inflammation genes (TNFα, IL10 and CCL2) and 2 house keeping genes are used for gene expression analysis.

3.10.5 Results

Compound 1 when tested in this model showed a significant effect on at least the highest doses tested on the expression levels of Pai1, TIMP1, CTGF, and TGF (in the fibrosis gene panel, (FIG. 3) and on all three genes in the inflammation panel (FIG. 4). Additionally it showed a significant effect on hydroxyproline levels at 15 mg/kg/QD and 15 mg/kg/BID (FIG. 5), a significant effect on the Sirius red fibrosis quantification at 15 mg/kg/QD and 15 mg/kg/BID (FIG. 6), and a significant effect on the F4/80 quantification at 15 mg/kg/BID (FIG. 7).

4 CYP Inhibition

The inhibitory potential of a test compound for human cytochrome P450 isoenzymes (CYP1A2, 2C9, 2C19, 2D6 and 3A4) is assessed using cDNA-expressed human cytochrome P450 isoenzymes and non-fluorescent substrates which are metabolized to fluorescent metabolites.

Compounds are tested at 3.3 and 10 µM, with a final DMSO concentration of 0.3%. Compounds are incubated for 15 min with enzyme before the cofactor-substrate mix is added. Final reaction concentrations in cofactor mix for the CYP3A4 (BD Biosciences, 456202), CYP2C9 (BD Biosciences, 456258), CYP2C19 (BD Biosciences, 456259) and CYP1A2 (BD Biosciences, 456203) assays are: 0.4 U/mL glucose-6-phophate-dehydrogenase (G6PDH, Roche, 10165875001), 3.3 mM $MgCl_2$ (Sigma, M2670), 3.3 mM D-glucose-6-phosphate (Sigma, G7879) and 1.3 mM NADP+ (Sigma, N0505). For CYP2D6 (BD Biosciences, 456217), final reaction concentrations in the assay are 0.4 U/ml G6PDH, 0.41 mM $MgCl_2$, 0.41 mM D-glucose-6-phosphate and 8.2 µM NADP+. The concentrations of enzyme and substrate are reported in 0. After an incubation period, the reaction is stopped by adding a stop solution. For experiments with DBF as substrate, a 2 N NaOH stop solution is used, while for all other substrates the stop solution is 80% MeCN/20% 0.5 M Tris base.

Fluorescence is read either immediately (for CEC, AMMC, BFC), or after 20 min (for CYP2C9 and CYP3A4 using DBF as substrate) on a PerkinElmer EnVision® reader at the appropriate excitation and emission wavelength (cf. 0).

The percentage inhibition of CYP by the test compound is then calculated by normalizing the data to blank samples: 100% inhibition is the blank sample stopped before addition of the enzyme/substrate mix, and 0% inhibition is the blank sample stopped after the enzymatic reaction has occurred (50 min).

Inhibition Assay Conditions Used for Each CYP450 Isoenzyme Studied

| Substrate (µM) | CYP3A4 | CYP3A4 | CYP2C19 | CYP2C9 | CYP1A2 | CYP2D6 |
|---|---|---|---|---|---|---|
| DBF | 1 | — | — | 0.5 | — | — |
| CEC | — | — | 35 | — | 4 | — |
| AMMC | — | — | — | — | — | 0.5 |
| BFC | — | 120 | — | — | — | — |
| Phosphate buffer pH 7.4 (mM) | 200 | 90 | 25 | 25 | 25 | 25 |
| Enzyme (pmol/well) | 1 | 1.5 | 6 | 2 | 1.5 | 3 |
| Incubation time (min) | 50 | 50 | 50 | 50 | 50 | 50 |
| Positive control | ketoconazole | ketoconazole | fluvoxainine | sulfaphenazole | fluvoxamine | quinidine |
| Excitation wavelength (nm) | 485 | 400 | 400 | 485 | 400 | 380 |

-continued

| Substrate (μM) | CYP3A4 | CYP3A4 | CYP2C19 | CYP2C9 | CYP1A2 | CYP2D6 |
|---|---|---|---|---|---|---|
| Emission wavelength (nm) | 530 | 530 | 460 | 530 | 460 | 460 |

AMMC: aminoethyl-7-methoxy-4-methylcoumarin
BFC: 7-benzyloxy-4-trifluoromethylcoumarin
CEC: 3-cyano-7-ethoxycoumarin
DBF: dibenzylfluorescein 5 Time-Dependent CYP3A4 Inhibition Time-dependent CYP3A4 inhibition by the compounds, assessed in pooled HLM, is determined via $IC_{50}$ determination according to Grimm et al. Drug Metabolism and Disposition 2009, 37, 1355-1370 and the draft FDA Guidance for Industry (Drug Interaction Studies—Study Design, Data Analysis, Implications for Dosing, and Labeling Recommendations), 2006, http://www.fda.gov/oder/guidance/index.htm. Testosterone is used as probe substrate and troleandomycin is used as positive control.

The invention claimed is:

1. A compound according to Formula I:

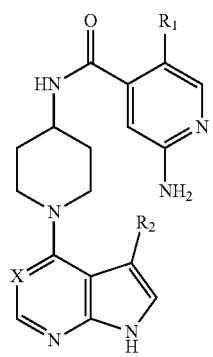

wherein
$R^1$ is H, $CH_3$, F or Cl;
X is N, CH or C—CN; and
$R^2$ is $CH_3$ or halogen;
or a pharmaceutically acceptable salt, or a solvate, or a pharmaceutically acceptable salt of a solvate thereof.

2. The compound, or a pharmaceutically acceptable salt thereof, according to claim 1, wherein $R^1$ is F.

3. The compound, or a pharmaceutically acceptable salt thereof, according to claim 1, wherein $R^2$ is $CH_3$.

4. The compound, or a pharmaceutically acceptable salt thereof, according to claim 1, wherein X is CH.

5. The compound, or a pharmaceutically acceptable salt thereof, according to claim 1, wherein X is C—CN.

6. The compound, or a pharmaceutically acceptable salt thereof, according to claim 1, wherein X is N.

7. The compound or pharmaceutically acceptable salt thereof according to claim 1, wherein the compound is:

2-amino-5-fluoro-N-[1-(5-methyl-7H-pyrrolo[2,3-d]pyrimidin-4-yl)-4-piperidyl]pyridine-4-carboxamide,
2-amino-5-methyl-N-[1-(5-methyl-7H-pyrrolo[2,3-d]pyrimidin-4-yl)-4-piperidyl]pyridine-4-carboxamide,
2-amino-5-chloro-N-[1-(5-methyl-7H-pyrrolo[2,3-d]pyrimidin-4-yl)-4-piperidyl]-pyridine-4-carboxamide,
2-amino-N-[1-(5-chloro-7H-pyrrolo[2,3-d]pyrimidin-4-yl)-4-piperidyl] pyridine-4-carboxamide, 2-amino-N-[1-(5-chloro-7H-pyrrolo[2,3-d]pyrimidin-4-yl)-4-piperidyl]-5-fluoro-pyridine-4-carboxamide, 2-amino-N-[1-(5-cyano-3-methyl-1H-pyrrolo[2,3-b]pyridin-4-yl)-4-piperidyl]-5-fluoro-pyridine-4-carboxamide, or 2-amino-N-[1-(3-chloro-1H-pyrrolo[2,3-b]pyridin-4-yl)-4-piperidyl]-5-fluoro-pyridine-4-carboxamide.

8. A pharmaceutical composition comprising a compound or pharmaceutically acceptable salt thereof according to claim 1, and a pharmaceutically acceptable carrier.

9. A method for treatment of pain, inflammatory conditions, arthritis, rheumatoid arthritis, osteoarthritis, liver fibrosis, pulmonary fibrosis, steatohepatitis, and/or NASH comprising administering an effective amount of a compound or pharmaceutically acceptable salt thereof according to claim 1 to an individual in need thereof.

10. A process for preparing a compound of formula I or a pharmaceutically acceptable salt, or a solvate, or a pharmaceutically acceptable salt of a solvate thereof, according to claim 1, which comprises:

(a) reacting a compound of formula II:

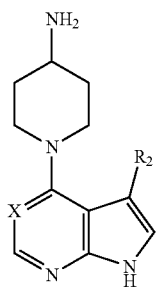

wherein X and $R_2$ are as defined in claim 1, with a compound of formula III:

or a protected derivative thereof, wherein $R^1$ is as defined in claim 1;
  (b) deprotecting a protected derivative of a compound of formula I;
  (c) interconverting a compound of formula I or protected derivative thereof to a further compound of formula I or protected derivative thereof; and
  (d) optionally forming a pharmaceutically acceptable salt of a compound of formula I.

11. A method for treatment of pain, inflammatory conditions, arthritis, rheumatoid arthritis, osteoarthritis, liver fibrosis, pulmonary fibrosis, steatohepatitis, and/or NASH comprising administering a pharmaceutical composition according to claim 8 to an individual in need thereof.

12. A pharmaceutical composition comprising a compound or pharmaceutically acceptable salt thereof according to claim 7, and a pharmaceutically acceptable carrier.

13. A method for treatment of pain, inflammatory conditions, arthritis, rheumatoid arthritis, osteoarthritis, liver fibrosis, pulmonary fibrosis, steatohepatitis, and/or NASH comprising administering an effective amount of a compound or pharmaceutically acceptable salt thereof according to claim 7 to an individual in need thereof.

14. A method for treatment of pain, inflammatory conditions, arthritis, rheumatoid arthritis, osteoarthritis, liver fibrosis, pulmonary fibrosis, steatohepatitis, and/or NASH comprising administering a pharmaceutical composition according to claim 12 to an individual in need thereof.

\* \* \* \* \*